United States Patent
Zhan et al.

(10) Patent No.: US 12,398,168 B2
(45) Date of Patent: Aug. 26, 2025

(54) PREPARATION METHOD OF A GLYCOSIDE COMPOUND

(71) Applicant: SHANGHAI HUTCHISON PHARMACEUTICALS LIMITED, Shanghai (CN)

(72) Inventors: Changsen Zhan, Shanghai (CN); Ping Tian, Shanghai (CN); Chunxiao Cui, Shanghai (CN); Jiange Zhang, Shanghai (CN); Junjie Zhou, Shanghai (CN); Guoqiang Lin, Shanghai (CN); Wenwen Xu, Shanghai (CN); Zhengguang Zhang, Shanghai (CN)

(73) Assignee: SHANGHAI HUTCHISON PHARMACEUTICALS LIMITED, Shanghai (CN)

( * ) Notice: Subject to any disclaimer, the term of this patent is extended or adjusted under 35 U.S.C. 154(b) by 818 days.

(21) Appl. No.: 17/762,387

(22) PCT Filed: Jan. 4, 2021

(86) PCT No.: PCT/CN2021/070109
§ 371 (c)(1),
(2) Date: Mar. 22, 2022

(87) PCT Pub. No.: WO2021/139621
PCT Pub. Date: Jul. 15, 2021

(65) Prior Publication Data
US 2022/0380399 A1    Dec. 1, 2022

(30) Foreign Application Priority Data
Jan. 9, 2020   (CN) .......................... 202010022440.2

(51) Int. Cl.
C07H 1/06      (2006.01)
C07H 3/02      (2006.01)

(52) U.S. Cl.
CPC .................. *C07H 3/02* (2013.01); *C07H 1/06* (2013.01)

(58) Field of Classification Search
None
See application file for complete search history.

(56) References Cited

U.S. PATENT DOCUMENTS

| 11,325,937 B2* | 5/2022 | Lin ............................ A61P 9/00 |
| 2004/0235081 A1* | 11/2004 | Burton ...................... C12Q 1/34 |
| | | 435/23 |

FOREIGN PATENT DOCUMENTS

| CN | 1911949 A | 2/2007 |
| CN | 101130560 A | 2/2008 |
| CN | 102304157 A | 1/2012 |
| CN | 107936065 A | 4/2018 |
| CN | 109422783 A | 3/2019 |
| WO | 2015154721 A1 | 10/2015 |
| WO | 2016109990 A1 | 7/2016 |
| WO | WO-2020001166 A1 * | 1/2020 ......... A61K 31/7034 |

OTHER PUBLICATIONS

International Search Report Issued in International Application No. PCT/CN2021/070109, Issued Apr. 12, 2021, 2 pages.

* cited by examiner

*Primary Examiner* — Traviss C Mcintosh, III
(74) *Attorney, Agent, or Firm* — Getech Law LLC; Jun Ye

(57) ABSTRACT

Preparation method of glycoside compounds is involved in the invention, with the advantages of short synthesis steps, high stereoselectivity and yield, simple production operation, low equipment requirements, environmental protection and suitability for industrial mass production.

7 Claims, No Drawings

PREPARATION METHOD OF A GLYCOSIDE COMPOUND

TECHNICAL FIELD

Preparation method of a glycoside compound is involved in the invention, which belongs to the field of pharmaceutical chemical synthesis.

TECHNICAL BACKGROUND

Cerebrovascular diseases refer to a group of diseases in which cerebral artery or neck artery that dominates brain becomes diseased, thus arousing intracranial blood circulation obstacle and brain tissue damage. Clinically, main performances are sudden fainting, unconsciousness, or accompanied by facial paralysis, unsmooth speech and hemiplegia. Ischemic cerebrovascular diseases mainly refer to cerebral thrombosis, cerebral infarction, multiple cerebral infarction, etc.; the disease is featured by sudden onset, rapid progress, critical condition, and frequent occurrence in the elderly, which easily leads to multiple viscera function damage, poor prognosis and high mortality. Ischemic cerebrovascular disease is called cerebral infarction because the acute interruption of blood flow of cerebral artery causes ischemic necrosis of brain tissue in the corresponding area.

Cerebral stroke, also known as "stroke" and cerebral vascular accident (CVA), is one of the most important fatal diseases in the world. It is a group of diseases that cause brain tissue damage due to sudden rupture of blood vessels in the brain or vascular obstruction that prevents blood from flowing into the brain, including ischemic and hemorrhagic stroke. Incidence of ischemic stroke is higher than that of hemorrhagic stroke. Ischemic stroke is the regional blood supply obstacles of local brain tissue caused by various reasons, which leads to ischemic and anoxic lesions and necrosis of brain tissue, and further leads to corresponding neurological disfunction clinically, which affects life quality of patients seriously.

The research focus of pathological intervention of ischemic injury is mainly to improve cerebrovascular circulation and neuroprotection. Among them, the measures to improve cerebrovascular circulation are mainly antithrombotic therapy. Antithrombotic drugs are divided into thrombolytic drugs, antiplatelet aggregation drugs and anticoagulants. At present, neuroprotective drugs mainly include calcium antagonists, glutamate antagonists, glutamate release inhibitors, GABA receptor agonists, free radical scavengers and cell membrane stabilizers, etc.

In recent years, the findings in angiogenesis have provided a new direction for the effective treatment of ischemic vascular diseases, which has become a research focus in the medical field. Angiogenesis can promote the survival of neurons after stroke, improve patients' neurologic deficits and the quality of life after stroke, but the influencing factors and regulatory mechanism of angiogenesis after stroke are complex. In recent years, it is found by research that PAR 1 participates in the processes of angiogenesis and nerve repair after stroke. Angiogenesis refers to the formation of new capillaries by budding and/or non-budding on the basis of the original blood vessels. The main process of angiogenesis includes: Increase of vascular permeability; production of proteolytic enzyme, degradation of extracellular matrix and promotion of endothelial cell proliferation; endothelial cells are separated from basement membrane, migrating to perivascular space, and forming a three-dimensional lumen through adhesion-proliferation-reconstruction; they differentiate into new capillaries; interstitial cells enter the vessel wall under the induction of mediators, making the vessel mature stably. Under normal physiological conditions, once the blood vessels in the body are formed, they maintain at a high degree of stability, and are regulated by many key molecules with positive or negative regulating effects (i.e., vascular growth promoting factors and vascular growth inhibiting factors). The start of angiogenesis only turns on shortly with the appearance of a stimulating signal, and then turns off immediately, maintaining a dynamic balance between angiogenesis and loss. The factors affecting angiogenesis after stroke include: Local supply of blood and oxygen; thrombin and its concentration changes; Level of angiogenic factors, such as hypoxia inducing factor 1α (HIF-1α), vascular endothelial growth factor (VEGF), matrix metalloproteinases (MMPs), angiopoietin 1 (Ang-1), angiopoietin 2 (Ang-2), etc. PAR 1 usually interacts with angiogenic factors to promote angiogenesis. VEGF is currently recognized as a key factor for angiogenesis. Under normal circumstances, VEGF is only expressed in a small amount to maintain the blood vessel density and permeability in physiological state. However, some pathological processes such as inflammation, tumor, wound healing, ischemia and hypoxia can promote the expression of VEGF. The expression of VEGF in nerve cells and glial cells around the stroke focus increased in stroke patients. By specifically binding with endothelial cell surface receptors, VEGF promoted the proliferation and migration of vascular endothelial cells, increased vascular permeability and enhanced the expression of factors degrading extracellular matrix, thus promoting angiogenesis.

Glycoside compounds exist in nature widely, and these compounds have various biological activities. Numerous glycoside compounds have attracted people's attention because of their special medicinal value. At present, the main way to obtain glycoside compounds is still biological extraction, while chemical synthesis still has great limitations in terms of production scale, cost and environmental protection.

In previous research, the inventor found that the tautomers, optical isomers, solvates, polymorphs, pharmaceutically acceptable salts, esters, pharmaceutically acceptable prodrugs or derivatives of glycoside compounds of specific structures can prevent and/or treat ischemic cerebrovascular diseases. These glycoside compounds can be applied to all symptoms and/or pathological changes of brain tissue ischemia from the early stage to the late stage evoked by vascular diseases caused by vascular wall diseases, blood composition changes and/or hemodynamic changes.

The glycoside compound can be a glycoside compound shown in the following formula I, its tautomer, optical isomer, solvate, polymorph, pharmaceutically acceptable salt, ester, pharmaceutically acceptable prodrug or derivative:

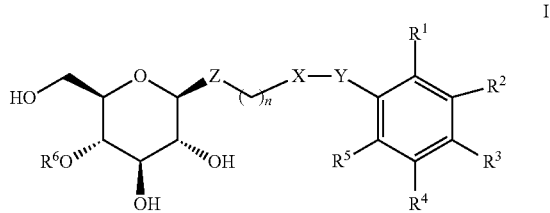

It is used for preventing and/or treating ischemic cerebrovascular diseases, and $R^1$, $R^2$, $R^3$, $R^4$ and $R^5$ are each independently selected from hydrogen, hydroxyl, sulfydryl, substituted or unsubstituted $C_1$-$C_{20}$ alkoxy (such as substituted or unsubstituted $C_1$-$C_{10}$ alkoxy, such as substituted or unsubstituted $C_1$-$C_6$ alkoxy), nitryl or halogen;

Or any two adjacent phases in $R^1$, $R^2$, $R^3$, $R^4$ and $R^5$ form a 5- to 7-membered heterocyclic ring with the carbon atoms connected to its benzene ring (such as $R^2$ and $R^3$ form a 5- to 7-membered heterocyclic ring), and the heteroatom of the heterocyclic ring is O or S (such as O); the number of heteroatoms is 1 or more (such as two); when the number of heteroatoms is multiple, the heteroatoms are the same or different;

The substituent in the substituted or unsubstituted $C_1$-$C_{20}$ alkoxy is selected from $C_3$-$C_{20}$ cycloalkyl (such as $C_3$-$C_{10}$ cycloalkyl, or $C_3$-$C_6$ cycloalkyl), $C_2$-$C_{20}$ alkylene (such as $C_2$-$C_6$ alkylene, such as $C_2$-$C_4$ alkylene, or

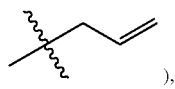 [SMILES: *CC=C]), substituted or unsubstituted C6-C20 aryl (such as substituted or unsubstituted C6-C10 aryl, or substituted or unsubstituted aryl or naphthyl), halogen (such as fluorine, chlorine, bromine or iodine), substituted or unsubstituted C2-C20 heteroaryl. The heteroatoms in the substituted or unsubstituted C2-C20 heteroaryl can be selected from one or more of N, S and O (such as 1 heteroatom; or N heteroatoms; such as, the substituted or unsubstituted C2-C20 heteroaryl may be aromatic heteroaryl with only one ring).

For example, substituted or unsubstituted $C_2$-$C_{10}$ heteroaryl, or substituted or unsubstituted C2-$C_6$ heteroaryl), $C_3$-$C_6$ cycloalkoxy (such as

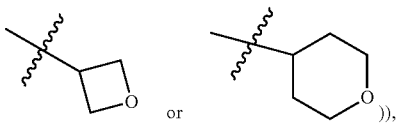 [SMILES: *C1COC1 ; *C1CCOCC1])), $C_1$-$C_{20}$ alkoxy (such as $C_1$-$C_{10}$ alkoxy, such as $C_1$-$C_6$ alkoxy, such as methoxy, ethoxy or propoxy) or $C_1$-$C_{20}$ alkyl (such as $C_1$-$C_{10}$ alkyl; such as $C_1$-$C_6$ alkyl; such as $C_1$-$C_3$ alkyl);

The substituted or unsubstituted $C_1$-$C_{20}$ aryl and the substituted or unsubstituted $C_2$-$C_{20}$ heteroaryl are each independently selected from halogen (such as fluorine, chlorine, bromine or iodine) or halogen (such as fluorine, chlorine, bromine or iodine)-substituted $C_1$-$C_{20}$ alkyl (the number of substituents in the halogen-substituted $C_1$-$C_{20}$ alkyl can be 1 or more, and when there are more substituents, they can be the same or different; such as $C_1$-$C_{10}$ alkyl substituted by halogen; such as $C_1$-$C_6$ alkyl substituted by halogen; such as $C_1$-$C_3$ alkyl substituted by halogen; or —$CF_3$, —$CHF_2$ or —$CH_2F$);

X is $CH_2$, $NR^7$, O 或 S;
Y $CH_2$, $NR^8$, O or S;
Z is O or S;
$R^7$ and $R^8$ are respectively hydrogen, aryl-substituted $C_1$-$C_6$ alkoxycarbonyl (such as benzyloxycarbonyl) or $C_1$-$C_6$ alkoxycarbonyl (such as tert-butoxycarbonyl);

$R^6$ is hydrogen or

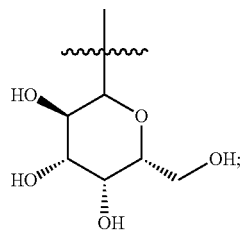 [SMILES: *C1O[C@H](CO)[C@H](O)[C@H](O)[C@H]1O]

n is 2, 3 or 4.

In previous preparation of glycoside compounds, the inventor used a 3-step synthesis method to obtain glycoside compounds. Taking the preparation of glycoside compound IV-3 as an example in the following:

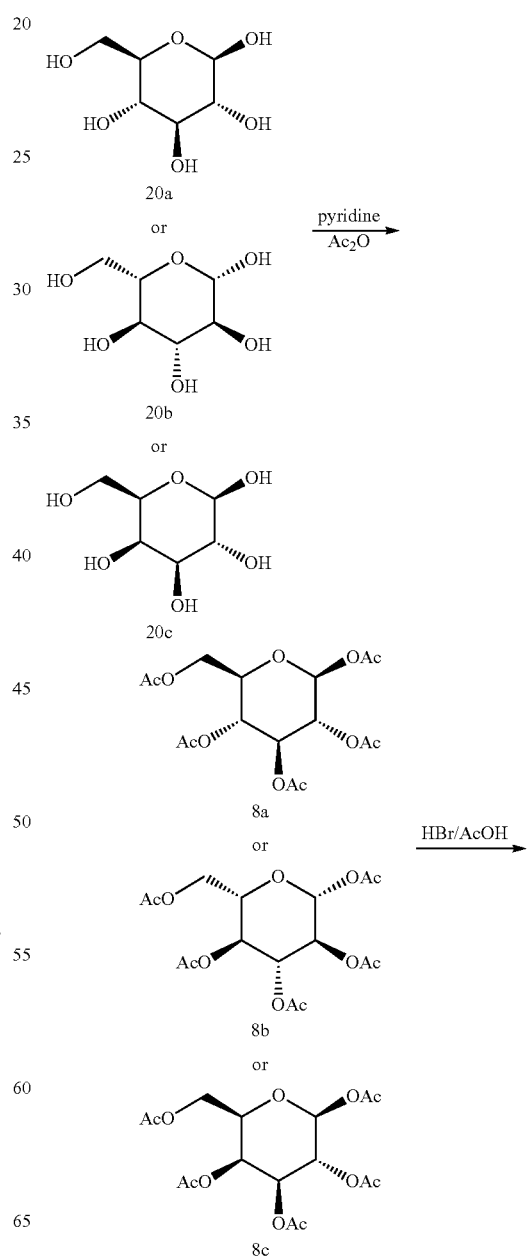

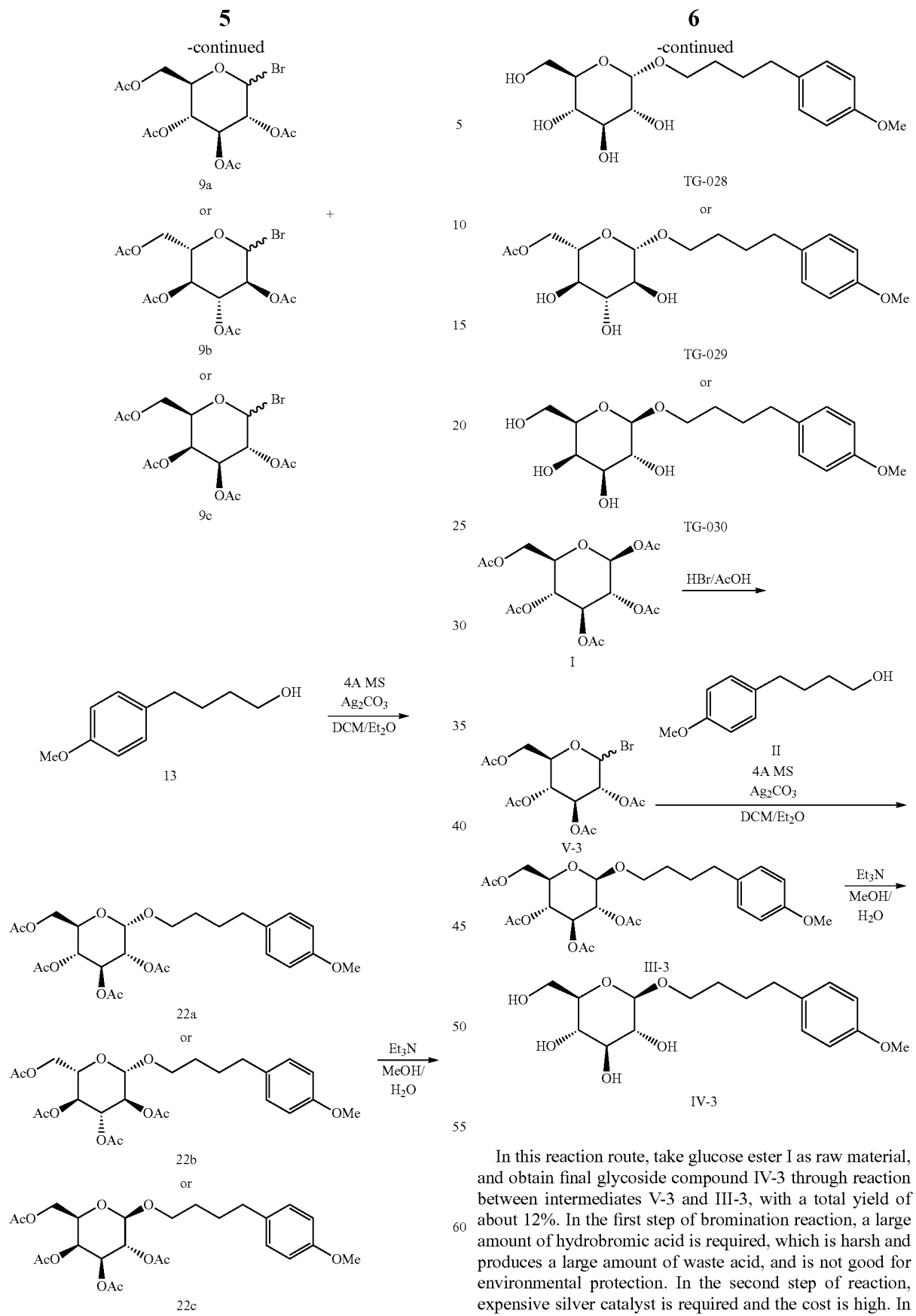

In this reaction route, take glucose ester I as raw material, and obtain final glycoside compound IV-3 through reaction between intermediates V-3 and III-3, with a total yield of about 12%. In the first step of bromination reaction, a large amount of hydrobromic acid is required, which is harsh and produces a large amount of waste acid, and is not good for environmental protection. In the second step of reaction, expensive silver catalyst is required and the cost is high. In the last step of deacetylation, excessive triethylamine is used as alkali, which increases the difficulty of separation and purification, and the yield in the last step is only 64%.

At present, main methods of chemical synthesis of glycoside compounds include: (1) Koenigs-Knorr glycosidation reaction, in which α-halogenated sugar is substituted with alcohol under the action of silver carbonate to prepare glucoside. In this method, glycosyl halide is synthesized firstly, and expensive silver catalyst is used, which is the most common synthesis method. (2) Schmidt trichloroacetimidate glycosidation reaction, in which addition reaction of trichloroacetonitrile and glycosyl hemiacetal occurs under alkaline condition to obtain trichloroacetimidate, which then reacts with alcohol or phenol under Lewis acid catalysis to produce glucoside. In this method, class 3 carcinogen trichloroacetonitrile, and trichloroacetamide, a genotoxic by-product produced during that reaction are used. (3) Kahne glycosidation reaction, in which glycosyl sulfoxide is activated by trifluoromethanesulfonic anhydride, and reacts with alcohol and phenol to obtain corresponding glycoside compounds. The reaction temperature is −30~−78° C., and the conditions are harsh. (4) Other methods of glycoside synthesis include phase transfer catalysis method, trifluoroacetate method and so on, which are all improvements of classical methods, but there are also some problems or limitations.

So, in the existing technology, there are still many difficulties and challenges in how to synthesize and prepare glycoside compounds with high selectivity and efficiency, more economy and more environmental protection. Through careful research on glycoside synthesis process route, through extensive experiments and creative labor, the inventor found a preparation method for glycosides, which can shorten process steps, improve yield and stereoselectivity of compounds, reduce production cost and is suitable for industrial mass production. For a series of glycoside compounds constructed by this method, some compounds with specific structures have potential application prospects for cerebrovascular disease drugs.

CONTENT OF INVENTION

Preparation method of glycoside compounds is provided in the invention, which is featured by the following two steps of reactions:

(1) Acetyl-protected glucose (I) and alcohol compounds shown in formula (II) react under the catalysis of Lewis acid to obtain intermediates shown in formula (III).

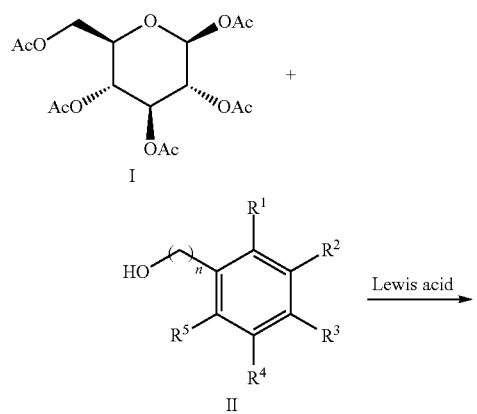

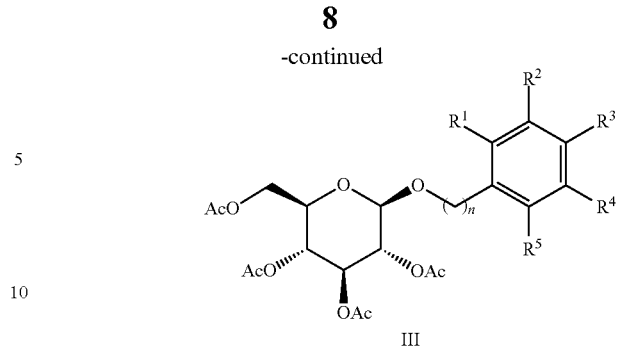

(2) Remove acetyl protecting group from the intermediates shown in formula (III) in the presence of alkali to obtain final glycoside compounds shown in formula (H$^+$).

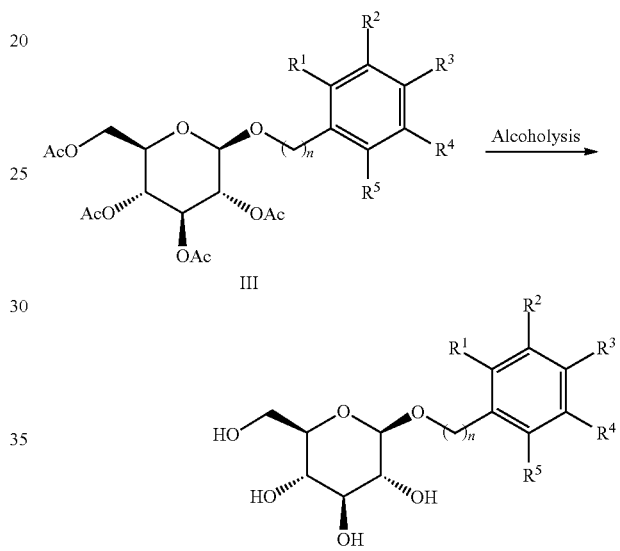

In formulas II, III and IV, substituents $R^1$, $R^2$, $R^3$, $R^4$ and $R^5$ are independently selected from hydrogen, hydroxyl, substituted or unsubstituted $C_1$-$C_{20}$ alkoxyl, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, substituted or unsubstituted aryl, heteroaryl, cycloalkyl, heterocyclyl, nitryl or halogen;

n is 4, 5, or 6.

Preferably, reaction in step (1) is conducted in the first organic solvent; the organic solvent is one or more of dichloromethane, chloroform, toluene, xylene, dimethylformamide, dioxane, methyl tert-butyl ether or tetrahydrofuran.

Preferably, Lewis acid in step (1) is one or more of tin tetrachloride, zinc chloride, aluminum trichloride and boron trifluoride complex, such as boron trifluoride diethyl ether complex, boron trifluoride butyl ether complex, boron trifluoride tetrahydrofuran complex, boron trifluoride acetonitrile complex or trimethylsilyl trifluoromethanesulfonate.

Preferably, step (1) is conducted under the protection of inert gas nitrogen or argon.

Preferably, reaction temperature in step (1) is −15~60° C. More preferable reaction temperature is −5~40° C.

Preferably, reaction in step (2) is conducted in the second organic solvent; the second organic solvent is one or more of methanol, ethanol, isobutanol or tert-butanol.

Preferably, alkaline condition in step (2) refers to the presence of sodium hydroxide, potassium hydroxide or sodium salt of $C_1$-$C_4$ alkanol, more preferably the presence of sodium methoxide, sodium ethoxide or sodium tert-butoxide.

Specific operation steps of the invention are as follows: 1) In step (1), first, replace reaction flask with inert gas for 3 times, add the first solvent, and start stirring. Then, add β-D-glucose pentaacetate1,2,3,4,6-penta-O acetyl-β-D-glucopyranose I and alcohol II; control the temperature of the reaction flask to −15~−60° C., more preferably −5~−40° C. Add Lewis acid, and continue to stir for 2-24 h, preferably 4-12 h.

2) After reaction in step (1), drop water into system to quench the reaction, separate liquid, wash the organic phase with $Na_2CO_3$ water solution, separate liquid again, and wash the organic phase with water once again. Collect organic phase after liquid separation. Conduct column chromatography isolation after concentrating organic phase to no obvious fraction, and obtain compound III.

3) In step (2), first, replace reaction flask with inert gas for 3 times, add the second solvent, and start stirring. Add intermediate III into reaction flask, control temperature at 25±5° C., add sodium hydroxide, potassium hydroxide or sodium salt of $C_1$-$C_4$ alkanol, more preferably sodium methoxide, sodium ethoxide or sodium tert-butoxide into reaction flask, and stir to react for 2 h.

4) After reaction in step (2), conduct diatomite filtration, and collect filtrate after rinsing with the second solvent. Add ($H^+$) ion exchange resin and stir for 10 h. Filter to remove ($H^+$) ion exchange resin. Conduct column chromatography isolation after organic phase concentration, and obtain final product IV.

According to preparation method of the invention, the synthesized glycoside compounds are featured by compound IV to be the following example but not limited to the following structure:

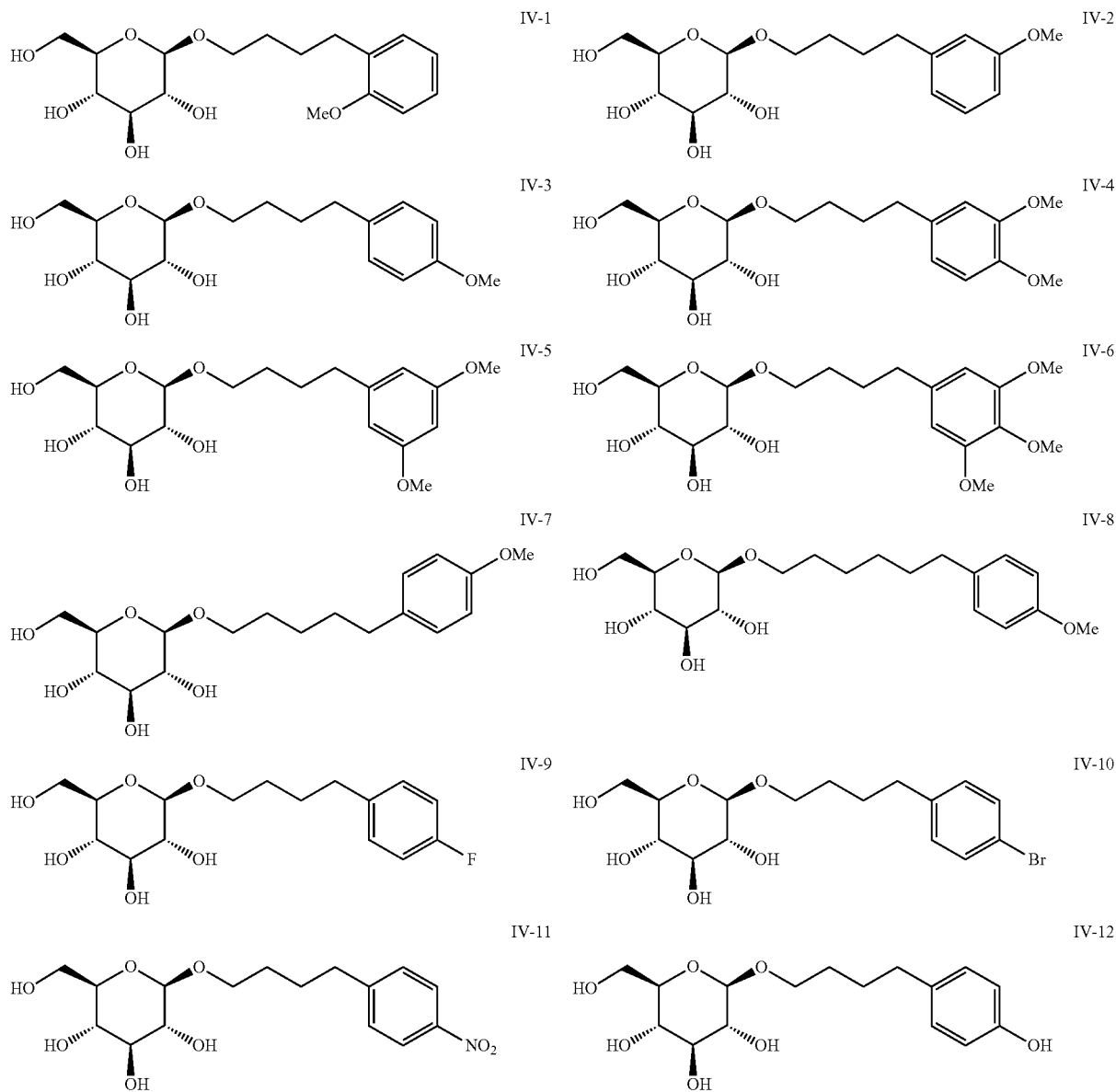

-continued
IV-13
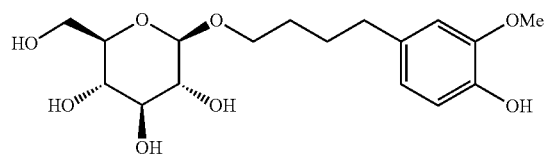
IV-14
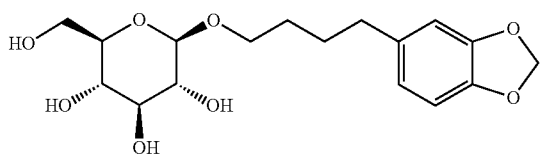
IV-15
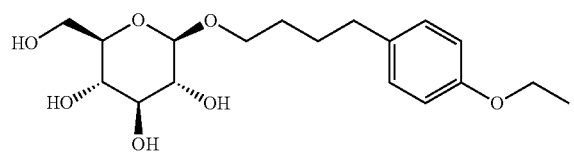
IV-16
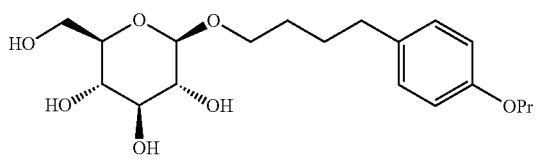
IV-17
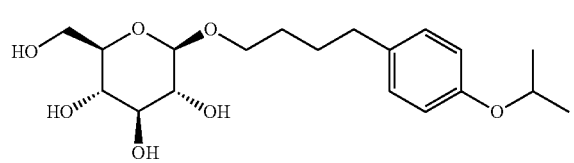
IV-18
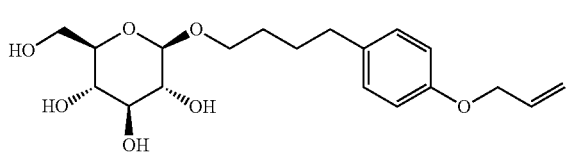
IV-19
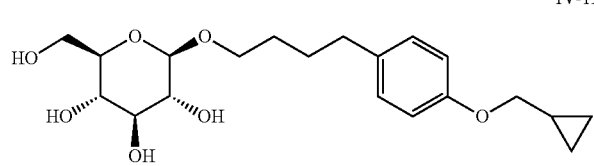
IV-20
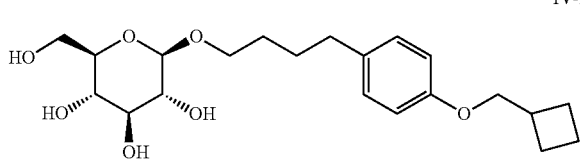
IV-21
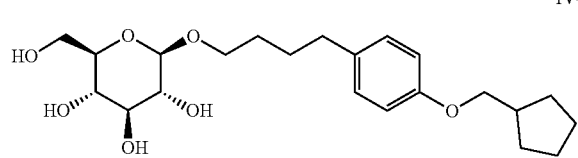
IV-22
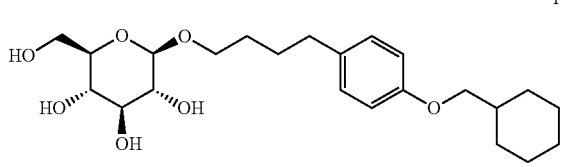
IV-23
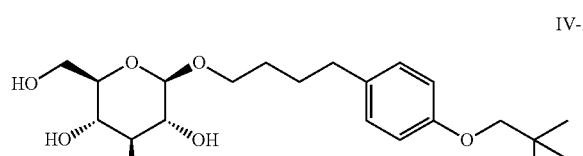
IV-24
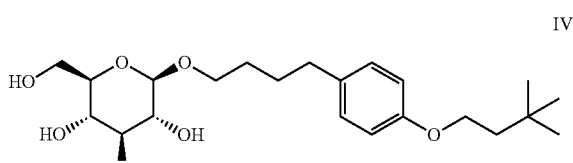
IV-25
IV-26
IV-27
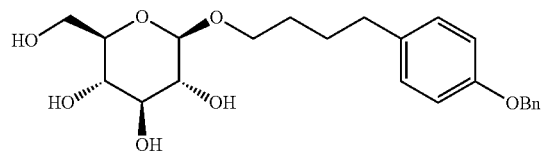
IV-28
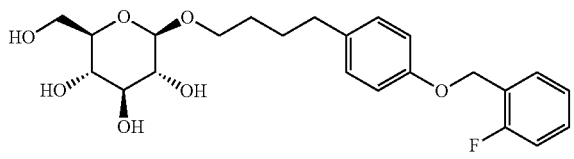
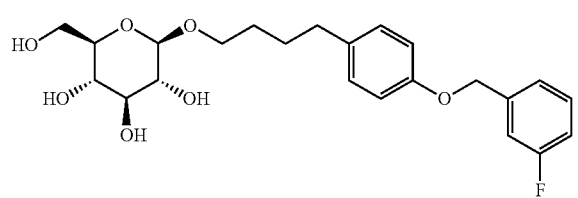

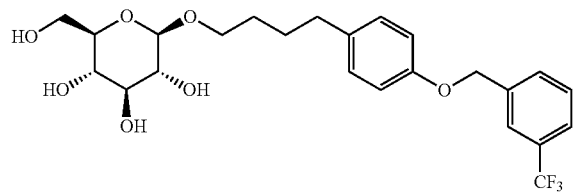

IV-29

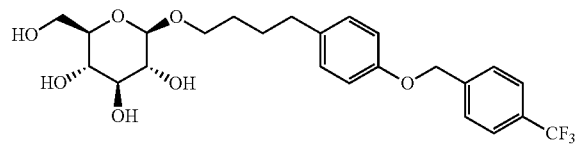

IV-30

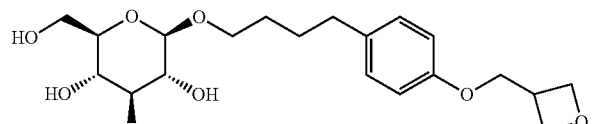

IV-31

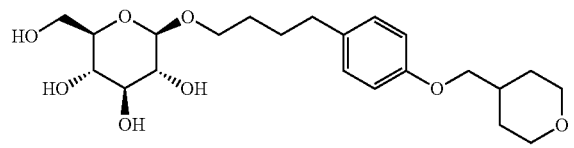

IV-32

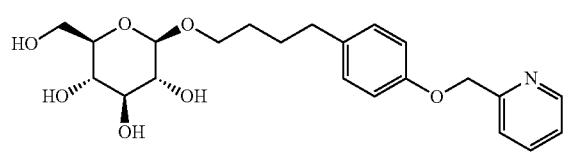

IV-33

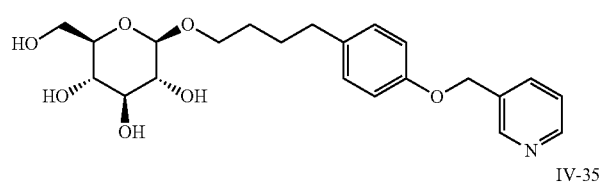

IV-34

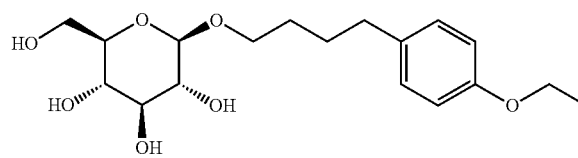

IV-35

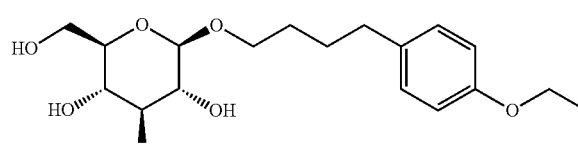

IV-36

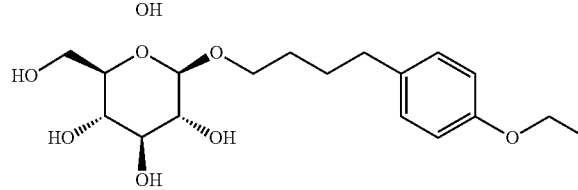

IV-37

Beneficial effects of this application are that: Compared with the existing synthesis technology of glycosides, the method of the invention is a direct condensation reaction of acetyl-protected glucosesthe monosaccharide protected by the full acetyl group and alcohols under the condition of Lewis acid catalysis to obtain the intermediate tetra-acetylated glycosides, and then alcoholysis of the intermediates under the alkaline condition to directly obtain the target glycoside compounds. The synthesis process has the advantages of short steps, high stereoselectivity and total yield, simple production and operation, low equipment requirements, environmental protection and suitability for industrial mass production. For a series of glycoside compounds constructed by this method, some compounds with specific structures have potential application prospects for cerebrovascular disease drugs.

Terminology

"Alkyl" includes both branched and straight chains saturated aliphatic hydrocarbon groups, with a specified number of carbon atoms, generally 1 to about 12 carbon atoms. As used herein, term $C_1$-$C_6$ alkyl refers to an alkyl group with 1 to about 6 carbon atoms. When $C_0$-$C_n$ alkyl is used in combination with another group herein, taking (phenyl) $C_0$-$C_4$ alkyl as an example, the specified group, in this case, phenyl is directly bonded through a single covalent bond ($C_0$) or connected through an alkyl chain with a specified number of carbon atoms (in this case, 1 to about 4 carbon atoms). Examples of alkyl include, but are not limited to: Methyl, ethyl, n-propyl, isopropyl, n-butyl, 3-methylbutyl, tert-butyl, n-pentyl, and sec-pentyl.

"Alkenyl" or "alkylene" refers to straight and branched hydrocarbon chains including one or more unsaturated carbon-carbon bonds, which can occur at any stable point along the chains. The alkenyl described herein generally have 2 to about 12 carbon atoms. Preferably, alkenyl is a low alkenyl, and those alkenyl groups have 2 to about 8 carbon atoms, such as $C_2$-$C_8$, $C_2$-$C_6$, and $C_2$-$C_4$ alkenyl. Examples of alkenyl include vinyl, allyl, and butenyl.

"Alkoxy" refers to an alkyl group as defined above with a specified number of carbon atoms connected by an oxygen bridge. Examples of alkoxy include, but are not limited to: Methoxy, ethoxy, 3-hexyloxy, and 3-methylpentyloxy.

Term "heterocyclic ring" refers to a 5- to 8-membered saturated ring, a partially unsaturated ring, or an aromatic ring containing 1 to about 4 heteroatoms selected from N, O and S with remaining ring atoms of carbon, or a 7- to 11-membered saturated ring, a partially unsaturated ring, or an aromatic heterocyclic ring system and a 10- to 15-membered tricyclic ring system, which contains at least 1 heteroatom selected from the polycyclic system of N, O and S, and each ring in the polycyclic system contains up to 4 heteroatoms independently selected from N, O and S. Unless otherwise specified, a heterocyclic ring can be connected to a group where it is substituted at any heteroatom and carbon atom and produces a stable structure. When specified, the heterocyclic ring described herein can be substituted on carbon or nitrogen atom as long as the obtained compound is stable. Optionally, nitrogen atoms in the heterocyclic ring can be quaternized. Preferably, the total number of heteroatoms in the heterocyclic group is no greater than 4 and the total number of S and O atoms in the heterocyclic group is no greater than 2, more preferably, no greater than 1. Examples of heterocyclic group include: Pyridyl, indolyl, pyrimidinyl, pyridizinyl, pyrazinyl, imidazolyl, oxazolyl, furyl, thiophenyl, thiazolyl, triazolyl, tetrazolyl, isoxazolyl, quinolyl, pyrrolyl, pyrazolyl, benz[b]thiophenyl, isoquinolyl, quinazolinyl, quinoxalinyl, thienyl, isoindolyl, dihydrogen indole, 5,6,7,8-tetrahydroisoquinoline, pyridyl, pyrimidinyl, furyl, thienyl, pyrrolyl, pyrazolyl, pyrrolidyl, morpholinyl, piperazinyl, piperidinyl, and pyrrolidyl.

"Aryl" or "heteroaryl" refers to a stable 5- or 6-membered monocyclic or polycyclic ring containing 1 to 4 heteroatoms, or preferably 1 to 3 heteroatoms selected from N, O and S, with remaining ring atoms of carbon. When the total number of S and O atoms in heteroaryl exceeds 1, these heteroatoms are not adjacent to each other. Preferably, the total number of S and O atoms in heteroaryl is no greater than 2. Especially, the total number of S and O atoms in heteroaryl is no greater than 1. Optionally, the nitrogen atoms in the heterocyclic ring can be quaternized. When specified, these heteroaryl groups can also be substituted with carbon or non-carbon atoms or groups. Such substitution may include fusion with a 5- to 7-membered saturated cyclic groups optionally containing 1 or 2 heteroatoms independently selected from N, O and S, thus forming, for example, [1,3] dioxazole [4,5-c] pyridyl. Examples of heteroaryl include, but are not limited to: Pyridyl, indolyl, pyrimidinyl, pyridazinyl, pyrazinyl, imidazolyl, oxazolyl, furyl, phenylthio, thiazolyl, triazolyl, tetrazolyl, isoxazolyl, quinolyl, pyrrolyl, pyrazolyl, benz[b]thiophenyl, isoquinolyl, quinazolyl, quinoxalinyl, thienyl, isoindolyl, and 5,6,7,8-tetrahydroisoquinoline.

SPECIFIC IMPLEMENTATION

Next, the invention will be further described in detail in combination with specific implementation. Examples given are only to illustrate the invention, but not to limit the scope of it.

Example 1

Synthesis of 1-[4-(2-methoxyphenyl)butyl]-2,3,4,6-O-tetraacetyl-β-D-glucopyranoside III-1

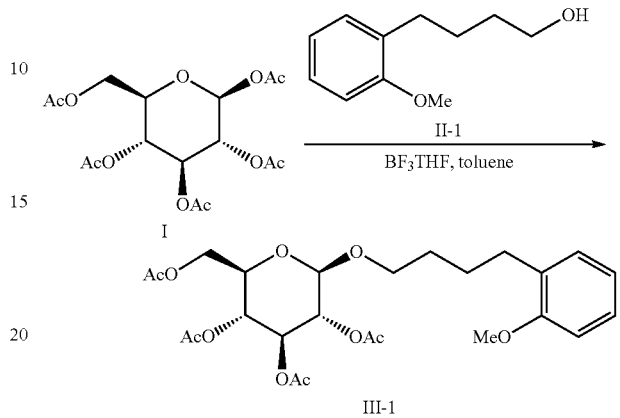

Operation steps: Replace reaction flask with nitrogen for 3 times, add toluene as solvent, and start stirring. Then, add β-D-glucose pentaacetate I and 4-(2-methoxyphenyl)butan-1-ol II-1 in turn. Cool reaction flask to 0±5° C., drop boron trifluoride tetrahydrofuran complex, and continue to stir for 12 h after that. After reaction, drop water to system to quench the reaction, separate liquid, wash organic phase with $Na_2CO_3$ water solution, separate liquid, and wash organic phase with water once again. Collect organic phase after liquid separation. Conduct column chromatography isolation after concentrating organic phase to no obvious fraction, and obtain compound III-1, with a yield of 30%. $^1$H NMR (400 MHz, $CDCl_3$): δ 6.32 (d, J=2.2 Hz, 2H), 6.29 (t, J=2.2 Hz, 1H), 5.20 (t, J=9.5 Hz, 1H), 5.08 (t, J=9.7 Hz, 1H), 4.98 (dd, J=9.6, 8.0 Hz, 1H), 4.48 (d, J=8.0 Hz, 1H), 4.26 (dd, J=12.3, 4.7 Hz, 1H), 4.13 (dd, J=12.3, 2.3 Hz, 1H), 3.89 (d, J=9.5 Hz, 1H), 3.78 (s, 6H), 3.68 (dd, J=9.9, 2.2 Hz, 1H), 3.49 (d, J=9.4 Hz, 1H), 2.55 (t, J=6.6 Hz, 2H), 2.08 (s, 3H), 2.05-1.97 (m, 9H), 1.63 (dd, J=11.5, 4.3 Hz, 4H). LRMS (ESI): [M+Na]$^+$ 533.5.

Synthesis of 1-(2-methoxy)phenylbutyl-β-D-glucopyranoside IV-1

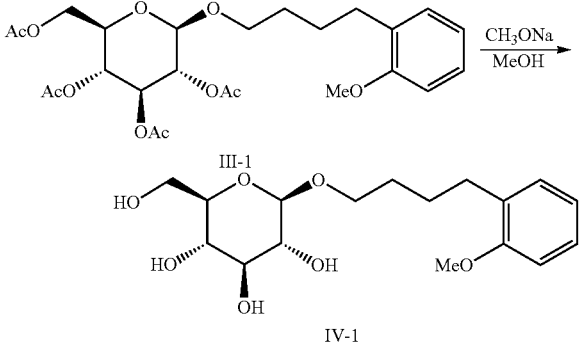

Operation steps: Replace reaction flask with nitrogen for 3 times, add methanol as solvent, and start stirring. Add intermediate III-1 into reaction flask, control temperature at 25±5° C., add sodium methoxide into reaction bottle, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-1, with a yield of 89%. ¹H NMR (400 MHz, CD₃OD): δ 7.17-7.06 (m, 2H), 6.88 (d, J=8.0 Hz, 1H), 6.82 (td, J=7.4, 0.9 Hz, 1H), 4.23 (d, J=7.8 Hz, 1H), 3.91 (m, 1H), 3.85 (dd, J=11.9, 2.0 Hz, 1H), 3.80 (s, 3H), 3.66 (dd, J=11.9, 5.3 Hz, 1H), 3.55 (m, 1H), 3.37-3.21 (m, 3H), 3.19-3.12 (m, 1H), 2.61 (t, J=7.0 Hz, 2H), 1.64 (m, 4H). LRMS(ESI): [M+Na]⁺ 365.1; HRMS(ESI): m/z Calcd for $C_{17}H_{27}O_7^+$ [M+H]⁺: calculated value is $C_{17}H_{27}O_7^+$343.1751, Found: 343.1748.

Example 2

Synthesis of 1-[4(3-methoxyphenyl)butyl]-2,3,4,6-O-tetraacetyl-β-D-glucopyranoside III-2

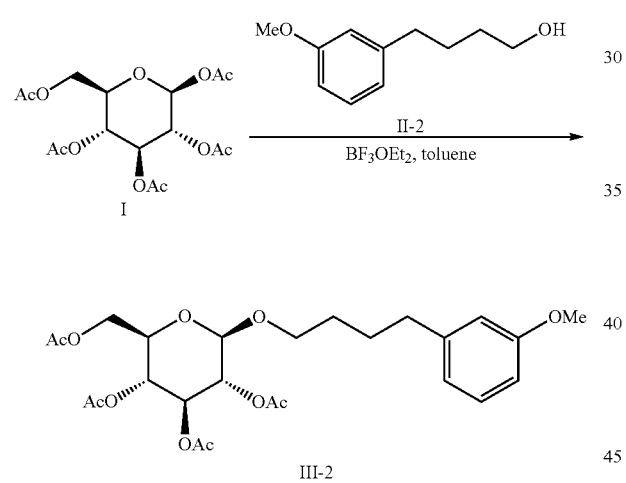

Operation steps: Replace reaction flask with nitrogen for 3 times, add toluene as solvent, and start stirring. Then, add β-D-glucose pentaacetate I and 4-(3-methoxyphenyl)butan-1-ol II-2 in turn. Cool reaction flask to 0±5° C., drop boron trifluoride ether complex, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after organic phase concentration, and obtain final product III-2, with a yield of 26%. ¹H NMR (300 MHz, CDCl₃): δ 7.19 (t, J=8.1 Hz, 1H), 6.81-6.65 (m, 3H), 5.28-4.88 (m, 3H), 4.48 (d, J=8.0 Hz, 1H), 4.32-4.06 (m, 2H), 3.88 (m, 1H), 3.80 (s, 3H), 3.68 (d, J=8.2 Hz, 1H), 3.51 (m, 1H), 2.59 (m, 2H), 2.03 (m, 12H), 1.64 (m, 4H). LRMS(ESI): [M+Na]⁺ 533.5.

Synthesis of 1-(3-methoxy)phenylbutyl-β-D-glucopyranoside IV-2

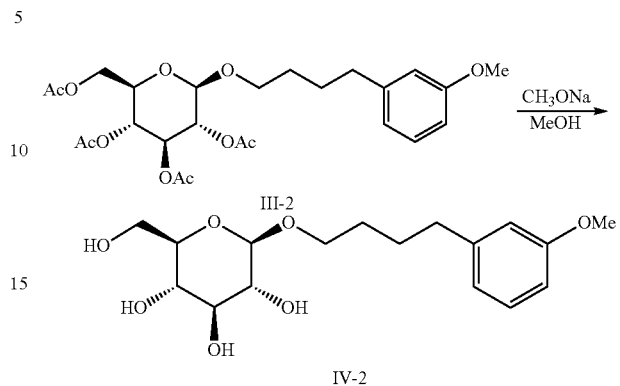

Operation steps: Replace reaction flask with nitrogen for 3 times, add methanol as solvent, and start stirring. Add intermediate III-2 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-2, with a yield of 92%. ¹H NMR (400 MHz, CD₃OD): δ 7.15 (t, J=7.8 Hz, 1H), 6.79-6.67 (m, 3H), 4.24 (d, J=7.8 Hz, 1H), 3.92 (dt, J=9.4, 6.4 Hz, 1H), 3.85 (dd, J=11.9, 1.8 Hz, 1H), 3.76 (s, 3H), 3.66 (dd, J=11.9, 5.2 Hz, 1H), 3.60-3.51 (m, 1H), 3.39-3.21 (m, 3H), 3.19-3.12 (m, 1H), 2.60 (t, J=7.3 Hz, 2H), 1.78-1.56 (m, 4H). LRMS(ESI): [M+Na]⁺ 365.1; HRMS(ESI): m/z Calcd for $C_{17}H_{30}O_7N^+$ [M+NH₄]⁺: calculated value $C_{17}H_{30}O_7N^+$360.2017, found: 360.2016.

Example 3

Synthesis of 1-[4(4-methoxyphenyl)butyl]-2,3,4,6-O-tetraacetyl-β-D-glucopyranoside III-3

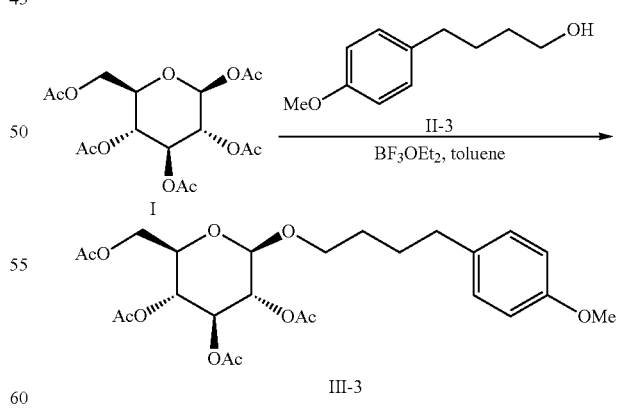

Operation steps: Replace reaction flask with nitrogen for 3 times, add toluene as solvent, and start stirring. Then, add β-D-glucose pentaacetate I and 4-(4-methoxyphenyl)butan-1-ol II-3 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after concentrating organic phase to no obvious fraction, and obtain compound III-3, with a yield of 37%. $^1$H NMR (400 MHz, CDCl$_3$): δ 7.0 (d, J=8.6 Hz, 2H), 6.82 (t, J=5.7 Hz, 2H), 5.20 (t, J=9.5 Hz, 1H), 5.08 (t, J=9.7 Hz, 1H), 4.98 (t, J=9.6, 8.0 Hz, 1H), 4.48 (d, J=8.0 Hz, 1H), 4.26 (dd, J=12.3, 4.7 Hz, 1H), 4.16-4.07 (m, 1H), 3.89 (dd, J=5.8, 3.7 Hz, 1H), 3.78 (s, 3H), 3.68 (m, J=9.9, 4.6, 2.4 Hz, 1H), 3.49 (dt, J=9.4, 6.1 Hz, 1H), 2.55 (t, J=6.6 Hz, 2H), 2.08 (s, 3H), 2.05-1.96 (m, 9H), 1.68-1.52 (m, 4H). LRMS(ESI): [M+Na]$^+$ 533.2.

Synthesis of
1-(4-methoxy)phenylbutyl-β-D-glucopyranoside
IV-3

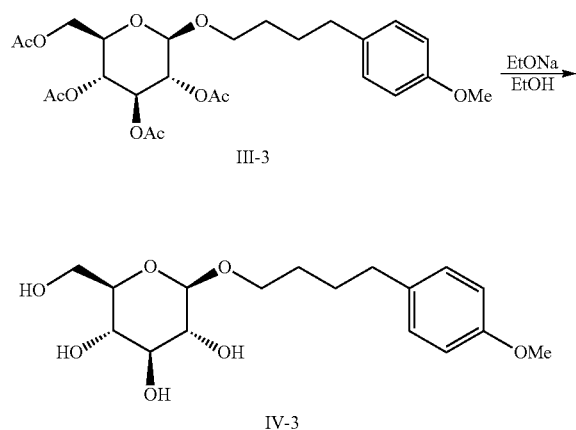

Operation steps: Replace reaction flask with nitrogen for 3 times, add ethanol as solvent, and start stirring. Add intermediate III-3 into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H$^+$) ion exchange resin. Conduct column chromatography isolation after organic phase concentration, and obtain final product IV-3, with a yield of 91%. $^1$H NMR (400 MHz, DMSO-d$_6$): δ 7.10 (d, J=8.5 Hz, 2H), 6.83 (d, J=8.5 Hz, 2H), 5.10-4.78 (m, 3H), 4.45 (t, J=5.9 Hz, 1H), 4.09 (d, J=7.8 Hz, 1H), 3.77 (m, J=12.5, 6.4 Hz, 3H), 3.71 (s, 3H), 3.65 (dd, J=10.8, 6.0 Hz, 1H), 3.49-3.37 (m, 2H), 3.17-2.98 (m, 3H), 2.92 (td, J=8.3, 5.1 Hz, 1H), 2.55-2.5 (m, 2H), 1.69-1.41 (m, 4H). LRMS(ESI): [M+Na]$^+$ 365.0; HRMS(ESI): m/z Calcd for C$_{17}$H$_{26}$O$_7$Na$^+$ [M+Na]$^+$: 365.1571, found: 365.1569.

Example 4

Synthesis of 1-[4(4-methoxyphenyl)butyl]-2,3,4,6-O-tetraacetyl-β-D-glucopyranoside III-3

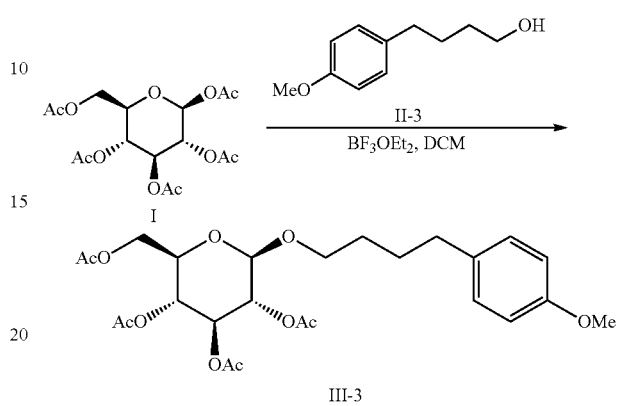

Operation steps: Replace reaction flask with nitrogen for 3 times, add dichloromethane as solvent, and start stirring. Then, add β-D-glucose pentaacetate I and 4-(4-methoxyphenyl)butan-1-ol II-3 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after concentrating organic phase to no obvious fraction, and obtain compound III-3, with a yield of 38%. $^1$H NMR and LRMS are consistent with Example 3.

Synthesis of
1-(4-methoxy)phenylbutyl-β-D-glucopyranoside
IV-3

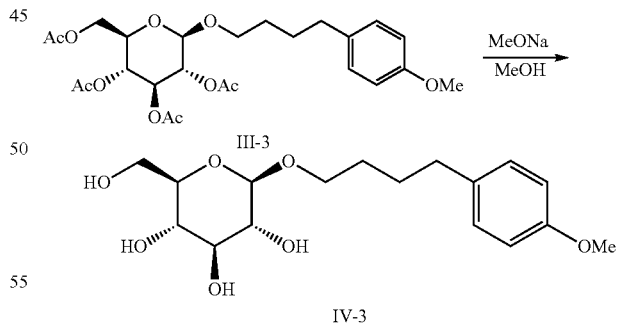

Operation steps: Replace reaction flask with nitrogen for 3 times, add methanol as solvent, and start stirring. Add intermediate III-3 (1.0 eq) into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-3, with a yield of 89%. $^1$H NMR and LRMS are consistent with Example 3.

Example 5

Synthesis of 1-[4(4-methoxyphenyl)butyl]-2,3,4,6-O-tetraacetyl-β-D-glucopyranoside III-3

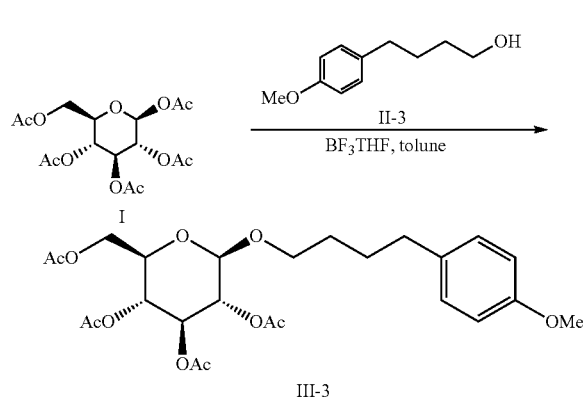

Operation steps: Replace reaction flask with nitrogen for 3 times, add toluene as solvent, and start stirring. Then, add β-D-glucose pentaacetate I and 4-(4-methoxyphenyl)butan-1-ol II-3 in turn. Cool reaction flask to 0±5° C., drop boron trifluoride tetrahydrofuran complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-3, with a yield of 34%. $^1$H NMR and LRMS are consistent with Example 3.

Synthesis of 1-(4-methoxy)phenylbutyl-β-D-glucopyranoside IV-3

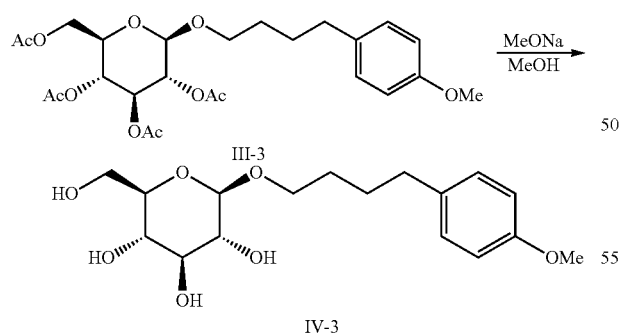

Operation steps: Replace reaction flask with nitrogen for 3 times, add methanol as solvent, and start stirring. Add intermediate III-3 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-3, with a yield of 85%. $^1$H NMR and LRMS are consistent with Example 3.

Example 6

Synthesis of 1-[4(4-methoxyphenyl)butyl]-2,3,4,6-O-tetraacetyl-β-D-glucopyranoside III-3

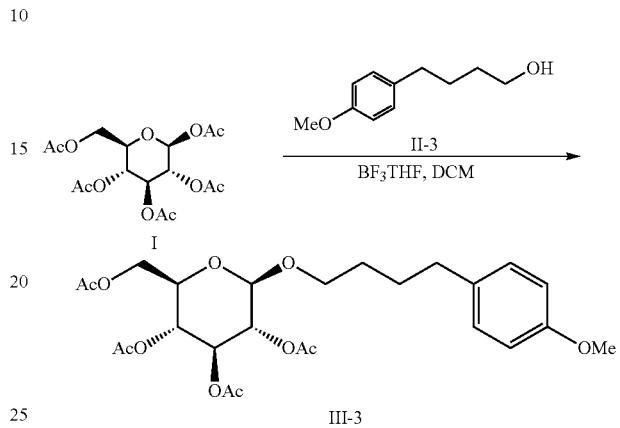

Operation steps: Replace reaction flask with nitrogen for 3 times, add dichloromethane as solvent, and start stirring. Then, add β-D-glucose pentaacetate I and 4-(4-methoxyphenyl)butan-1-ol II-3 in turn. Cool reaction flask to 0±5° C., drop boron trifluoride tetrahydrofuran complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-3, with a yield of 32%. $^1$H NMR and LRMS are consistent with Example 3.

Synthesis of 1-(4-methoxy)phenylbutyl-β-D-glucopyranoside IV-3

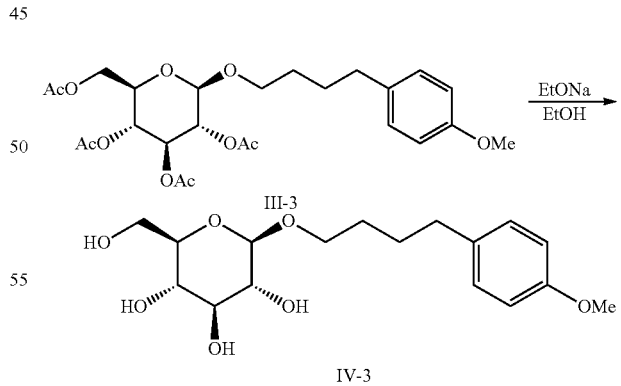

Operation steps: Replace reaction flask with nitrogen for 3 times, add ethanol as solvent, and start stirring. Add intermediate III-3 (1.0 eq) into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H⁺) ion exchange resin. Conduct column chromatography isolation after organic phase concentration, and obtain final product IV-3, with a yield of 84%. ¹H NMR and LRMS are consistent with Example 3.

Example 7

Synthesis of 1-[4(4-methoxyphenyl)butyl]-2,3,4,6-O-tetraacetyl-β-D-glucopyranoside III-3

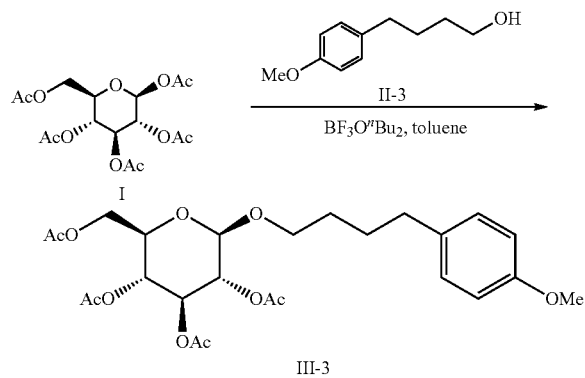

Operation steps: Replace reaction flask with nitrogen for 3 times, add toluene as solvent, and start stirring. Then, add β-D-glucose pentaacetate I and 4-(4-methoxyphenyl)butan-1-ol II-3 in turn. Cool reaction flask to 0±5° C., drop boron trifluoride dibutyl ether complex, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after concentrating organic phase to no obvious fraction, and obtain compound III-3, with a yield of 31%. ¹H NMR and LRMS are consistent with Example 3.

Synthesis of 1-(4-methoxy)phenylbutyl-β-D-glucopyranoside IV-3

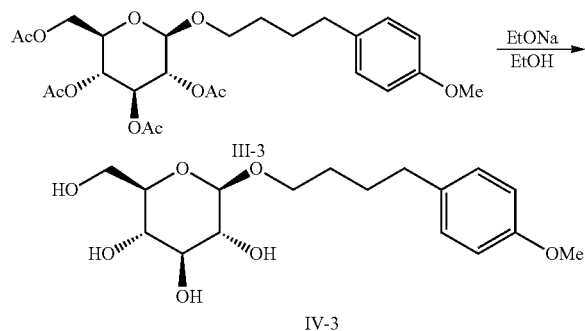

Operation steps: Replace reaction flask with nitrogen for 3 times, add ethanol as solvent, and start stirring. Add intermediate III-3 into reaction flask, control temperature at 25±5° C., add sodium ethoxide into reaction flask, and stir to react for 2 h. After reaction, conduct diatomite filtration, and collect filtrate after ethanol leaching. Add (H⁺) ion exchange resin and stir for 10 h. Filter to remove (H⁺) ion exchange resin. Conduct column chromatography isolation after organic phase concentration, and obtain final product IV-3, with a yield of 91%. ¹H NMR and LRMS are consistent with Example 3.

Example 8

Synthesis of 1-[4(4-methoxyphenyl)butyl]-2,3,4,6-O-tetraacetyl-β-D-glucopyranoside III-3

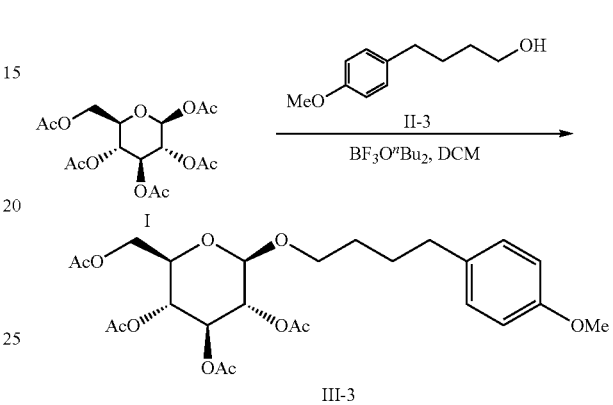

Operation steps: Replace reaction flask with nitrogen for 3 times, add dichloromethane as solvent, and start stirring. Then, add β-D-glucose pentaacetate I and 4-(4-methoxyphenyl)butan-1-ol II-3 in turn. Cool reaction flask to 0±5° C., drop boron trifluoride dibutyl ether complex, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after concentrating organic phase to no obvious fraction, and obtain compound III-3, with a yield of 33%. ¹H NMR and LRMS are consistent with Example 3.

Synthesis of 1-(4-methoxy)phenylbutyl-β-D-glucopyranoside IV-3

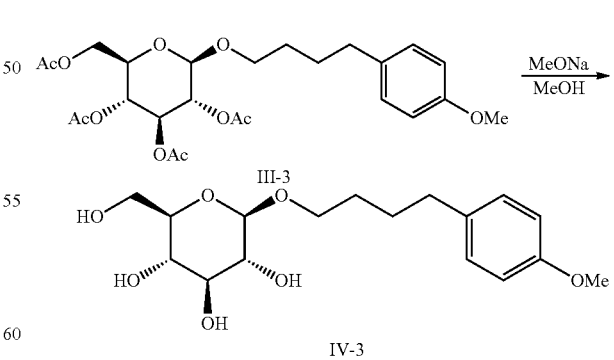

Operation steps: Replace reaction flask with nitrogen for 3 times, add methanol as solvent, and start stirring. Add intermediate III-3 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-3, with a yield of 95%. $^1$H NMR and LRMS are consistent with Example 3.

Example 9

Synthesis of 1-[4(4-methoxyphenyl)butyl]-2,3,4,6-O-tetraacetyl-β-D-glucopyranoside III-3

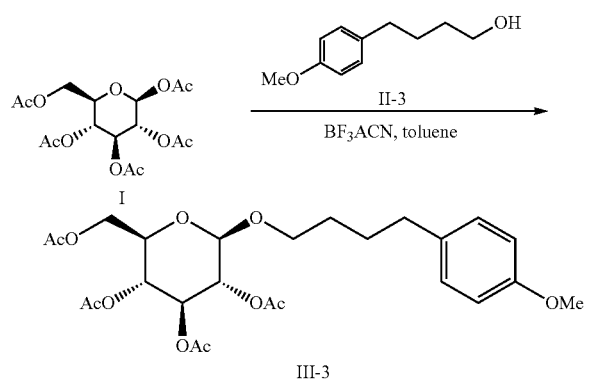

Operation steps: Replace reaction flask with nitrogen for 3 times, add toluene as solvent, and start stirring. Then, add β-D-glucose pentaacetate I and 4-(4-methoxyphenyl)butan-1-ol II-3 in turn. Cool reaction flask to 0±5° C., drop boron trifluoride acetonitrile complex, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after concentrating organic phase to no obvious fraction, and obtain compound III-3, with a yield of 36%. $^1$H NMR and LRMS are consistent with Example 3.

Synthesis of 1-(4-methoxy)phenylbutyl-β-D-glucopyranoside IV-3

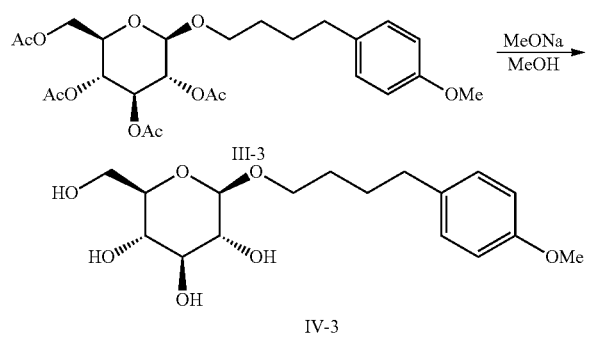

Operation steps: Replace reaction flask with nitrogen for 3 times, add methanol as solvent, and start stirring. Add intermediate III-3 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-3, with a yield of 88%. $^1$H NMR and LRMS are consistent with Example 3.

Example 10

Synthesis of 1-[4(4-methoxyphenyl)butyl]-2,3,4,6-O-tetraacetyl-β-D-glucopyranoside III-3

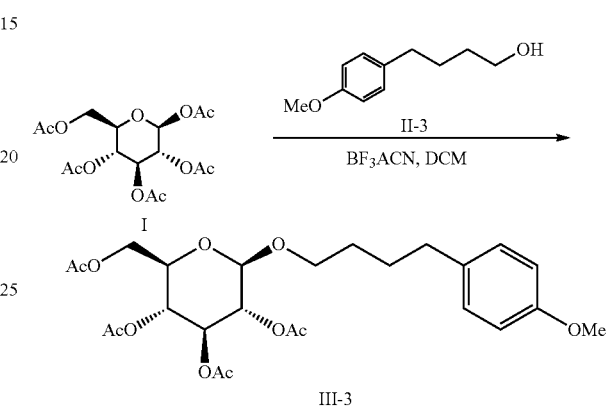

Operation steps: Replace reaction flask with nitrogen for 3 times, add dichloromethane as solvent, and start stirring. Then, add β-D-glucose pentaacetate I and 4-(4-methoxyphenyl)butan-1-ol II-3 in turn. Cool reaction flask to 0±5° C., drop boron trifluoride acetonitrile complex, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after concentrating organic phase to no obvious fraction, and obtain compound III-3, with a yield of 30%. $^1$H NMR and LRMS are consistent with Example 3.

Synthesis of 1-(4-methoxy)phenylbutyl-β-D-glucopyranoside IV-3

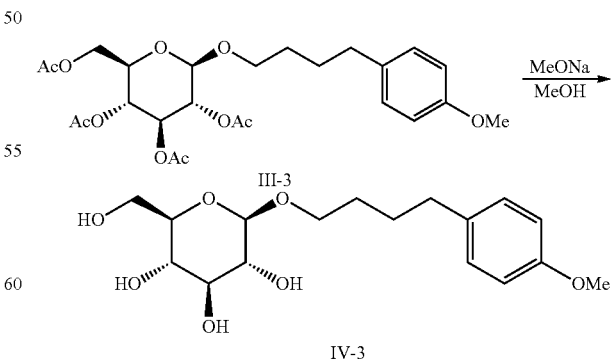

Operation steps: Replace reaction flask with nitrogen for 3 times, add methanol as solvent, and start stirring. Add intermediate III-3 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-3, with a yield of 86%. ¹H NMR and LRMS are consistent with Example 3.

Example 11

Synthesis of 1-[4(4-methoxyphenyl)butyl]-2,3,4,6-O-tetraacetyl-β-D-glucopyranoside III-3

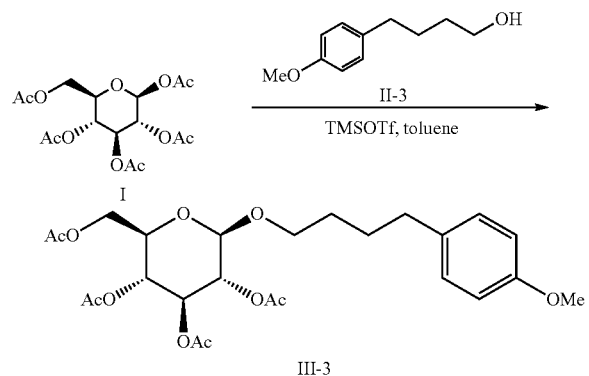

Operation steps: Replace reaction flask with nitrogen for 3 times, add toluene as solvent, and start stirring. Then, add β-D-glucose pentaacetate I and 4-(4-methoxyphenyl)butan-1-ol II-3 in turn. Cool reaction flask to 0±5° C., drop trimethylsilyl trifluoromethanesulfonate, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after concentrating organic phase to no obvious fraction, and obtain compound III-3, with a yield of 28%. H NMR and LRMS are consistent with Example 3.

Synthesis of 1-(4-methoxy)phenylbutyl-β-D-glucopyranoside IV-3

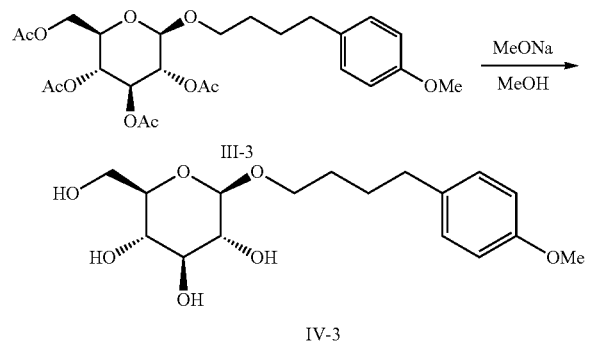

Operation steps: Replace reaction flask with nitrogen for 3 times, add methanol as solvent, and start stirring. Add intermediate III-3 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-3, with a yield of 84%. ¹H NMR and LRMS are consistent with Example 3.

Example 12

Synthesis of 1-[4(4-methoxyphenyl)butyl]-2,3,4,6-O-tetraacetyl-β-D-glucopyranoside III-3

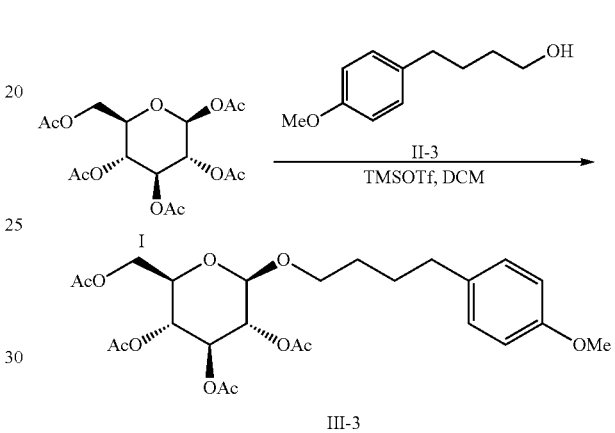

Operation steps: Replace reaction flask with nitrogen for 3 times, add dichloromethane as solvent, and start stirring. Then, add β-D-glucose pentaacetate I and 4-(4-methoxyphenyl)butan-1-ol II-3 in turn. Cool reaction flask to 0±5° C., drop trimethylsilyl trifluoromethanesulfonate, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after concentrating organic phase to no obvious fraction, and obtain compound III-3, with a yield of 26%. ¹H NMR and LRMS are consistent with Example 3.

Synthesis of 1-(4-methoxy)phenylbutyl-β-D-glucopyranoside IV-3

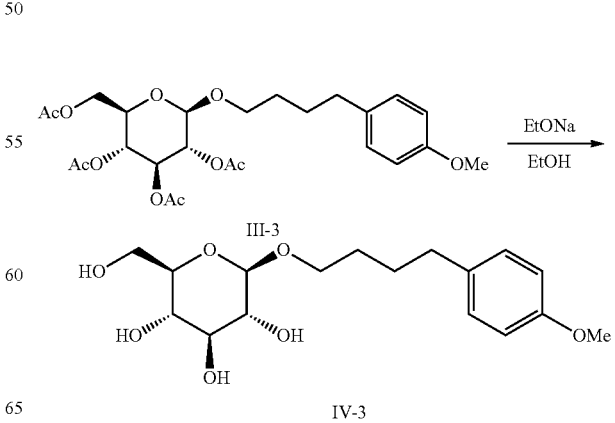

Operation steps: Replace reaction flask with nitrogen for 3 times, add ethanol as solvent, and start stirring. Add intermediate III-3 into reaction flask, control temperature at 25±5° C., add sodium ethoxide into reaction flask, and stir to react for 2 h. After reaction, conduct diatomite filtration, and collect filtrate after ethanol leaching. Add (H⁺) ion exchange resin and stir for 10 h. Filter to remove (H⁺) ion exchange resin. Conduct column chromatography isolation after organic phase concentration, and obtain final product IV-3, with a yield of 89%. ¹H NMR and LRMS are consistent with Example 3.

Example 13

Synthesis of 1-[4(4-methoxyphenyl)butyl]-2,3,4,6-O-tetraacetyl-β-D-glucopyranoside III-3

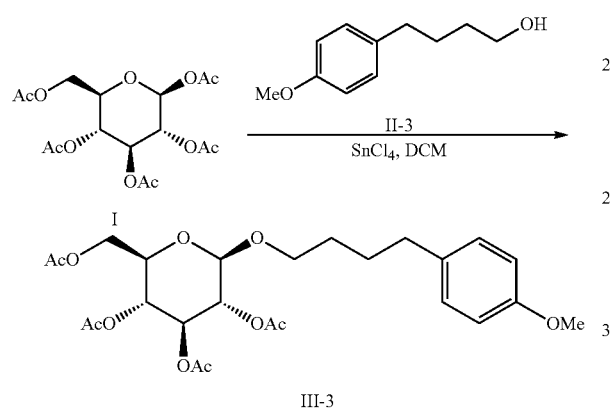

Operation steps: Replace reaction flask with nitrogen for 3 times, add dichloromethane as solvent, and start stirring. Then, add β-D-glucose pentaacetate I, tin tetrachloride and 4-(4-methoxyphenyl)butan-1-ol II-3 in turn. Cool reaction flask to 0±5° C., stir to react for 12 h. After reaction, drop water to system to quench, separate liquid, wash organic phase with Na₂CO₃ water solution, separate liquid, and wash organic phase with water once again. Collect organic phase after liquid separation. Conduct column chromatography isolation after organic phase concentration, and obtain compound III-3, with a yield of 25%. ¹H NMR and LRMS are consistent with Example 3.

Synthesis of 1-(4-methoxy)phenylbutyl-β-D-glucopyranoside IV-3

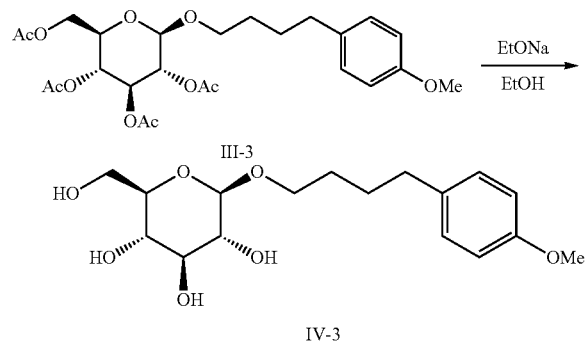

Operation steps: Replace reaction flask with nitrogen for 3 times, add ethanol as solvent, and start stirring. Add intermediate III-3 into reaction flask, control temperature at 25±5° C., add sodium ethoxide into reaction flask, and stir to react for 2 h. After reaction, conduct diatomite filtration, and collect filtrate after ethanol leaching. Add (H⁺) ion exchange resin and stir for 10 h. Filter to remove (H⁺) ion exchange resin. Conduct column chromatography isolation after organic phase concentration, and obtain final product IV-3, with a yield of 92%. ¹H NMR and LRMS are consistent with Example 3.

Example 14

Synthesis of 1-[4-(3,4-dimethoxyphenyl)butyl]-2,3,4,6-O-tetraacetyl-β-D-glucopyranoside III-4

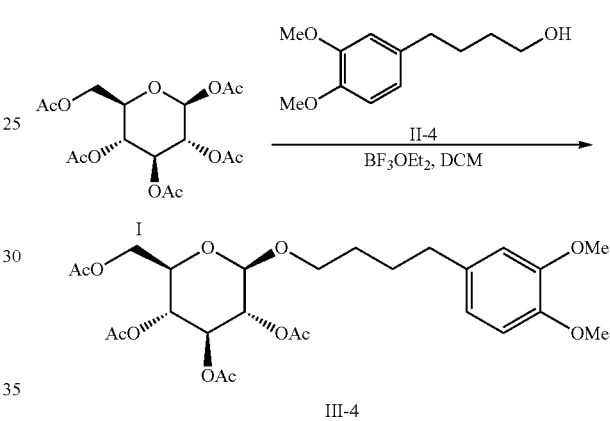

Operation steps: Replace reaction flask with nitrogen for 3 times, add dichloromethane as solvent, and start stirring. Then, add β-D-glucose pentaacetate I and 4-(3,4-dimethoxyphenyl)butan-1-ol II-4 in turn. Cool reaction flask to 0±5° C., drop boron trifluoride ether complex, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after organic phase concentration, and obtain compound III-4, with a yield of 33%. ¹H NMR (300 MHz, CDCl₃): δ 6.82-6.59 (m, 3H), 5.27-4.83 (m, 3H), 4.46 (d, J=7.9 Hz, 1H), 4.32-3.99 (m, 2H),n 3.83 (m, 7H), 3.74-3.35 (m, 2H), 2.53 (m, 2H), 1.99 (m, 12H), 1.59 (m, 4H). LRMS(ESI): [M+Na]⁺ 563.5.

Synthesis of 1-(3,4-dimethoxy)phenylbutyl-β-D-glucopyranoside IV-4

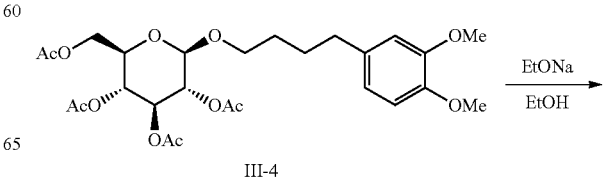

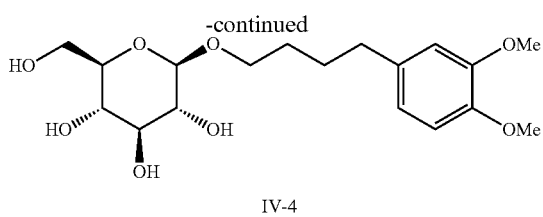

IV-4

Operation steps: Replace reaction flask with nitrogen for 3 times, add ethanol as solvent, and start stirring. Add intermediate III-4 into reaction flask, control temperature at 25±5° C., add sodium ethoxide into reaction flask, and stir to react for 2 h. After reaction, conduct diatomite filtration, and collect filtrate after ethanol leaching. Add ($H^+$) ion exchange resin and stir for 10 h. Filter to remove ($H^+$) ion exchange resin. Conduct column chromatography isolation after organic phase concentration, and obtain final product IV-4, with a yield of 85%. $^1$H NMR (400 MHz, $CD_3OD$): δ 6.84 (d, J=8.2 Hz, 1H), 6.79 (d, J=1.9 Hz, 1H), 6.72 (dd, J=8.1, 1.9 Hz, 1H), 4.24 (d, J=7.8 Hz, 1H), 3.98-3.88 (m, 1H), 3.86 (dd, J=11.9, 1.9 Hz, 1H), 3.81 (s, 3H), 3.79 (s, 1H), 3.66 (dd, J=11.9, 5.3 Hz, 1H), 3.61-3.51 (m, 1H), 3.38-3.21 (m, 3H), 3.20-3.12 (m, 1H), 2.58 (t, J=7.2 Hz, 2H), 1.75-1.56 (m, 4H). LRMS(ESI): [M+Na]$^+$ 395.1; HRMS(ESI): m/z Calcd for $C_{18}H_{32}O_8N^+$ [M+NH$_4$]$^+$: 390.2122, Found: 390.2118.

Example 15

Synthesis of 1-[4-(3,5-dimethoxyphenyl)butyl]-2,3,4,6-O-tetraacetyl-β-D-glucopyranoside III-5

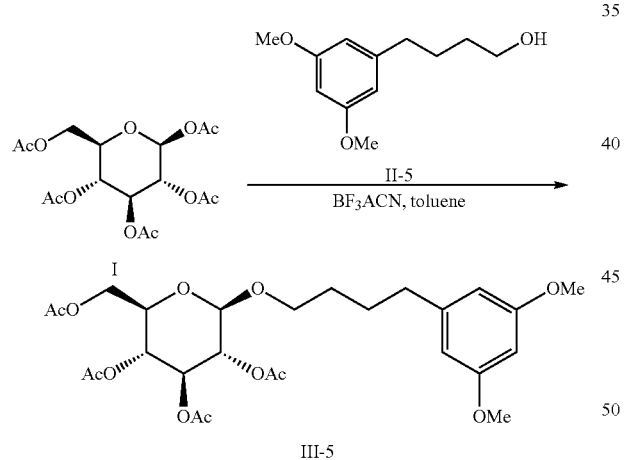

Operation steps: Replace reaction flask with nitrogen for 3 times, add toluene as solvent, and start stirring. Then, add β-D-glucose pentaacetate I and 4-(3,5-dimethoxyphenyl)butan-1-ol II-5 in turn. Cool reaction flask to 0±5° C., drop boron trifluoride acetonitrile complex, and continue to stir for 12 h after that. After reaction, drop water to system to quench, separate liquid, wash organic phase with $Na_2CO_3$ water solution, separate liquid, and wash organic phase with water once again. Collect organic phase after liquid separation. Conduct column chromatography isolation after concentrating organic phase to no obvious fraction, and obtain compound III-5, with a yield of 26%. $^1$H NMR (400 MHz, $CDCl_3$): δ 6.34-6.28 (m, 3H), 5.20 (t, J=9.5 Hz, 1H), 5.08 (t, J=9.7 Hz, 1H), 4.98 (dd, J=9.6, 8.0 Hz, 1H), 4.48 (d, J=8.0 Hz, 1H), 4.26 (dd, J=12.3, 4.7 Hz, 1H), 4.13 (dd, J=12.3, 2.3 Hz, 1H), 3.89 (d, J=9.5 Hz, 1H), 3.78 (s, 6H), 3.68 (dd, J=9.9, 2.2 Hz, 1H), 3.49 (d, J=9.4 Hz, 1H), 2.55 (t, J=6.6 Hz, 2H), 2.10-2.07 (s, 3H), 2.03 (s, 3H), 2.00 (m, 6H), 1.63 (dd, J=11.5, 4.3 Hz, 4H). LRMS(ESI): [M+Na]$^+$ 563.5.

Synthesis of 1-(3,5-dimethoxy)phenylbutyl-β-D-glucopyranoside IV-5

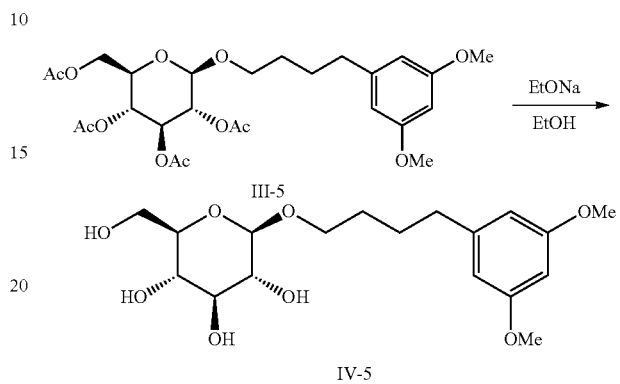

Operation steps: Replace reaction flask with nitrogen for 3 times, add ethanol as solvent, and start stirring. Add intermediate III-5 into reaction flask, control temperature at 25±5° C., add sodium ethoxide into reaction flask, and stir to react for 2 h. After reaction, conduct diatomite filtration, and collect filtrate after ethanol leaching. Add ($H^+$) ion exchange resin and stir for 10 h. Filter to remove ($H^+$) ion exchange resin. Conduct column chromatography isolation after organic phase concentration, and obtain final product IV-5, with a yield of 85%. $^1$H NMR (400 MHz, $CD_3OD$): δ 6.35 (d, J=2.2 Hz, 2H), 6.28 (t, J=2.2 Hz, 1H), 4.24 (d, J=7.8 Hz, 1H), 3.96-3.91 (m, 1H), 3.85 (dd, J=11.8, 1.7 Hz, 1H), 3.74 (s, 6H), 3.66 (dd, J=11.9, 5.2 Hz, 1H), 3.58-3.53 (m, 1H), 3.38-3.21 (m, 3H), 3.19-3.11 (m, 1H), 2.57 (t, J=7.3 Hz, 2H), 1.75-1.58 (m, 4H). LRMS(ESI): [M+Na]$^+$ 395.1; HRMS(ESI): m/z Calcd for $C_{18}H_{32}O_8N^+$: 390.2122, Found: 390.2122.

Example 16

Synthesis of 1-[4-(3,4,5-triethoxyphenyl)butyl]-2,3,4,6-O-tetraacetyl-β-D-glucopyranoside III-6

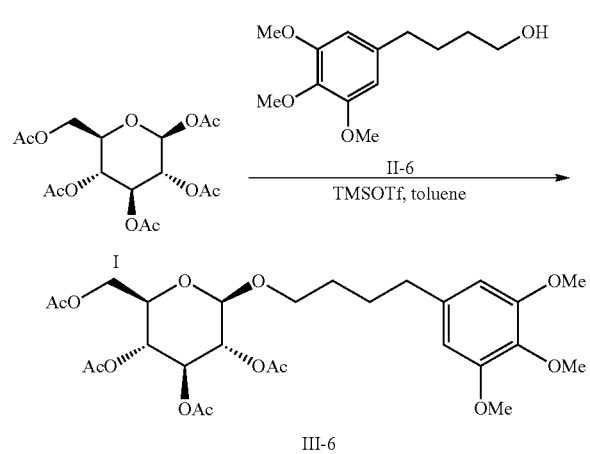

Operation steps: Replace reaction flask with nitrogen for 3 times, add toluene as solvent, and start stirring. Then, add β-D-glucose pentaacetate I and 4-(3,4,5-trimethoxyphenyl)butan-1-ol II-6 in turn. Cool reaction flask to 0±5° C., drop trifluoromethanesulfonic acid trimethylsilyl, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatographic purification after organic phase concentration, and obtain compound III-6, with a yield of 24%. LRMS(ESI): [M+Na]⁺ 593.5.

Synthesis of 1-(3,4,5-trimethoxy)phenylbutyl-β-D-glucopyranoside IV-6

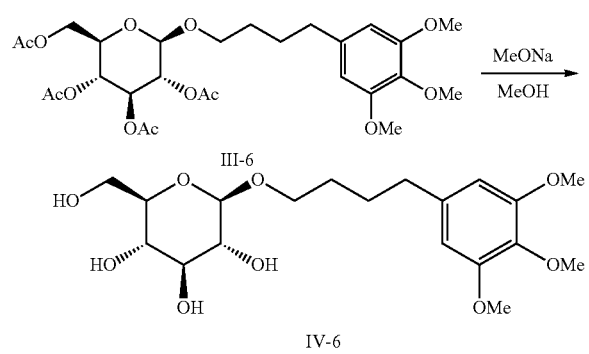

Operation steps: Replace reaction flask with nitrogen for 3 times, add methanol as solvent, and start stirring. Add intermediate III-6 (1.0 eq) into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-6, with a yield of 88%. ¹H NMR (400 MHz, CD₃OD): δ 6.49 (s, 2H), 4.24 (d, J=7.8 Hz, 1H), 3.97-3.83 (m, 2H), 3.81 (s, 6H), 3.72 (s, 3H), 3.69-3.52 (m, 2H), 3.37-3.21 (m, 3H), 3.20-3.13 (m, 1H), 2.59 (t, J=7.3 Hz, 2H), 1.79-1.55 (m, 4H). LRMS(ESI): [M+Na]⁺ 425.1; HRMS(ESI): m/z Calcd for C₁₉H₃₄O₉N+[M+NH₄]⁺: 420.2228, Found: 420.2226.

Example 17

Synthesis of 1-[5-(4-methoxyphenyl)amyl]-2,3,4,6-O-tetraacetyl-β-D-glucopyranoside III-7

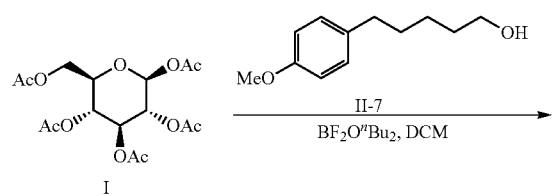

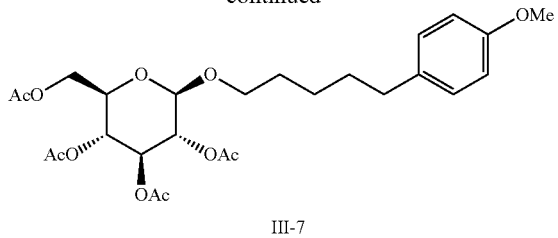

Operation steps: Replace reaction flask with nitrogen for 3 times, add dichloromethane as solvent, and start stirring. Then, add β-D-glucose pentaacetate I and 5-(4-methoxyphenyl)pentan-1-ol II-7 in turn. Cool reaction flask to 0±5° C., drop boron trifluoride dibutyl etherate, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after concentrating organic phase to no obvious fraction, and obtain compound III-7, with a yield of 22%. ¹H NMR (300 MHz, CDCl₃): δ 7.08 (d, J=6.9 Hz, 2H), 6.82 (d, J=6.8 Hz, 2H), 5.69 (d, J=4.2 Hz, 1H), 5.19 (m, 1H), 4.91 (d, J=9.3 Hz, 1H), 4.30 (m, 1H), 4.20 (m, 2H), 3.96 (m, 1H), 3.79 (s, 3H), 3.46 (t, J=5.7 Hz, 2H), 2.55 (t, J=7.0 Hz, 2H), 2.09 (m, 9H), 1.71 (s, 3H), 1.66-1.48 (m, 4H), 1.36 (d, J=6.7 Hz, 2H). LRMS (ESI): [M+Na]⁺ 547.5.

Synthesis of 1-(4-methoxy)phenylamyl-β-D-glucopyranoside IV-7

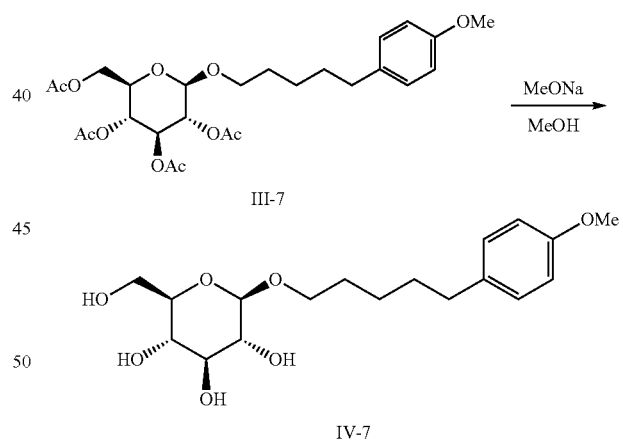

Operation steps: Replace reaction flask with nitrogen for 3 times, add methanol as solvent, and start stirring. Add intermediate III-7 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-7, with a yield of 95%. ¹H NMR (400 MHz, CD₃OD): δ 7.07 (d, J=8.8 Hz, 2H), 6.80 (d, J=8.8 Hz, 2H), 4.23 (d, J=7.8 Hz, 1H), 3.93-3.82 (m, 2H), 3.75 (s, 3H), 3.66 (dd, J=11.9, 5.3 Hz, 1H), 3.52 (dt, J=9.5, 6.7 Hz, 1H), 3.38-3.22 (m, 3H), 3.20-3.12 (m, 1H), 2.54 (t, J=7.6 Hz, 2H), 1.68-1.61 (m, 4H), 1.47-1.31 (m, 2H). LRMS(ESI): [M+Na]$^+$ 375.1; HRMS(ESI): m/z Calcd for C$_{18}$H$_{29}$O$_7{}^+$ [M+H]$^+$: 357.1908, found: 357.1906.

Example 18

Synthesis of 1-[6-(4-methoxyphenyl)hexyl]-2,3,4,6-O-tetraacetyl-β-D-glucopyranoside III-8

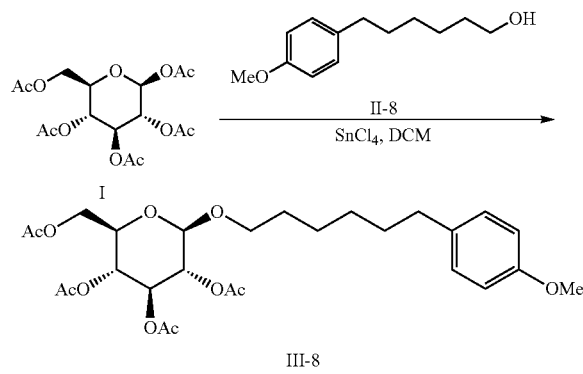

Operation steps: Replace reaction flask with nitrogen for 3 times, add dichloromethane as solvent, and start stirring. Then, add β-D-glucose pentaacetate I, tin tetrachloride and 6-(4-methoxyphenyl)hexan-1-ol II-8 in turn. Cool reaction flask to 0±5° C., stir to react for 10 h. After reaction, drop water to system to quench, separate liquid, wash organic phase with Na$_2$CO$_3$ water solution, separate liquid, and wash organic phase with water once again. Collect organic phase after liquid separation. Conduct column chromatography after organic phase concentration, and obtain compound III-8, with a yield of 18%. $^1$H NMR (400 MHz, CDCl$_3$): δ 7.08 (d, J=8.6 Hz, 2H), 6.83 (t, J=5.7 Hz, 2H), 5.20 (t, J=9.5 Hz, 1H), 5.08 (t, J=9.7 Hz, 1H), 4.98 (dd, J=9.6, 8.0 Hz, 1H), 4.48 (d, J=8.0 Hz, 1H), 4.26 (dd, J=12.3, 4.7 Hz, 1H), 4.12 (m, 1H), 3.86 (dt, J=9.6, 6.3 Hz, 1H), 3.79 (s, 3H), 3.68 (ddd, J=9.9, 4.6, 2.4 Hz, 1H), 3.46 (dt, J=9.5, 6.8 Hz, 1H), 2.58-2.49 (m, 2H), 2.08 (s, 3H), 2.02 (m, 9H), 1.62-1.49 (m, 4H), 1.36-1.28 (m, 4H). LRMS(ESI): [M+Na]$^+$ 561.5.

Synthesis of 1-(4-methoxy)phenylhexyl-β-D-glucopyranoside IV-8

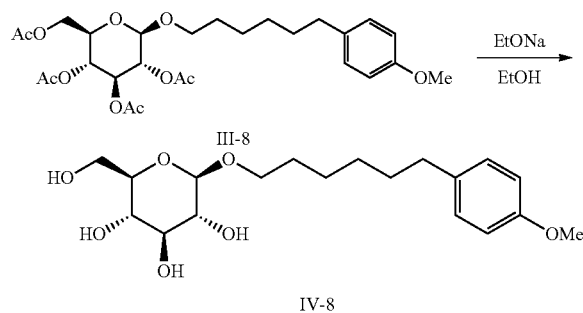

Operation steps: Replace reaction flask with nitrogen for 3 times, add ethanol as solvent, and start stirring. Add intermediate III-8 into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H$^+$) ion exchange resin. Conduct column chromatography isolation after organic phase concentration, and obtain final product IV-8, with a yield of 84%. $^1$H NMR (400 MHz, CD$_3$OD): δ 7.06 (d, J=8.6 Hz, 2H), 6.84-6.80 (d, J=8.6 Hz, 2H), 4.23 (d, J=7.8 Hz, 1H), 3.93-3.82 (m, 2H), 3.75 (s, 3H), 3.66 (dd, J=11.9, 5.2 Hz, 1H), 3.52 (dt, J=9.5, 6.7 Hz, 1H), 3.38-3.21 (m, 3H), 3.20-3.11 (m, 1H), 2.53 (t, J=7.6 Hz, 2H), 1.68-1.50 (m, 4H), 1.47-1.25 (m, 4H). LRMS(ESI): [M+Na]$^+$ 393.1; HRMS(ESI): m/z Calcd for C$_{19}$H$_{34}$O$_7$N$^+$ [M+NH$_4$]$^+$: 388.2330, found: 388.2327.

Example 19

Synthesis of 1-[4(4-fluorophenyl)butyl]-2,3,4,6-O-tetraacetyl-β-D-glucopyranoside III-9

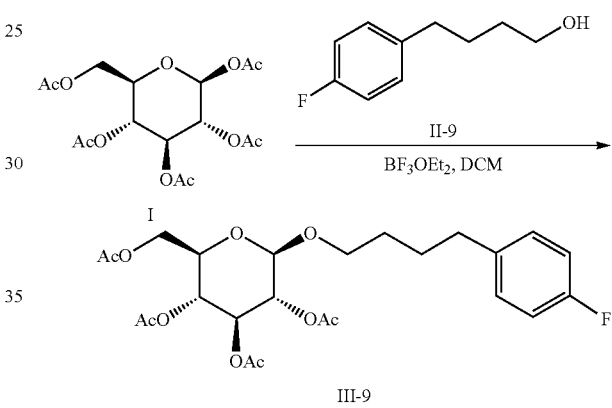

Operation steps: Replace reaction flask with nitrogen for 3 times, add dichloromethane as solvent, and start stirring. Then, add β-D-glucose pentaacetate I and 4-(4-fluorophenyl)butan-1-ol II-9 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after concentrating organic phase to no obvious fraction, and obtain compound III-9, with a yield of 22%. LRMS(ESI): [M+Na]$^+$ 521.5.

Synthesis of 1-(4-fluoro)phenylbutyl-β-D-glucopyranoside IV-9

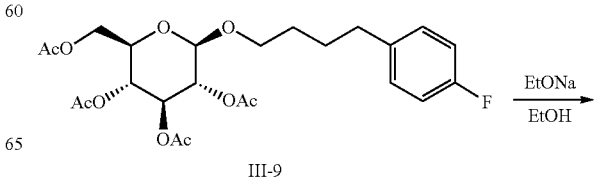

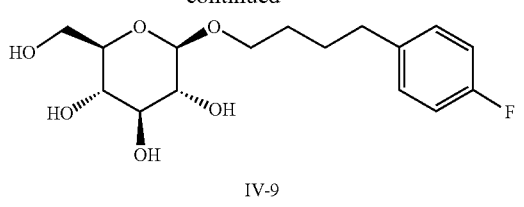

IV-9

Operation steps: Replace reaction flask with nitrogen for 3 times, add ethanol as solvent, and start stirring. Add intermediate III-9 into reaction flask, control temperature at 25±5° C., add sodium ethoxide into reaction flask, and stir to react for 2 h. After reaction, conduct diatomite filtration, and collect filtrate after ethanol leaching. Add (H⁺) ion exchange resin and stir for 10 h. Filter to remove (H⁺) ion exchange resin. Conduct column chromatography isolation after organic phase concentration, and obtain final product IV-9, with a yield of 93%. $^1$H NMR (400 MHz, CD$_3$OD): δ 7.18 (dd, J=8.5, 5.6 Hz, 2H), 7.00-6.91 (m, 2H), 4.24 (d, J=7.8 Hz, 1H), 3.92 (dt, J=9.6, 6.3 Hz, 1H), 3.87-3.82 (m, 1H), 3.66 (dd, J=11.8, 5.2 Hz, 1H), 3.56 (dt, J=9.5, 6.3 Hz, 1H), 3.37 3.22 (m, 3H), 3.20-3.11 (m, 1H), 2.62 (t, J=7.3 Hz, 2H), 1.78-1.54 (m, 4H). LRMS(ESI): [M+COOH]⁻ 375.0; HRMS(ESI): m/z Calcd for C$_{16}$H$_{23}$O$_6$FCl⁻ [M+Cl]⁻ : 365.1173, Found: 365.1173.

Example 20

Synthesis of 1-[4(4-bromophenyl)butyl]-2,3,4,6-O-tetraacetyl-β-D-glucopyranoside III-10

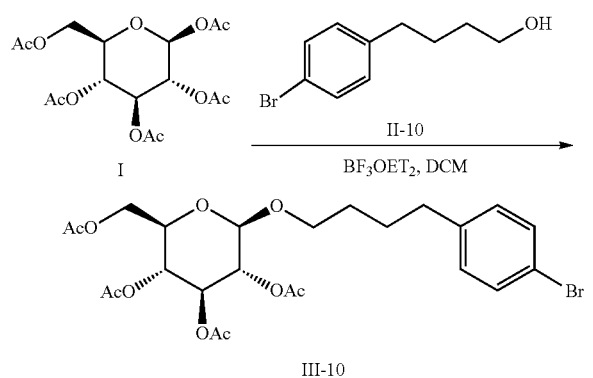

Operation steps: Replace reaction flask with nitrogen for 3 times, add dichloromethane as solvent, and start stirring. Then, add β-D-glucose pentaacetate I and 4-(4-bromophenyl)butan-1-ol II-10 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after concentrating organic phase to no obvious fraction, and obtain compound III-10, with a yield of 18%. LRMS(ESI): [M+Na]⁺ 582.4.

Synthesis of 1-(4-bromo)phenylbutyl-β-D-glucopyranoside IV-10

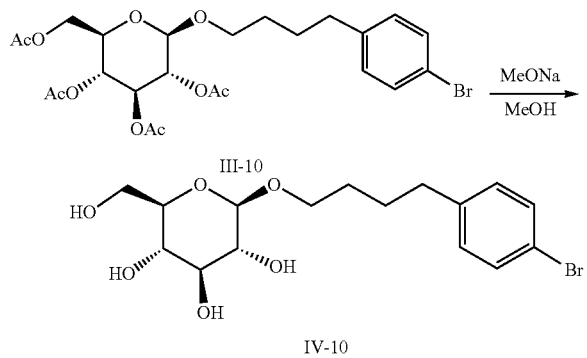

IV-10

Operation steps: Replace reaction flask with nitrogen for 3 times, add methanol as solvent, and start stirring. Add intermediate III-10 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) ion exchange resin. Conduct column chromatography isolation after organic phase concentration, and obtain final product IV-10, with a yield of 83%. $^1$H NMR (400 MHz, CD$_3$OD): δ 7.38 (d, J=8.3 Hz, 2H), 7.12 (d, J=8.3 Hz, 2H), 4.24 (d, J=7.8 Hz, 1H), 3.92 (dt, J=9.5, 6.4 Hz, 1H), 3.85 (dd, J=11.9, 1.6 Hz, 1H), 3.66 (dd, J=11.8, 5.2 Hz, 1H), 3.56 (dt, J=9.6, 6.3 Hz, 1H), 3.31 (m, 3H), 3.19-3.11 (m, 1H), 2.61 (t, J=7.4 Hz, 2H), 1.77-1.55 (m, 4H). LRMS(ESI): [M+Na]⁺ 414.9; HRMS(ESI): m/z Calcd for C$_{16}$H$_{23}$O$_6$BrNa⁺ [M+Na]⁺: 413.0570, Found: 413.0568.

Example 21

Synthesis of 1-[4(4-nitrophenyl)butyl]-2,3,4,6-O-tetraacetyl-β-D-glucopyranoside III-11

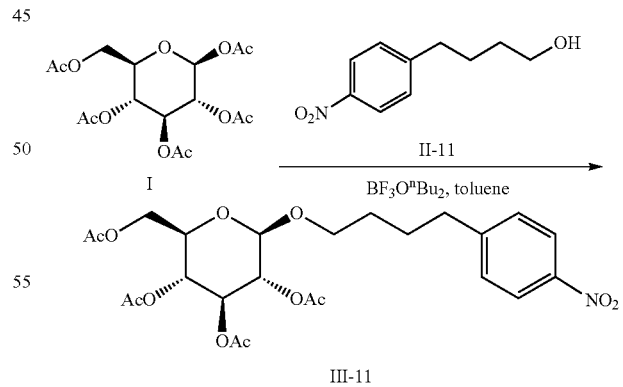

III-11

Operation steps: Replace reaction flask with nitrogen for 3 times, add toluene as solvent, and start stirring. Then, add β-D-glucose pentaacetate I and 4-(4-nitrophenyl)butan-1-ol II-11 in turn. Cool reaction flask to 0±5° C., drop boron trifluoride dibutyl ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatographic purification after organic phase concentration, and obtain compound III-11, with a yield of 27%. LRMS(ESI): [M+Na]$^+$ 548.5.

Synthesis of 1-(4-nitro)phenylbutyl-β-D-glucopyranoside IV-11

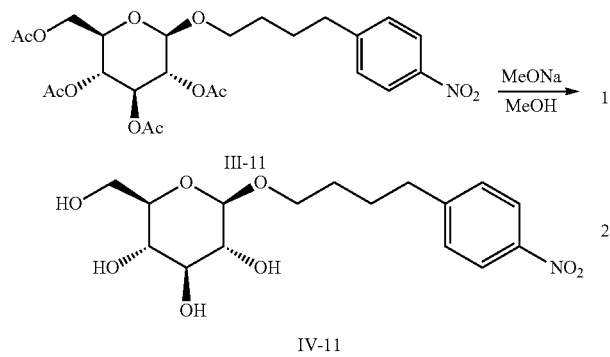

Operation steps: Replace reaction flask with nitrogen for 3 times, add methanol as solvent, and start stirring. Add intermediate III-11 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-11, with a yield of 89%. $^1$H NMR (400 MHz, CD$_3$OD): δ 8.14 (d, J=8.7 Hz, 2H), 7.45 (d, J=8.7 Hz, 2H), 4.25 (d, J=7.8 Hz, 1H), 4.00-3.82 (m, 2H), 3.70-3.50 (m, 2H), 3.37-3.22 (m, 3H), 3.21-3.12 (m, 1H), 2.78 (t, J=7.6 Hz, 2H), 1.85-1.57 (m, 4H). LRMS(ESI): [M+Na]$^+$ 380.0; HRMS(ESI): m/z Calcd for C$_{16}$H$_{23}$O$_8$NNa$^+$ [M+Na]$^+$: 380.1327, Found: 380.1314.

Example 22

Synthesis of 1-[4(4-hydroxyphenyl)butyl]-2,3,4,6-O-tetraacetyl-β-D-glucopyranoside III-12

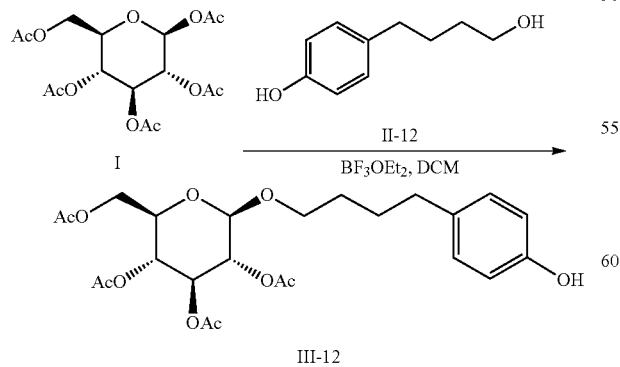

Operation steps: Replace reaction flask with nitrogen for 3 times, add dichloromethane as solvent, and start stirring. Then, add β-D-glucose pentaacetate I and 4-(4-hydroxybutyl)phenol II-12 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-12, with a yield of 22%. LRMS(ESI): [M+Na]$^+$519.2.

Synthesis of 1-(4-hydroxyl)phenylbutyl-β-D-glucopyranoside IV-12

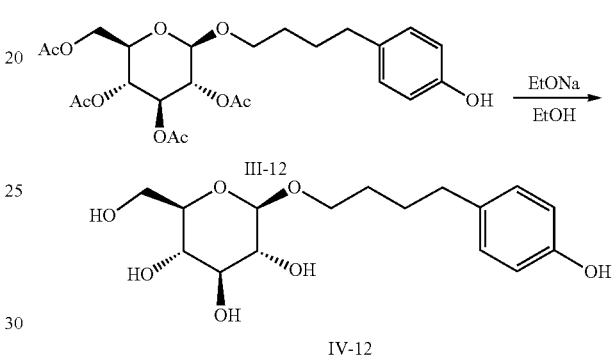

Operation steps: Replace reaction flask with nitrogen for 3 times, add ethanol as solvent, and start stirring. Add intermediate III-12 into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H$^+$) ion exchange resin. Conduct column chromatography isolation after organic phase concentration, and obtain final product IV-12, with a yield of 79%. $^1$H NMR (400 MHz, CD$_3$OD): δ 6.99 (d, J=8.5 Hz, 2H), 6.70-6.63 (m, 2H), 4.23 (d, J=7.8 Hz, 1H), 3.96-3.82 (m, 2H), 3.66 (dd, J=11.9, 5.2 Hz, 1H), 3.54 (dt, J=9.5, 6.1 Hz, 1H), 3.38-3.21 (m, 3H), 3.16 (dd, 1H), 2.53 (t, J=7.0 Hz, 2H), 1.70-1.56 (m, 4H). LRMS(ESI): [M+Na]$^+$ 351.1; HRMS(ESI): m/z Calcd for C$_{16}$H$_{28}$O$_7$N$^+$ [M+NH$_4$]$^+$: 346.1860, Found: 346.1857.

Example 23

Synthesis of 1-[4(4-hydroxyl-3-methoxyphenyl)butyl]-2,3,4,6-O-tetraacetyl-β-D-glucopyranoside III-13

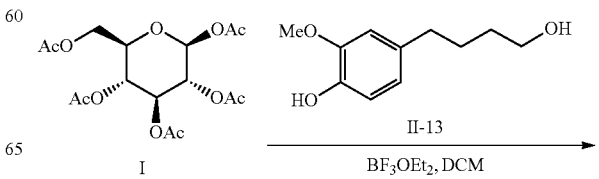

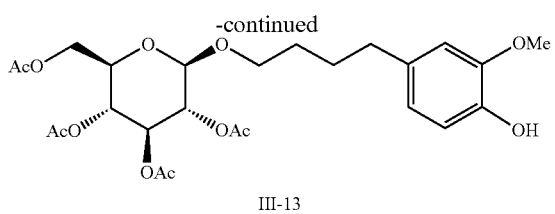

III-13

Operation steps: Replace reaction flask with nitrogen for 3 times, add dichloromethane as solvent, and start stirring. Then, add β-D-glucose pentaacetate I and 4-(4-hydroxybutyl)-2-methoxyphenol II-13 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatographic purification after organic phase concentration, and obtain compound III-13, with a yield of 19%. LRMS(ESI): [M−H]$^-$ 525.2.

Synthesis of 1-(4-hydroxyl-3-methoxy)phenylbutyl-β-D-glucopyranoside IV-13

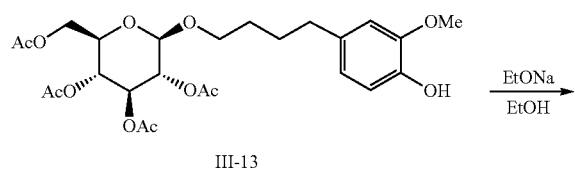

Operation steps: Replace reaction flask with nitrogen for 3 times, add ethanol as solvent, and start stirring. Add intermediate III-13 into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H$^+$) ion exchange resin. Conduct column chromatography isolation after organic phase concentration, and obtain final product IV-13, with a yield of 80%. $^1$H NMR (400 MHz, CDCl$_3$): δ 6.83 (d, J=7.6 Hz, 1H), 6.70-6.64 (m, 2H), 6.26 (br, 1H), 4.83 (br, 8H), 4.00 (s, 1H), 3.88 (s, 3H), 3.74 (t, J=6.4 Hz, 2H), 3.55 (s, 2H), 2.58 (t, J=7.2 Hz, 2H), 1.69-1.62 (m, 4H). LRMS(ESI): [M+Na]$^+$ 381.2.

Example 24

Synthesis of 1-[4-(3,4-methylenedioxyphenyl)butyl]-2,3,4,6-O-tetraacetyl-β-D-glucopyranoside III-14

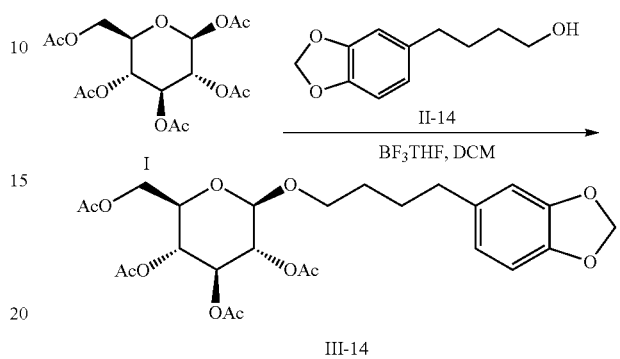

Operation steps: Replace reaction flask with nitrogen for 3 times, add dichloromethane as solvent, and start stirring. Then, add β-D-glucose pentaacetate I and 4-(benzo[d][1,3]dioxol-5-yl)butan-1-ol II-14 in turn. Cool reaction flask to 0±5° C., drop boron trifluoride tetrahydrofuran complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after concentrating organic phase to no obvious fraction, and obtain compound III-14, with a yield of 27%. LRMS(ESI): [M+Na]$^+$ 547.5.

Synthesis of 1-(3,4-methylenedioxy)phenylbutyl-β-D-glucopyranoside IV-14

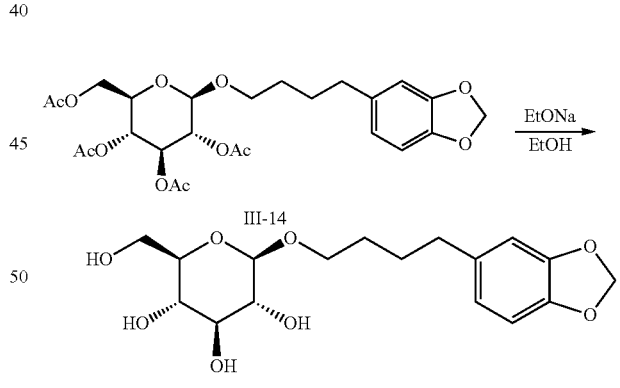

Operation steps: Replace reaction flask with nitrogen for 3 times, add ethanol as solvent, and start stirring. Add intermediate III-14 into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H$^+$) ion exchange resin. Conduct column chromatography isolation after organic phase concentration, and obtain final product IV-14, with a yield of 82%. $^1$H NMR (400 MHz, CD$_3$OD): δ 6.71-6.67 (m, 2H), 6.65-6.61 (m, 1H), 5.87 (s, 2H), 4.23

(d, J=7.8 Hz, 1H), 3.95-3.88 (m, 1H), 3.85 (m, 1H), 3.66 (dd, J=11.8, 5.2 Hz, 1H), 3.60-3.48 (m, 1H), 3.38-3.20 (m, 3H), 3.19-3.12 (m, 1H), 2.55 (t, J=7.1 Hz, 2H), 1.73-1.53 (m, 4H). LRMS(ESI): [M+Na]$^+$ 379.0; HRMS(ESI): m/z Calcd for $C_{17}H_{24}O_8Na^+$ [M+Na]$^+$ : 379.1374, Found: 379.1362.

Example 25

Synthesis of 1-[4(4-ethoxyphenyl)butyl]-2,3,4,6-O-tetraacetyl-β-D-glucopyranoside III-15

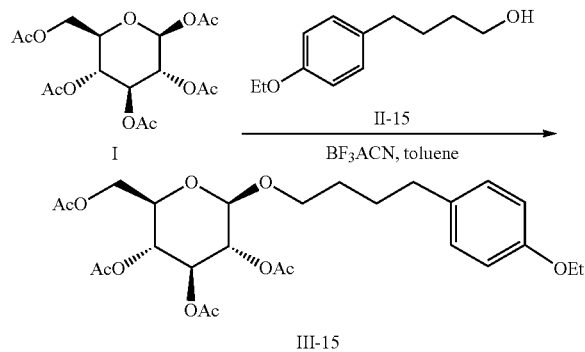

Operation steps: Replace reaction flask with nitrogen for 3 times, add toluene as solvent, and start stirring.

Then, add β-D-glucose pentaacetate I and 4-(4-ethoxyphenyl)butan-1-ol II-15 in turn. Cool reaction flask to 0±5° C., drop boron trifluoride acetonitrile complex, and continue to stir for 12 h after that. After reaction, drop water to system to quench, separate liquid, wash organic phase with $Na_2CO_3$ water solution, separate liquid, and wash organic phase with water once again. Collect organic phase after liquid separation. Conduct column chromatography isolation after concentrating organic phase to no obvious fraction, and obtain compound III-15, with a yield of 26%. LRMS(ESI): [M+Na]$^+$ 547.2.

Synthesis of 1-(4-ethoxy)phenylbutyl-β-D-glucopyranoside IV-15

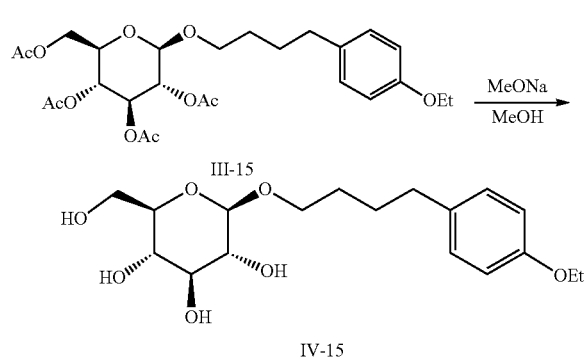

Operation steps: Replace reaction flask with nitrogen for 3 times, add methanol as solvent, and start stirring. Add intermediate III-15 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-15, with a yield of 92%. $^1$H NMR (400 MHz, CD$_3$OD): δ 7.10 (d, J=8.5 Hz, 2H), 6.82 (d, J=8.6 Hz, 2H), 4.27 (d, J=7.8 Hz, 1H), 4.02 (q, J=7.0 Hz, 2H), 3.98-3.92 (m, 1H), 3.89 (dd, J=11.8, 1.6 Hz, 1H), 3.69 (dd, J=11.8, 5.2 Hz, 1H), 3.58 (dt, J=9.5, 6.2 Hz, 1H), 3.41-3.29 (m, 3H), 3.23-3.13 (m, 1H), 2.59 (t, J=7.1 Hz, 2H), 1.78-1.56 (m, 4H), 1.39 (t, J=7.0 Hz, 3H). LRMS(ESI): [M+Na]$^+$ 379.1.

Example 26

Synthesis of 1-[4(4-n-propoxyphenyl)butyl]-2,3,4,6-O-tetraacetyl-β-D-glucopyranoside III-16

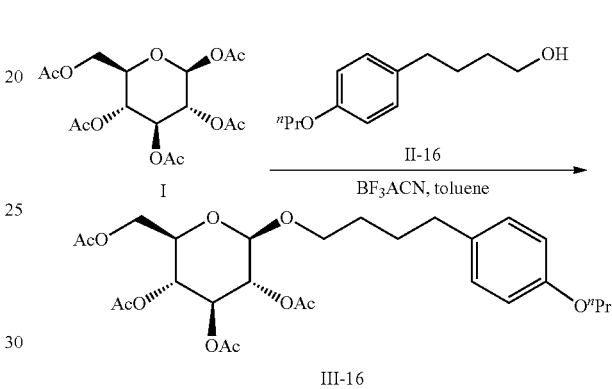

Operation steps: Replace reaction flask with nitrogen for 3 times, add toluene as solvent, and start stirring. Then, add β-D-glucose pentaacetate I and 4-(4-n-propoxyphenyl)butan-1-ol II-16 in turn. Cool reaction flask to 0±5° C., drop boron trifluoride acetonitrile complex, and continue to stir for 12 h after that. After reaction, drop water to system to quench, separate liquid, wash organic phase with $Na_2CO_3$ water solution, separate liquid, and wash organic phase with water once again. Collect organic phase after liquid separation. Conduct column chromatography isolation after concentrating organic phase to no obvious fraction, and obtain compound III-16, with a yield of 33%. LRMS(ESI): [M+Na]$^+$ 561.5.

Synthesis of 1-(4-propoxy)phenylbutyl-β-D-glucopyranoside IV-16

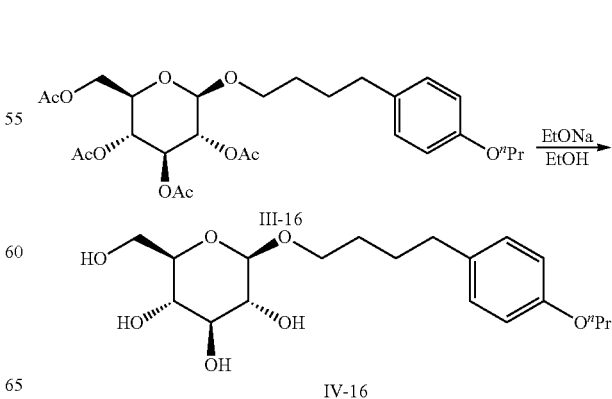

Operation steps: Replace reaction flask with nitrogen for 3 times, add ethanol as solvent, and start stirring. Add intermediate III-16 into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H$^+$) ion exchange resin. Conduct column chromatography isolation after organic phase concentration, and obtain final product IV-16, with a yield of 94%. $^1$H NMR (400 MHz, CD$_3$OD): δ 7.07 (d, J=8.5 Hz, 2H), 6.79 (d, J=8.6 Hz, 2H), 4.23 (d, J=7.8 Hz, 1H), 3.96-3.80 (m, 4H), 3.66 (dd, J=11.9, 5.2 Hz, 1H), 3.59-3.49 (m, 1H), 3.38-3.21 (m, 3H), 3.20-3.11 (m, 1H), 2.56 (t, J=7.1 Hz, 2H), 1.75 (m, 2H), 1.70-1.57 (m, 4H), 1.02 (t, J=7.4 Hz, 3H). LRMS(ESI): [M+Na]$^+$ 393.1; HRMS (ESI): m/z Calcd for C$_{19}$H$_{30}$O$_7$Na$^+$ [M+Na]$^+$: 393.1884, Found: 393.1880.

Example 27

Synthesis of 1-[4(4-isopropoxyphenyl)butyl]-2,3,4,6-O-tetraacetyl-β-D-glucopyranoside III-17

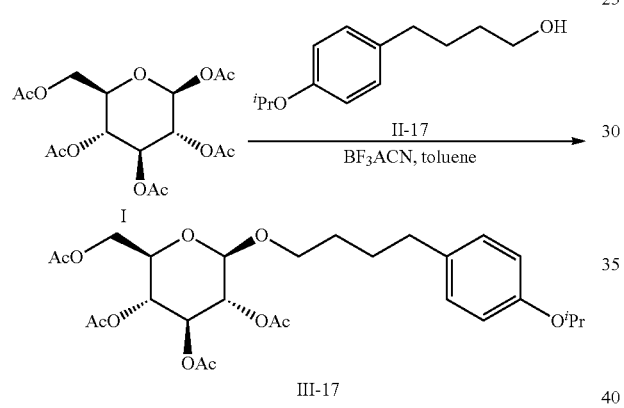

Operation steps: Replace reaction flask with nitrogen for 3 times, add toluene as solvent, and start stirring. Then, add β-D-glucose pentaacetate I and 4-(4-isopropoxyphenyl)butan-1-ol II-17 in turn. Cool reaction flask to 0±5° C., drop boron trifluoride acetonitrile complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after concentrating organic phase to no obvious fraction, and obtain compound III-17, with a yield of 35%. LRMS(ESI): [M+Na]$^+$ 561.2.

Synthesis of 1-(4-isopropoxy)phenylbutyl-β-D-glucopyranoside IV-17

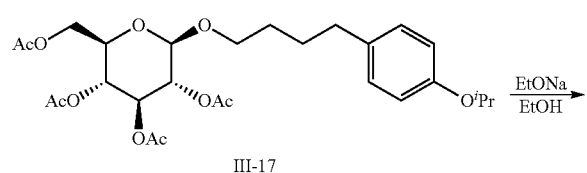

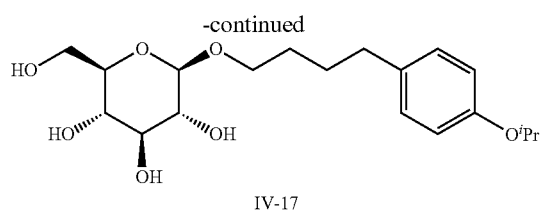

Operation steps: Replace reaction flask with nitrogen for 3 times, add ethanol as solvent, and start stirring. Add intermediate III-17 into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H$^+$) ion exchange resin. Conduct column chromatography isolation after organic phase concentration, and obtain final product IV-17, with a yield of 88%. $^1$H NMR (400 MHz, CD$_3$OD): δ 7.07 (d, J=8.6 Hz, 2H), 6.89-6.70 (m, 2H), 4.52 (dt, J=12.1, 6.1 Hz, 1H), 4.23 (d, J=7.8 Hz, 1H), 3.95-3.88 (m, 1H), 3.85 (dd, J=11.9, 1.9 Hz, 1H), 3.66 (dd, J=11.8, 5.3 Hz, 1H), 3.62-3.51 (m, 1H), 3.36-3.33 (m, 1H), 3.28-3.20 (m, 2H), 3.17 (dd, J=15.1, 7.2 Hz, 1H), 2.56 (t, J=7.1 Hz, 2H), 1.75-1.54 (m, 4H), 1.27 (d, J=6.0 Hz, 6H). LRMS(ESI): [M+Na]$^+$ 393.0; HRMS(ESI): m/z Calcd for C$_{19}$H$_{30}$O$_7$Na$^+$ [M+Na]$^+$: 393.1884, Found: 393.1880.

Example 28

Synthesis of 1-[4(4-allyloxyphenyl)butyl]-2,3,4,6-O-tetraacetyl-β-D-glucopyranoside III-18

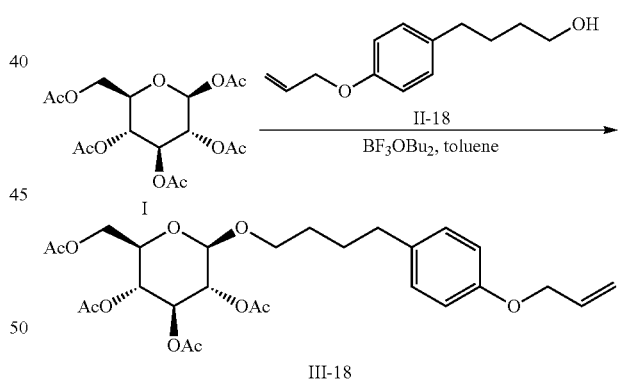

Operation steps: Replace reaction flask with nitrogen for 3 times, add toluene as solvent, and start stirring. Then, add β-D-glucose pentaacetate I and 4-(4-(allyloxy)phenyl)butan-1-ol II-18 in turn. Cool reaction flask to 0±5° C., drop boron trifluoride dibutyl etherate, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after concentrating organic phase to no obvious fraction, and obtain compound III-18, with a yield of 18%. LRMS(ESI): [M+Na]$^+$ 559.5.

Synthesis of 1-(4-allyloxy)phenylbutyl-β-D-glucopyranoside IV-18

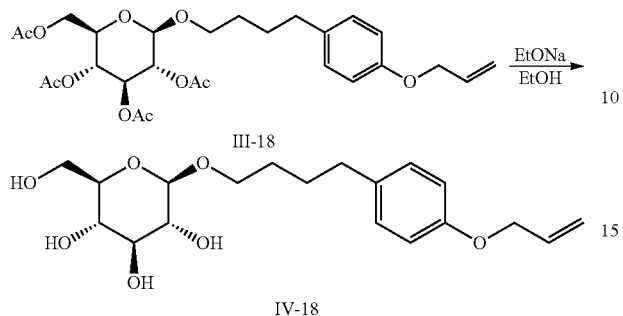

Operation steps: Replace reaction flask with nitrogen for 3 times, add ethanol as solvent, and start stirring. Add intermediate III-18 into reaction flask, control temperature at 25±5° C., add sodium ethoxide into reaction flask, and stir to react for 2 h. After reaction, conduct diatomite filtration, and collect filtrate after ethanol leaching. Add ($H^+$) ion exchange resin and stir for 10 h. Filter to remove ($H^+$) ion exchange resin. Conduct column chromatography isolation after organic phase concentration, and obtain final product IV-18, with a yield of 81%. $^1$H NMR (400 MHz, CD$_3$OD): δ 7.08 (d, J=8.6 Hz, 2H), 6.82 (d, J=8.6 Hz, 2H), 6.12-5.96 (m, 1H), 5.37 (dd, J=17.3, 1.6 Hz, 1H), 5.22 (dd, J=10.6, 1.4 Hz, 1H), 4.55-4.44 (m, 2H), 4.23 (d, J=7.8 Hz, 1H), 3.97-3.80 (m, 2H), 3.66 (dd, J=11.9, 5.2 Hz, 1H), 3.60-3.50 (m, 1H), 3.38-3.21 (m, 3H), 3.20-3.12 (m, 1H), 2.56 (t, J=7.1 Hz, 2H), 1.73-1.55 (m, 4H). LRMS(ESI): [M+Na]$^+$ 391.0; HRMS(ESI): m/z Calcd for C$_{19}$H$_{28}$O$_7$Na$^+$ [M+Na]$^+$: 391.1727, Found: 391.1726.

Example 29

Synthesis of 1-[4(4-cyclopropylmethoxyphenyl) butyl]-2,3,4,6-O-tetraacetyl-β-D-glucopyranoside III-19

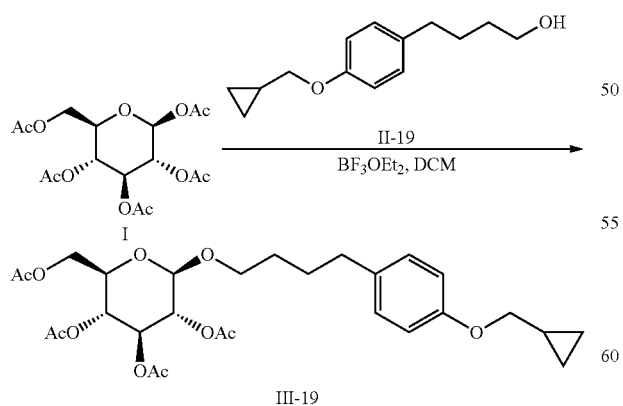

Operation steps: Replace reaction flask with nitrogen for 3 times, add dichloromethane as solvent, and start stirring. Then, add β-D-glucose pentaacetate I and 4-(4-(cyclopropylmethoxy)phenyl)butan-1-ol II-19 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-19, with a yield of 18%. LRMS(ESI): [M+Na]$^+$ 573.2.

Synthesis of 1-(4-cyclopropylmethoxy)phenylbutyl-β-D-glucopyranoside IV-19

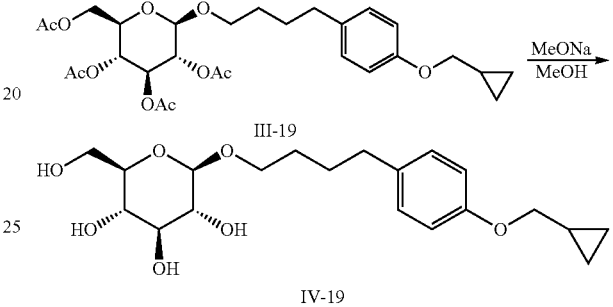

Operation steps: Replace reaction flask with nitrogen for 3 times, add methanol as solvent, and start stirring. Add intermediate III-19 into reaction flask, control temperature at 25±5° C., add sodium methoxide into reaction flask, and stir to react for 2 h. After reaction, conduct diatomite filtration, and collect filtrate after methanol leaching. Add ($H^+$) ion exchange resin and stir for 10 h. Filter to remove ($H^+$) ion exchange resin. Conduct column chromatography isolation after organic phase concentration, and obtain final product IV-19, with a yield of 78%. $^1$H NMR (400 MHz, CD$_3$OD): δ 7.07 (d, J=8.6 Hz, 2H), 6.79 (d, J=8.6 Hz, 2H), 4.23 (d, J=7.8 Hz, 1H), 3.91 (m, 1H), 3.88-3.82 (m, 1H), 3.77 (d, J=6.8 Hz, 2H), 3.67 (dd, J=12.0, 5.3 Hz, 1H), 3.55 (m, 1H), 3.33-3.17 (m, 4H), 2.56 (t, J=7.1 Hz, 2H), 1.76-1.54 (m, 4H), 1.27-1.16 (m, 1H), 0.59 (dd, J=8.1, 1.4 Hz, 2H), 0.38-0.24 (m, 2H). LRMS(ESI): [M+Na]$^+$ 405.0; HRMS(ESI): m/z Calcd for C$_{20}$H$_{30}$O$_7$Na$^+$ [M+Na]$^+$: 405.1884, Found: 405.1883.

Example 30

Synthesis of 1-[4(4-cyclobutylmethoxyphenyl) butyl]-2,3,4,6-O-tetraacetyl-β-D-glucopyranoside III-20

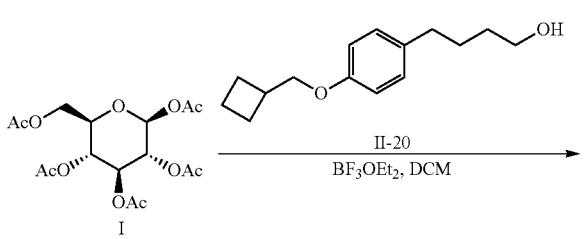

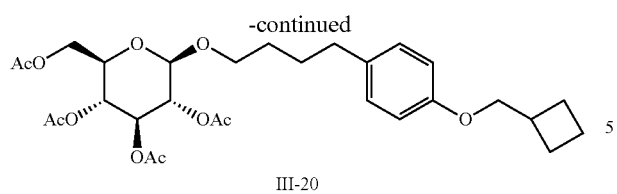

III-20

Operation steps: Replace reaction flask with nitrogen for 3 times, add dichloromethane as solvent, and start stirring. Then, add β-D-glucose pentaacetate I and 4-(4-(cyclobutyl-methoxy)phenyl)butan-1-ol II-20 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-20, with a yield of 25%. LRMS(ESI): [M+Na]$^+$ 587.6.

Synthesis of 1-(4-cyclobutylmethoxy)phenylbutyl-β-D-glucopyranoside IV-20

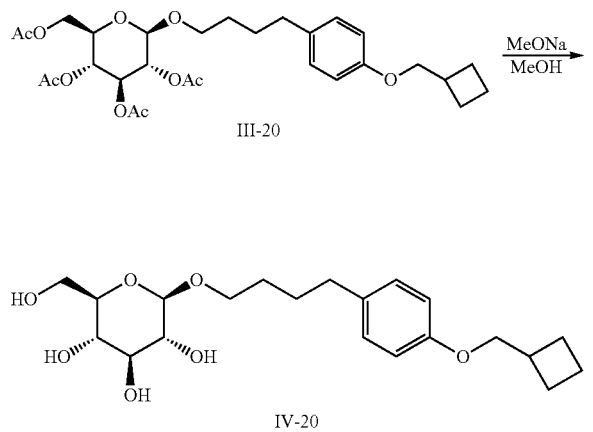

IV-20

Operation steps: Replace reaction flask with nitrogen for 3 times, add methanol as solvent, and start stirring. Add intermediate III-20 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-20, with a yield of 77%. $^1$H NMR (400 MHz, CD$_3$OD): δ 7.10 (d, J=8.5 Hz, 2H), 6.83 (d, J=8.5 Hz, 2H), 4.27 (d, J=7.8 Hz, 1H), 3.99-3.85 (m, 4H), 3.69 (dd, J=11.8, 5.2 Hz, 1H), 3.58 (dt, J=9.4, 6.2 Hz, 1H), 3.41-3.24 (m, 3H), 3.19 (t, J=8.4 Hz, 1H), 2.85-2.71 (m, 1H), 2.59 (t, J=7.1 Hz, 2H), 2.24-2.08 (m, 2H), 2.08-1.85 (m, 4H), 1.70 (m, 4H). LRMS (ESI): [M+Na]$^+$ 419.2.

Example 31

Synthesis of 1-[4(4-cyclopentylmethoxyphenyl)butyl]-2,3,4,6-O-tetraacetyl-β-D-glucopyranoside III-21

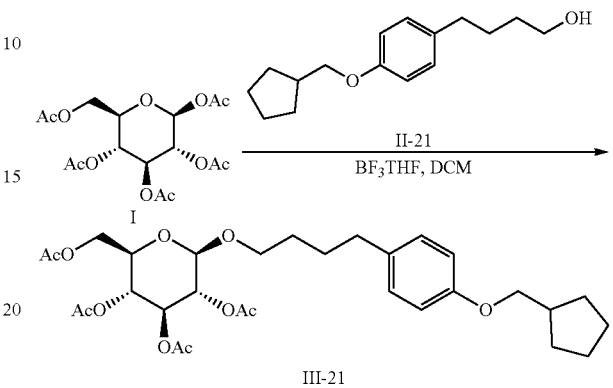

Operation steps: Replace reaction flask with nitrogen for 3 times, add dichloromethane as solvent, and start stirring. Then, add β-D-glucose pentaacetate I and 4-(4-(cyclopentylmethoxy)phenyl)butan-1-ol II-21 in turn. Cool reaction flask to 0±5° C., drop boron trifluoride tetrahydrofuran complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-21, with a yield of 19%. LRMS(ESI): [M+Na]$^+$ 601.6.

Synthesis of 1-(4-cyclopentylmethoxy)phenylbutyl-β-D-glucopyranoside IV-21

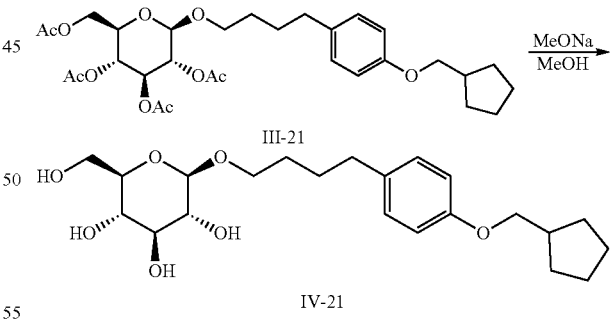

IV-21

Operation steps: Replace reaction flask with nitrogen for 3 times, add methanol as solvent, and start stirring. Add intermediate III-21 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-21, with a yield of 87%. $^1$H NMR (400 MHz, CD$_3$OD): δ 7.10 (d, J=8.5 Hz, 2H), 6.82 (d, J=8.6 Hz, 2H), 4.27 (d, J=7.8 Hz, 1H), 3.99-3.86 (m, 2H), 3.83 (d, J=6.9 Hz, 2H), 3.69 (dd, J=11.8, 5.2 Hz, 1H), 3.62-3.54 (m, 1H), 3.41-3.24 (m, 3H), 3.21-3.17 (m, 1H), 2.59 (t, J=7.0 Hz, 2H), 2.40-2.30 (m, 1H), 1.93-1.78 (m, 2H), 1.76-1.57 (m, 8H), 1.47-1.35 (m, 2H). LRMS(ESI): [M+Na]+ 433.2; HRMS(ESI): m/z Calcd for $C_{22}H_{34}O_7Na^+$ [M+Na]+: 433.2197, Found: 433.2192.

Example 32

Synthesis of 1-[4(4-cyclohexylmethoxyphenyl)butyl]-2,3,4,6-O-tetraacetyl-β-D-glucopyranoside III-22

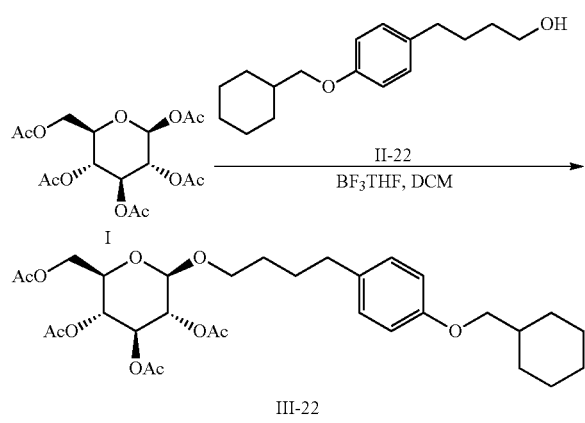

Operation steps: Replace reaction flask with nitrogen for 3 times, add dichloromethane as solvent, and start stirring. Then, add β-D-glucose pentaacetate I and 4-(4-(cyclohexylmethoxy)phenyl)butan-1-ol II-22 in turn. Cool reaction flask to 0±5° C., drop boron trifluoride tetrahydrofuran complex, and continue to stir for 12 h after that. After reaction, drop water to system to quench, separate liquid, wash organic phase with $Na_2CO_3$ water solution, separate liquid, and wash organic phase with water once again. Collect organic phase after liquid separation. Conduct column chromatography isolation after organic phase concentration, and obtain compound III-22, with a yield of 25%. LRMS(ESI): [M+Na]+ 615.6.

Synthesis of 1-(4-cyclohexylmethoxy)phenylbutyl-β-D-glucopyranoside IV-22

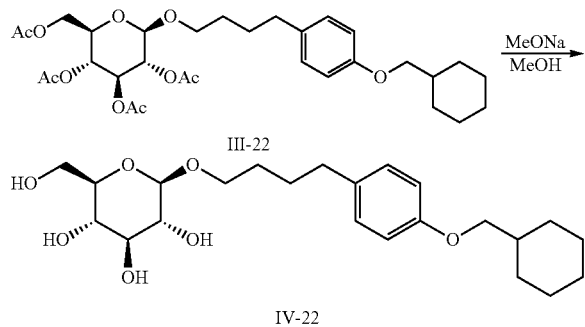

Operation steps: Replace reaction flask with nitrogen for 3 times, add methanol as solvent, and start stirring. Add intermediate III-22 into reaction flask, control temperature at 25±5° C., add sodium methoxide into reaction flask, and stir to react for 2 h. After reaction, conduct diatomite filtration, and collect filtrate after methanol leaching. Add (H+) ion exchange resin and stir for 10 h. Filter to remove (H+) ion exchange resin. Conduct column chromatography isolation after organic phase concentration, and obtain final product IV-22, with a yield of 88%. 1H NMR (400 MHz, $CD_3OD$): δ 7.06 (d, J=8. Hz, 2H), 6.78 (d, J=8.6 Hz, 2H), 4.23 (d, J=7.8 Hz, 1H), 3.95-3.82 (m, 2H), 3.72 (d, J=6.4 Hz, 2H), 3.66 (dd, J=11.9, 5.2 Hz, 1H), 3.59-3.50 (m, 1H), 3.37-3.20 (m, 3H), 3.19-3.12 (m, 1H), 2.56 (t, J=7.1 Hz, 2H), 1.86 (d, J=13.1 Hz, 2H), 1.81-1.57 (m, 8H), 1.38-1.16 (m, 3H), 1.09 (m, 2H). LRMS(ESI): [M+Na]+ 447.2; HRMS(ESI): m/z Calcd for $C_{23}H_{36}O_7Na^+$ [M+Na]+: 447.2353, Found: 447.2352.

Example 33

Synthesis of 1-[4(4-neopentyloxyphenyl)butyl]-2,3,4,6-O-tetraacetyl-β-D-glucopyranoside III-23

4-(4-(neopentyloxy)phenyl)butan-1-ol

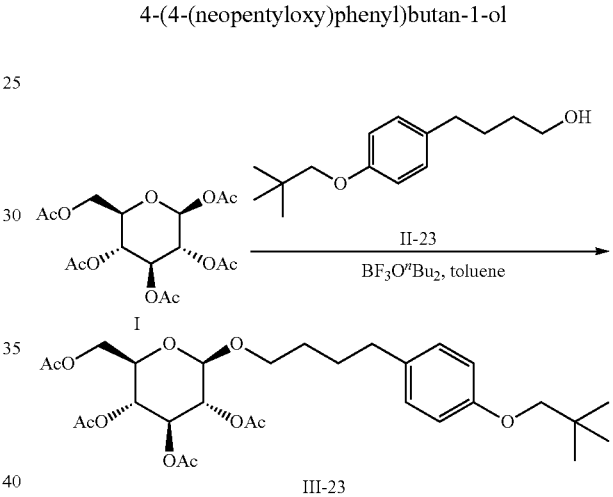

Operation steps: Replace reaction flask with nitrogen for 3 times, add toluene as solvent, and start stirring. Then, add β-D-glucose pentaacetate I and 4-(4-(neopentyloxy)phenyl)butan-1-ol II-23 in turn. Cool reaction flask to 0±5° C., drop boron trifluoride dibutyl etherate, and continue to stir for 12 h after that. After reaction, drop water to system to quench, separate liquid, wash organic phase with $Na_2CO_3$ water solution, separate liquid, and wash organic phase with water once again. Collect organic phase after liquid separation. Conduct column chromatography isolation after concentrating organic phase to no obvious fraction, and obtain compound III-23, with a yield of 15%. LRMS(ESI): [M+Na]+ 589.2.

Synthesis of 1-(4-neopentyloxy)phenylbutyl-β-D-glucopyranoside IV-23

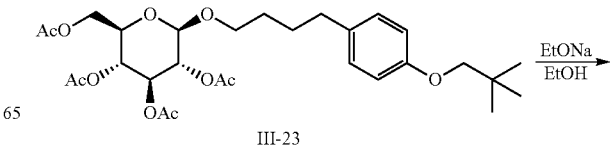

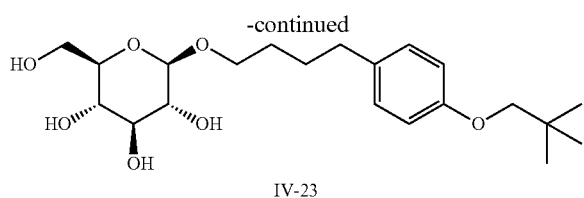

IV-23

Operation steps: Replace reaction flask with nitrogen for 3 times, add ethanol as solvent, and start stirring. Add intermediate III-23 into reaction flask, control temperature at 25±5° C., add sodium ethoxide into reaction flask, and stir to react for 2 h. After reaction, conduct diatomite filtration, and collect filtrate after ethanol leaching. Add (H⁺) ion exchange resin and stir for 10 h. Filter to remove (H⁺) ion exchange resin. Conduct column chromatography isolation after organic phase concentration, and obtain final product IV-23, with a yield of 90%. $^1$H NMR (400 MHz, CD$_3$OD): δ 7.10 (d, J=8.5 Hz, 2H), 6.82 (d, J=8.5 Hz, 2H), 4.27 (d, J=7.8 Hz, 1H), 4.01-3.82 (m, 2H), 3.71 (d, J=5.2 Hz, 1H), 3.60 (m, 3H), 3.42-3.24 (m, 4H), 3.20 (t, J=8.4 Hz, 1H), 2.59 (t, J=7.0 Hz, 2H), 1.78-1.53 (m, 4H), 1.06 (s, 9H). LRMS (ESI): [M+Na]⁺ 421.1; HRMS(ESI): m/z Calcd for C$_{21}$H$_{34}$O$_7$Na⁺ [M+Na]⁺: 421.2197, Found: 421.2194.

Example 34

Synthesis of 1-[4(4-(3,3-dimethylbutoxy)phenyl)butyl]-2,3,4,6-O-tetraacetyl-β-D-glucopyranoside III-24

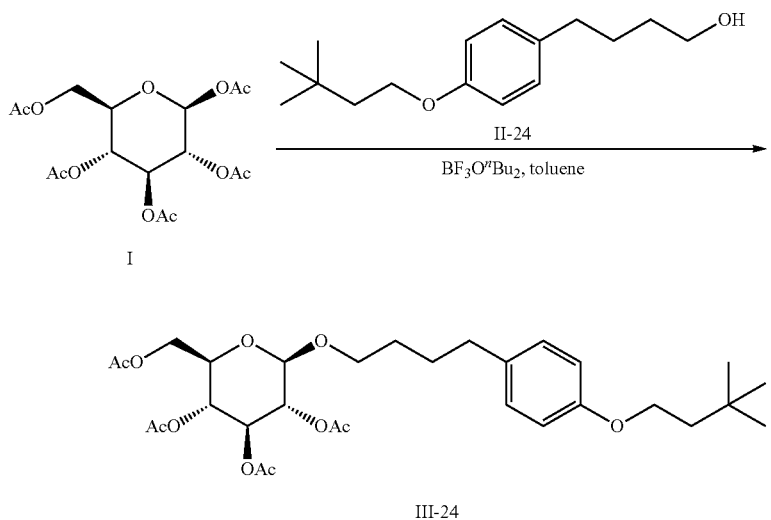

Operation steps: Replace reaction flask with nitrogen for 3 times, add toluene as solvent, and start stirring. Then, add β-D-glucose pentaacetate I and 4-(4-(3,3-dimethylbutoxy)phenyl)butan-1-ol II-24 in turn. Cool reaction flask to 0±5° C., drop boron trifluoride dibutyl etherate, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-24, with a yield of 18%. LRMS(ESI): [M+Na]⁺ 603.2.

Synthesis of 1-(4-(3,3-dimethylbutoxy)phenyl)butyl-β-D-glucopyranoside IV-24

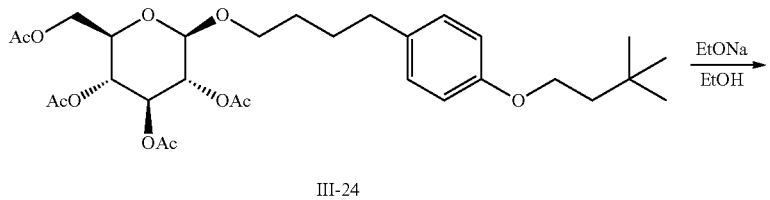

III-24

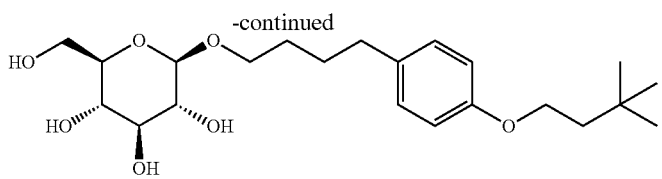

IV-24

Operation steps: Replace reaction flask with nitrogen for 3 times, add ethanol as solvent, and start stirring. Add intermediate III-24 into reaction flask, control temperature at 25±5° C., add sodium ethoxide into reaction flask, and stir to react for 2 h. After reaction, conduct diatomite filtration, and collect filtrate after ethanol leaching. Add (H⁺) ion exchange resin and stir for 10 h. Filter to remove (H⁺) ion exchange resin. Conduct column chromatography isolation after organic phase concentration, and obtain final product IV-24, with a yield of 80%. $^1$H NMR (400 MHz, CD$_3$OD): δ 7.07 (d, J=8.5 Hz, 2H), 6.79 (d, J=8.6 Hz, 2H), 4.23 (d, J=7.8 Hz, 1H), 3.99 (t, J=7.1 Hz, 2H), 3.91 (dt, J=9.3, 6.3 Hz, 1H), 3.85 (dd, J=11.9, 1.9 Hz, 1H), 3.67 (dd, J=11.9, 5.3 Hz, 1H), 3.57-3.52 (m, 1H), 3.26-3.11 (m, 4H), 2.56 (t, J=7.1 Hz, 2H), 1.75-1.53 (m, 6H), 0.99 (s, 9H). LRMS(ESI): [M+Na]⁺ 435.1; HRMS(ESI): m/z Calcd for C$_{22}$H$_{36}$O$_7$Na⁺ [M+Na]⁺: 435.2353, Found: 435.2352.

Example 35

Synthesis of 1-[4(4-benzyloxyphenyl)butyl]-2,3,4,6-O-tetraacetyl-β-D-glucopyranoside III-25

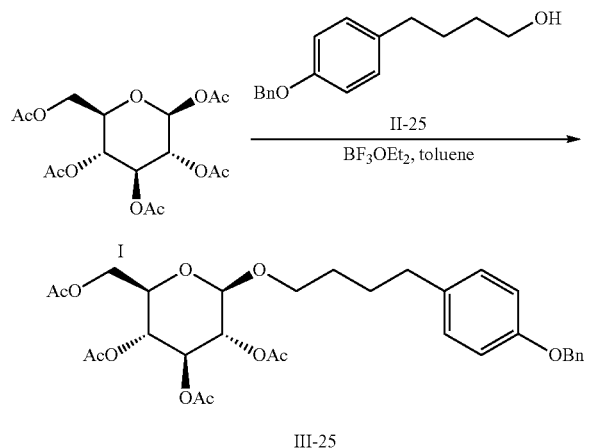

Operation steps: Replace reaction flask with nitrogen for 3 times, add toluene as solvent, and start stirring. Then, add β-D-glucose pentaacetate I and 4-(4-(benzyloxy)phenyl)butan-1-ol II-25 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after concentrating organic phase to no obvious fraction, and obtain compound III-25, with a yield of 35%. LRMS(ESI): [M+Na]⁺ 609.6.

Synthesis of 1-(4-benzyloxy)phenylbutyl-β-D-glucopyranoside IV-25

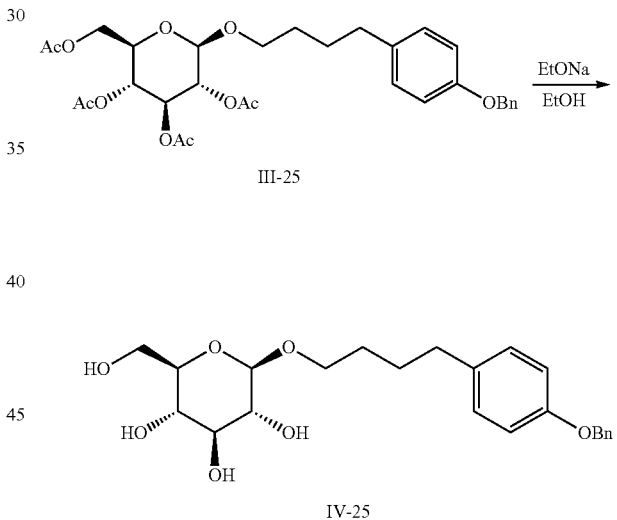

Operation steps: Replace reaction flask with nitrogen for 3 times, add ethanol as solvent, and start stirring. Add intermediate III-25 into reaction flask, control temperature at 25±5° C., add sodium ethoxide into reaction flask, and stir to react for 2 h. After reaction, conduct diatomite filtration, and collect filtrate after ethanol leaching. Add (H⁺) ion exchange resin and stir for 10 h. Filter to remove (H⁺) ion exchange resin. Conduct column chromatography isolation after organic phase concentration, and obtain final product IV-25, with a yield of 91%. $^1$H NMR (400 MHz, CD$_3$OD): δ 7.34 (m, 5H), 7.09 (d, J=8.3 Hz, 2H), 6.88 (d, J=8.4 Hz, 2H), 5.03 (s, 2H), 4.23 (d, J=7.8 Hz, 1H), 4.01-3.82 (m, 2H), 3.66 (dd, J=11.8, 5.0 Hz, 1H), 3.59-3.47 (m, 1H), 3.39-3.22 (m, 3H), 3.16 (t, J=8.3 Hz, 1H), 2.56 (t, J=6.9 Hz, 2H), 1.65 (d, J=4.1 Hz, 4H). LRMS(ESI): [M+Na]⁺ 441.1; HRMS (ESI): m/z Calcd for C$_{23}$H$_{30}$O$_7$Na⁺: 441.1884, Found: 441.1880.

Example 36

Synthesis of 1-[4-(4-((2-fluorobenzyl)oxy)phenyl)butyl]-2,3,4,6-O-tetraacetyl-β-D-glucopyranoside III-26

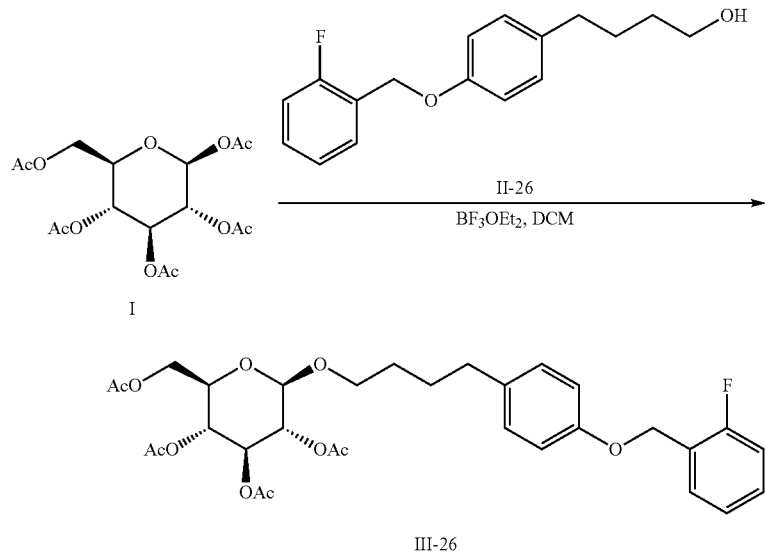

Operation steps: Replace reaction flask with nitrogen for 3 times, add dichloromethane as solvent, and start stirring. Then, add β-D-glucose pentaacetate I and 4-(4-((2-fluorobenzyl)oxy)phenyl)butan-1-ol II-26 in turn. Cool reaction flask to 0±5° C., drop boron trifluoride ether complex, and continue to stir for 12 h after that. After reaction, drop water to system to quench, separate liquid, wash organic phase with $Na_2CO_3$ water solution, separate liquid, and wash organic phase with water once again. Collect organic phase after liquid separation. Conduct column chromatography isolation after organic phase concentration, and obtain compound III-26, with a yield of 37%. LRMS(ESI): $[M+Na]^+$ 654.23.

Synthesis of 1-[4-((2-fluorobenzyl)oxy)]phenyl-butyl-β-D-glucopyranoside IV-26

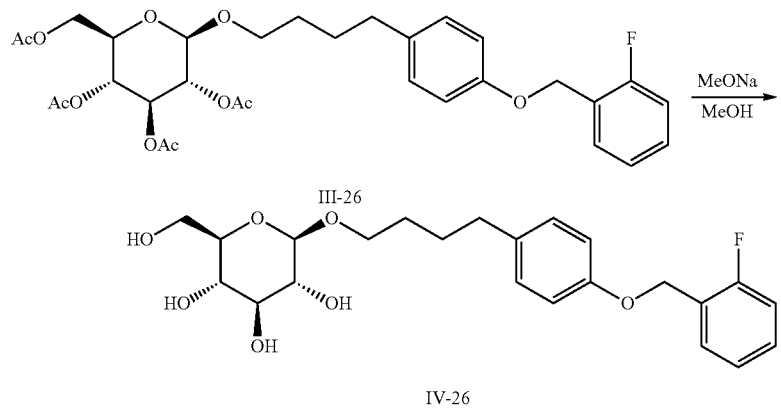

Operation steps: Replace reaction flask with nitrogen for 3 times, add methanol as solvent, and start stirring. Add intermediate III-26 into reaction flask, control temperature at 25±5° C., add sodium methoxide into reaction flask, and stir to react for 2 h. After reaction, conduct diatomite filtration, and collect filtrate after methanol leaching. Add ($H^+$) ion exchange resin and stir for 10 h. Filter to remove ($H^+$) ion exchange resin. Conduct column chromatography isolation after organic phase concentration, and obtain final product IV-26, with a yield of 88%. $^1$H NMR (400 MHz, $CD_3OD$): δ 7.53 (td, J=7.5, 1.3 Hz, 1H), 7.42-7.34 (m, 1H), 7.21 (td, J=7.5, 1.0 Hz, 1H), 7.18-7.10 (m, 1H), 7.14 (d, J=8.6 Hz, 2H), 6.92 (d, J=8.6 Hz, 2H), 5.12 (s, 2H), 4.27 (d, J=7.8 Hz, 1H), 3.95 (dt, J=9.4, 6.3 Hz, 1H), 3.89 (dd, J=11.9, 1.8 Hz, 1H), 3.69 (dd, J=11.9, 5.2 Hz, 1H), 3.58 (dt, J=9.5, 6.3 Hz, 1H), 3.39-3.25 (m, 3H), 3.24-3.16 (m, 1H), 2.61 (t, J=7.1 Hz, 2H), 1.78-1.59 (m, 4H). LRMS(ESI): $[M+Na]^+$ 459.20.

Example 37

Synthesis of 1-[4-(4-((3-fluorobenzyl)oxy)phenyl)butyl]-2,3,4,6-O-tetraacetyl-β-D-glucopyranoside III-27

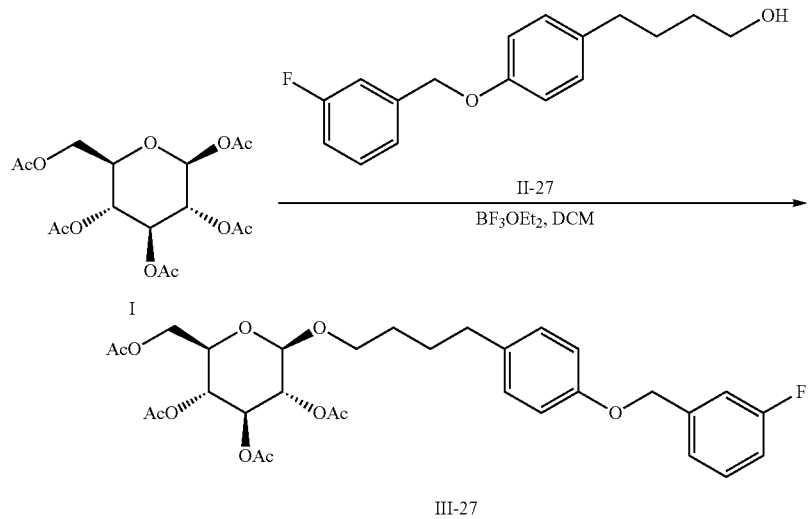

Operation steps: Replace reaction flask with nitrogen for 3 times, add dichloromethane as solvent, and start stirring. Then, add β-D-glucose pentaacetate I and 4-(4-((3-fluorobenzyl)oxy)phenyl)butan-1-ol II-27 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-27, with a yield of 40%. LRMS(ESI): [M+Na]$^+$ 627.2.

Synthesis of 1-[4-((3-fluorobenzyl)oxy)]phenyl-butyl-β-D-glucopyranoside IV-27

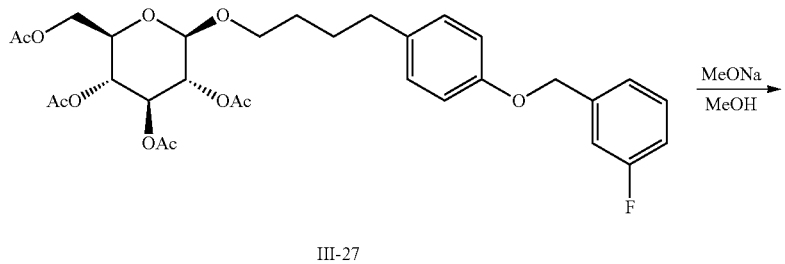

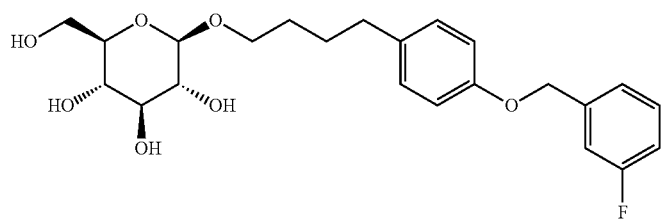

Operation steps: Replace reaction flask with nitrogen for 3 times, add methanol as solvent, and start stirring. Add intermediate III-27 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-27, with a yield of 84%. $^1$H NMR (400 MHz, CD$_3$OD): δ 7.40 (dt, J=7.9, 5.9 Hz, 1H), 7.26 (d, J=7.7 Hz, 1H), 7.20 (d, J=9.9 Hz, 1H), 7.13 (d, J=8.6 Hz, 2H), 7.05 (td, J=8.5, 2.3 Hz, 1H), 6.91 (d, J=8.6 Hz, 2H), 5.09 (s, 2H), 4.27 (d, J=7.8 Hz, 1H), 3.95 (dt, J=9.4, 6.3 Hz, 1H), 3.89 (dd, J=11.9, 1.8 Hz, 1H), 3.69 (dd, J=11.9, 5.2 Hz, 1H), 3.62-3.54 (m, 1H), 3.41-3.24 (m, 3H), 3.23-3.15 (m, 1H), 2.60 (t, J=7.1 Hz, 2H), 1.90-1.55 (m, 4H). LRMS(ESI): [M+Na]$^+$ 459.2.

Example 38

Synthesis of 1-[4-(4-((4-fluorobenzyl)oxy)phenyl)butyl]-2,3,4,6-O-tetraacetyl-β-D-glucopyranoside III-28

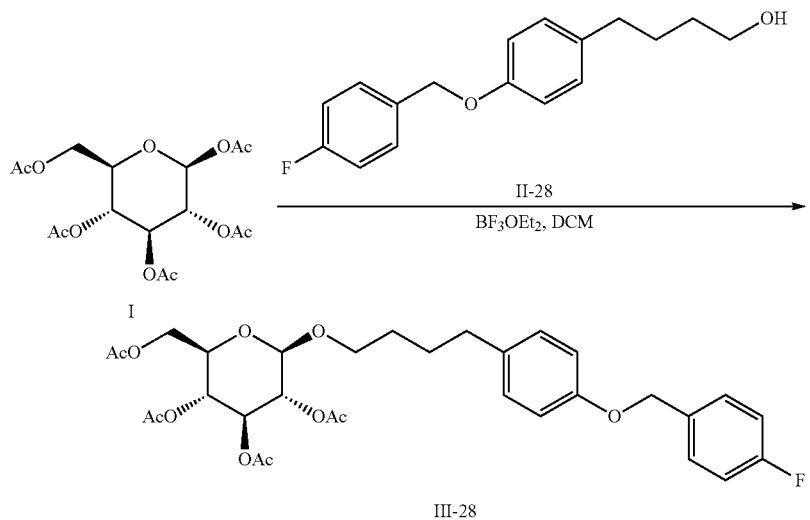

Operation steps: Replace reaction flask with nitrogen for 3 times, add dichloromethane as solvent, and start stirring. Then, add β-D-glucose pentaacetate I and 4-(4-((4-fluorobenzyl)oxy)phenyl)butan-1-ol II-28 in turn. Cool reaction flask to 0±5° C., drop boron trifluoride tetrahydrofuran complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-28 with a yield of 44%. LRMS(ESI): [M+Na]$^+$ 654.23.

Synthesis of 1-[4-((4-fluorobenzyl)oxy)]phenyl-butyl-β-D-glucopyranoside IV-28

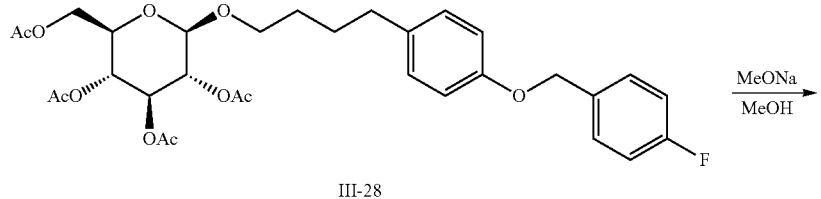

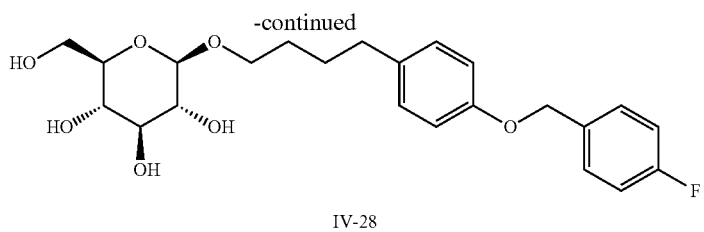

IV-28

Operation steps: Replace reaction flask with nitrogen for 3 times, add methanol as solvent, and start stirring. Add intermediate III-28 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) type ion exchange resin. Conduct column chromatography isolation after organic phase concentration, and obtain final product IV-28, with a yield of 83%. $^1$H NMR (400 MHz, CD$_3$OD): δ 7.47 (dd, J=8.5, 5.5 Hz, 2H), 7.13 (d, J=8.6 Hz, 4H), 7.14-7.09 (m, 1H), 6.91 (d, J=8.6 Hz, 2H), 5.04 (s, 2H), 4.27 (d, J=7.8 Hz, 1H), 3.95 (dt, J=9.3, 6.2 Hz, 1H), 3.89 (dd, J=11.8, 1.7 Hz, 1H), 3.69 (dd, J=11.8, 5.2 Hz, 1H), 3.58 (dt, J=9.4, 6.2 Hz, 1H), 3.33-3.24 (m, 3H), 3.23-3.14 (m, 1H), 2.60 (t, J=7.1 Hz, 2H), 1.91-1.56 (m, 4H). LRMS(ESI): [M+Na]$^+$ 459.2.

Example 39

Synthesis of 1-[4-(4-(3-(trifluoromethyl)benzyl)oxy)phenyl)butyl]-2,3,4,6-O-tetraacetyl-β-D-glucopyranoside III-29

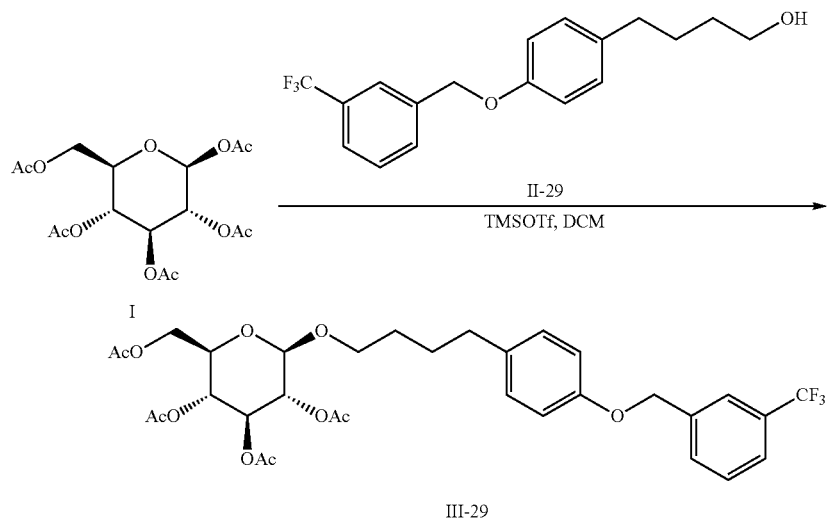

Operation steps: Replace reaction flask with nitrogen for 3 times, add dichloromethane as solvent, and start stirring. Then, add β-D-glucose pentaacetate I and 4-(4-((3-(trifluoromethyl)benzyl)oxy)phenyl)butan-1-ol II-29 in turn. Cool reaction flask to 0±5° C., drop trifluoromethanesulfonic acid trimethylsilyl, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-29, with a yield of 34%. LRMS(ESI): [M+Na]$^+$ 677.23.

Synthesis of 1-[4-((3-(trifluoromethyl)benzyl)oxy)]
phenylbutyl-β-D-glucopyranoside IV-29

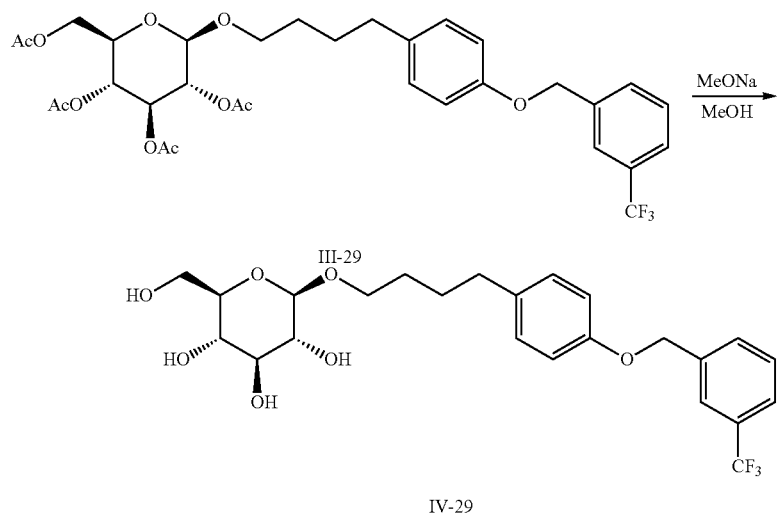

Operation steps: Replace reaction flask with nitrogen for 3 times, add methanol as solvent, and start stirring. Add intermediate III-29 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) type ion exchange resin. Conduct column chromatography isolation after organic phase concentration, and obtain final product IV-29, with a yield of 81%. $^1$H NMR (400 MHz, CD$_3$OD): δ 7.74 (s, 1H), 7.69 (d, J=7.4 Hz, 1H), 7.62-7.53 (m, 2H), 7.11 (d, J=8.6 Hz, 2H), 6.91 (d, J=8.6 Hz, 2H), 5.13 (s, 2H), 4.23 (d, J=7.8 Hz, 1H), 3.92 (dt, J=9.4, 6.3 Hz, 1H), 3.85 (dd, J=11.9, 1.7 Hz, 1H), 3.66 (dd, J=11.8, 5.2 Hz, 1H), 3.55 (dt, J=9.6, 6.2 Hz, 1H), 3.37-3.32 (m, 1H), 3.26 (t, J=5.9 Hz, 2H), 3.20-3.11 (m, 1H), 2.57 (t, J=7.1 Hz, 2H), 1.80-1.49 (m, 4H). LRMS(ESI): [M+Na]⁺ 509.20.

Example 40

Synthesis of 1-[4-(4-(4-(trifluoromethyl)benzyl)oxy)
phenyl)butyl]-2,3,4,6-O-tetraacetyl-β-D-glucopyra-
noside III-30

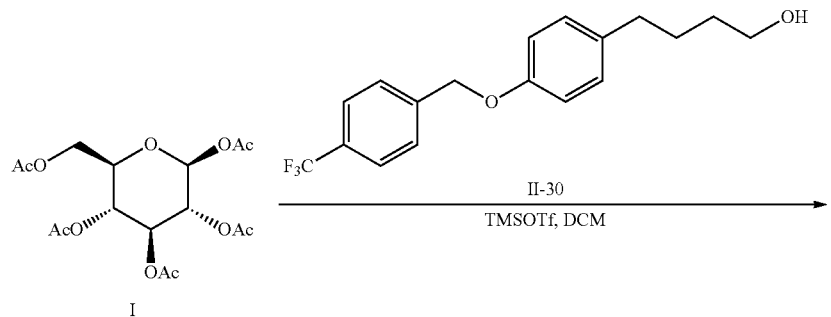

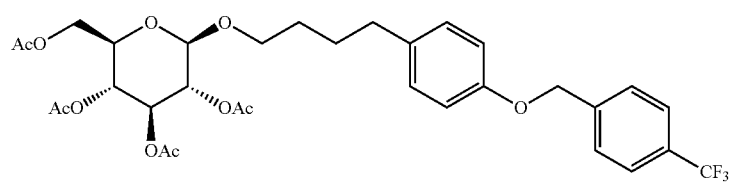

Operation steps: Replace reaction flask with nitrogen for 3 times, add dichloromethane as solvent, and start stirring. Then, add β-D-glucose pentaacetate I and 4-(4-((4-(trifluoromethyl)benzyl)oxy)phenyl)butan-1-ol II-30 in turn. Cool reaction flask to 0±5° C., drop trifluoromethanesulfonic acid trimethylsilyl, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-30, with a yield of 40%. LRMS(ESI): [M+Na]$^+$ 677.2.

Synthesis of 1-[4-((4-(trifluoromethyl)benzyl)oxy)]phenylbutyl-β-D-glucopyranoside IV-30

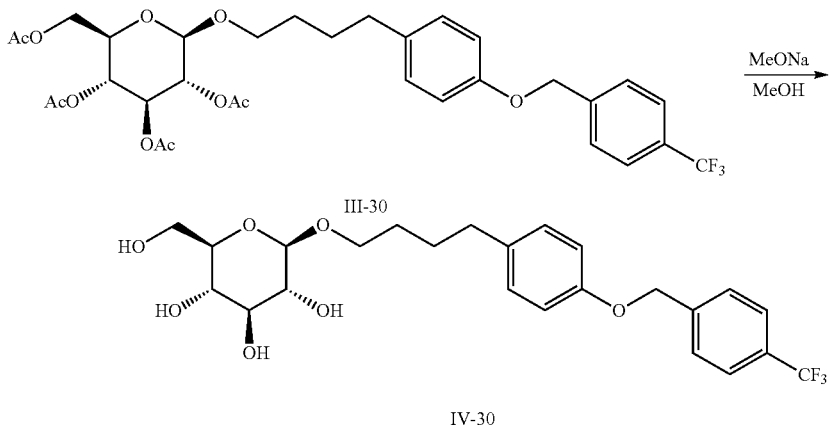

Operation steps: Replace reaction flask with nitrogen for 3 times, add methanol as solvent, and start stirring. Add intermediate III-30 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. After concentrating the organic phase, the final product IV-30 was obtained by column chromatography with a yield of 85%. $^1$H NMR (400 MHz, CD$_3$OD): δ 7.68 (dd, J=18.9, 8.3 Hz, 4H), 7.14 (d, J=8.6 Hz, 2H), 6.93 (d, J=8.6 Hz, 2H), 5.17 (s, 2H), 4.27 (d, J=7.8 Hz, 1H), 3.95 (dt, J=6.3, 3.3 Hz, 1H), 3.89 (dd, J=11.8, 1.7 Hz, 1H), 3.69 (dd, J=11.8, 5.2 Hz, 1H), 3.62-3.54 (m, 1H), 3.42-3.24 (m, 3H), 3.23-3.15 (m, 1H), 2.61 (t, J=7.1 Hz, 2H), 1.83-1.52 (m, 4H). LRMS(ESI): [M+Na]$^+$ 509.2.

Example 41

Synthesis of 1-[4(4-(oxetan-3-ylmethoxy)phenyl)butyl]-2,3,4,6-O-tetraacetyl-β-D-glucopyranoside III-31

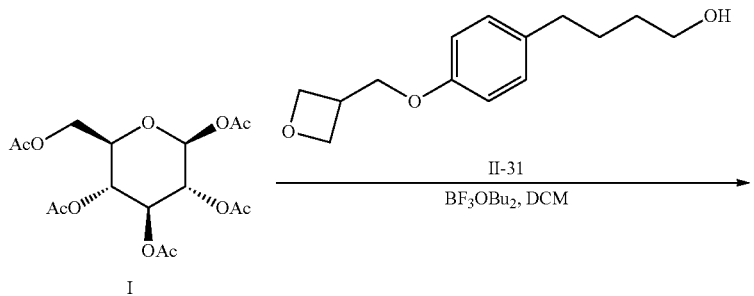

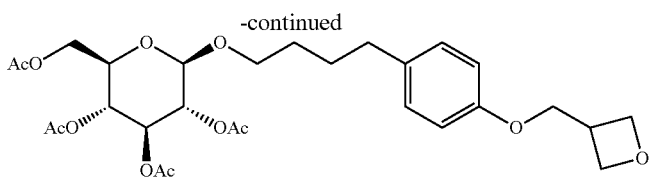

III-31

Operation steps: Replace reaction flask with nitrogen for 3 times, add dichloromethane as solvent, and start stirring. Then, add β-D-glucose pentaacetate I and 4-(4-(oxetan-3-ylmethoxy)phenyl)butan-1-ol II-31 in turn. Cool reaction flask to 0±5° C., drop boron trifluoride dibutyl etherate, and continue to stir for 12 h after that. After reaction, drop water to system to quench, separate liquid, wash organic phase with Na₂CO₃ water solution, separate liquid, and wash organic phase with water once again. Collect organic phase after liquid separation. Conduct column chromatography isolation after organic phase concentration, and obtain compound III-31, with a yield of 42%. LRMS(ESI): [M+Na]⁺ 589.2.

Synthesis of 1-[4-(oxetan-3-ylmethoxy)]phenyl-butyl-β-D-glucopyranoside IV-31

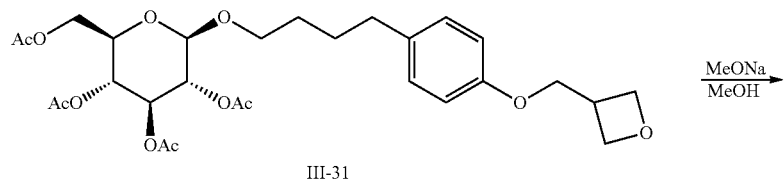

III-31

$\xrightarrow{\text{MeONa}}{\text{MeOH}}$

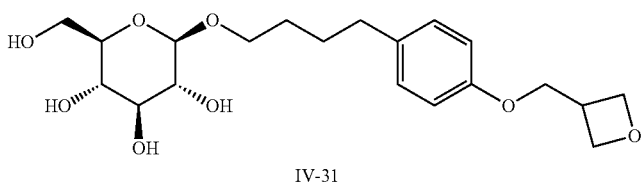

IV-31

Operation steps: Replace reaction flask with nitrogen for 3 times, add methanol as solvent, and start stirring. Add intermediate III-31 into reaction flask, control temperature at 25±5° C., add sodium methoxide into reaction flask, and stir to react for 2 h. After reaction, conduct diatomite filtration, and collect filtrate after methanol leaching. Add (H⁺) ion exchange resin and stir for 10 h. Filter to remove (H⁺) type ion exchange resin. Conduct column chromatography isolation after organic phase concentration, and obtain final product IV-31, with a yield of 81%. $^1$H NMR (400 MHz, CD₃OD): δ 7.13 (d, J=8.5 Hz, 2H), 6.88 (d, J=8.6 Hz, 2H), 4.97-4.83 (m, 2H), 4.62 (t, J=6.0 Hz, 2H), 4.27 (d, J=7.8 Hz, 1H), 4.19 (d, J=6.4 Hz, 2H), 3.95 (dt, J=6.3, 3.3 Hz, 1H), 3.89 (dd, J=11.8, 1.7 Hz, 1H), 3.69 (dd, J=11.8, 5.2 Hz, 1H), 3.63-3.54 (m, 1H), 3.52-3.41 (m, 1H), 3.41-3.24 (m, 3H), 3.23-3.15 (m, 1H), 2.61 (t, J=7.1 Hz, 2H), 1.81-1.57 (m, 4H). LRMS(ESI): [M+Na]⁺ 421.1.

Example 42

Synthesis of 1-[4(4-((tetrahydro-2H-pyran-4-yl)methoxy)phenyl)butyl]-2,3,4,6-O-tetraacetyl-β-D-glucopyranoside III-32

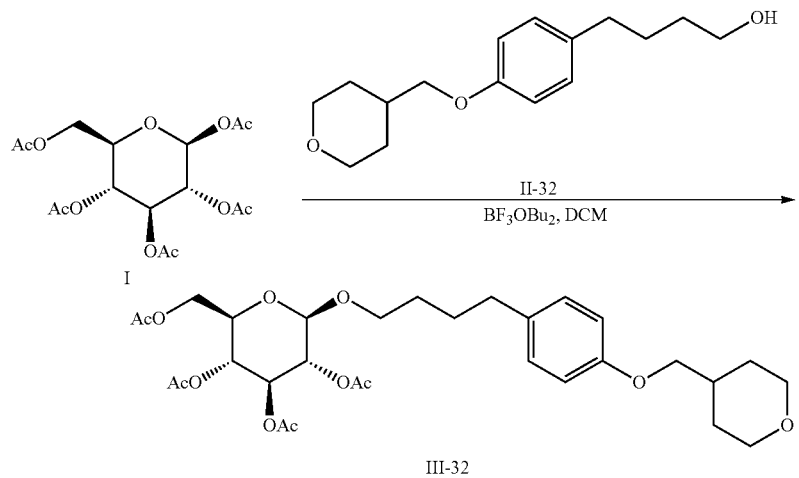

Operation steps: Replace reaction flask with nitrogen for 3 times, add dichloromethane as solvent, and start stirring. Then, add β-D-glucose pentaacetate I and 4-(4-((tetrahydro-2H-pyran-4-yl)methoxy)phenyl)butan-1-ol II-32 in turn. Cool reaction flask to 0±5° C., drop boron trifluoride dibutyl etherate, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-32, with a yield of 34%. LRMS(ESI): [M+Na]$^+$ 617.6.

Synthesis of 1-[4-((tetrahydro-2H-pyran-4-yl)methoxy)]phenylbutyl-β-D-glucopyranoside IV-32

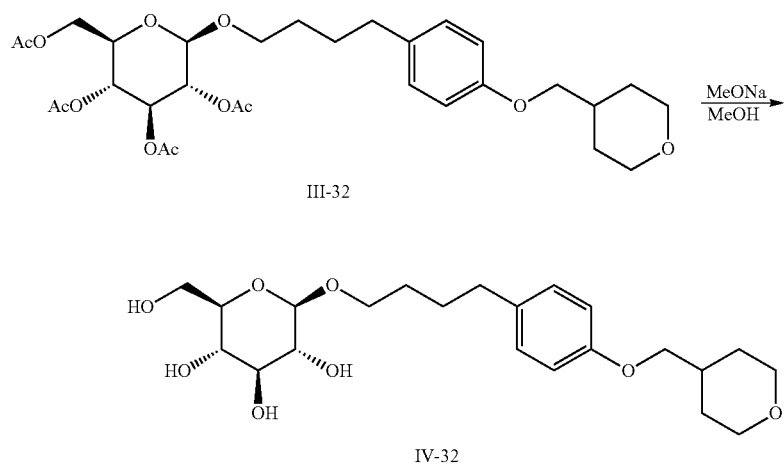

Operation steps: Replace reaction flask with nitrogen for 3 times, add methanol as solvent, and start stirring. Add intermediate III-32 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-32, with a yield of 80%. $^1$H NMR (400 MHz, CD$_3$OD): δ 7.11 (d, J=8.5 Hz, 2H), 6.83 (d, J=8.5 Hz, 2H), 4.27 (d, J=7.8 Hz, 1H), 4.05-3.86 (m, 4H), 3.82 (d, J=6.3 Hz, 2H), 3.69 (dd, J=11.8, 5.2 Hz, 1H), 3.58 (dt, J=9.5, 6.2 Hz, 1H), 3.49 (td, J=12.0, 1.7 Hz, 2H), 3.40-3.24 (m, 3H), 3.19 (t, J=8.4 Hz, 1H), 2.60 (t, J=7.1 Hz, 2H), 2.14-1.98 (m, 1H), 1.85-1.60 (m, 6H), 1.47 (qd, J=12.3, 4.5 Hz, 2H). LRMS (ESI): [M+Na]$^+$ 449.2; HRMS(ESI): m/z Calcd for C$_{22}$H$_{35}$O$_8^+$: 427.2326, Found: 427.2323.

Example 43

Synthesis of 1-[4(4-(pyridin-2-yl-methoxy)phenyl)butyl]-2,3,4,6-O-tetraacetyl-β-D-glucopyranoside III-33

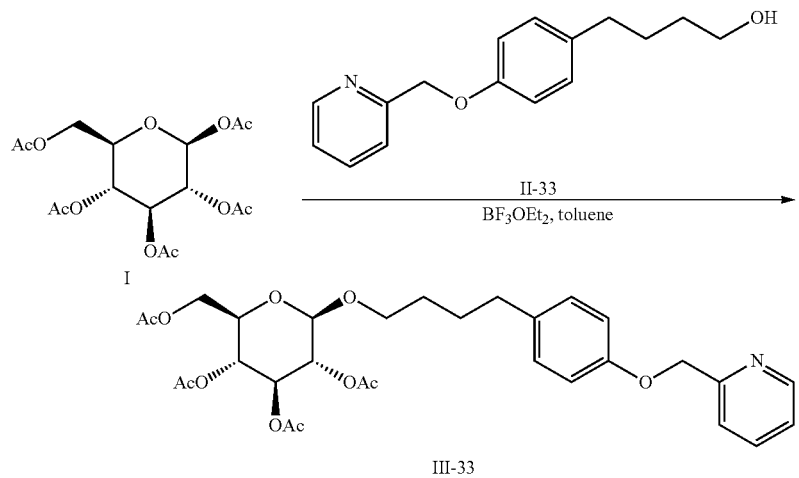

Operation steps: Replace reaction flask with nitrogen for 3 times, add toluene as solvent, and start stirring. Then, add β-D-glucose pentaacetate I and 4-(4-(pyridin-2-ylmethoxy)phenyl)butan-1-ol II-33 in turn. Cool reaction flask to 0±5° C., drop boron trifluoride ether complex, and continue to stir for 12 h after that. After reaction, drop water to system to quench, separate liquid, wash organic phase with $Na_2CO_3$ water solution, separate liquid, and wash organic phase with water once again. Collect organic phase after liquid separation. Conduct column chromatography isolation after organic phase concentration, and obtain compound III-33, with a yield of 28%. LRMS(ESI): [M+Na]$^+$ 610.2.

Synthesis of 1-[4-(pyridin-2-yl-methoxy)]phenyl-butyl-β-D-glucopyranoside IV-33

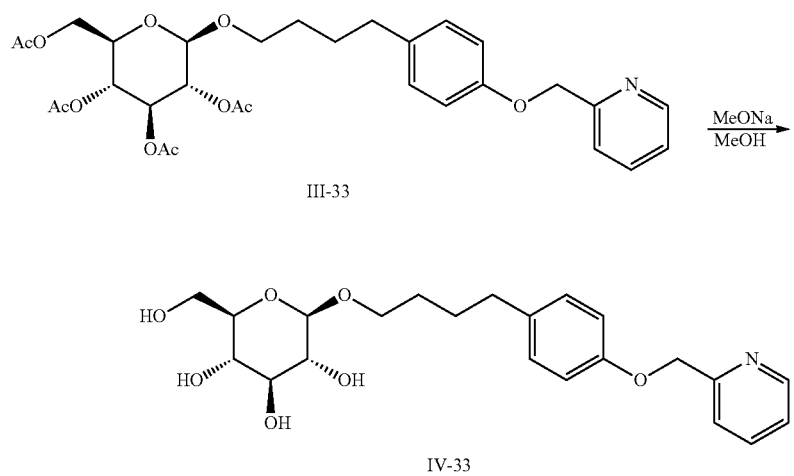

Operation steps: Replace reaction flask with nitrogen for 3 times, add methanol as solvent, and start stirring. Add intermediate III-33 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-33, with a yield of 79%. $^1$H NMR (400 MHz, CD$_3$OD): δ 8.53 (d, J=4.4 Hz, 1H), 7.86 (td, J=7.8, 1.6 Hz, 1H), 7.59 (d, J=7.9 Hz, 1H), 7.36 (dd, J=7.0, 5.4 Hz, 1H), 7.10 (d, J=8.6 Hz, 2H), 6.90 (d, J=8.6 Hz, 2H), 5.13 (s, 2H), 4.23 (d, J=7.8 Hz, 1H), 3.95-3.88 (m, 1H), 3.85 (dd, J=11.9, 1.7 Hz, 1H), 3.66 (dd, J=11.9, 5.2 Hz, 1H), 3.59-3.51 (m, 1H), 3.35-3.12 (m, 4H), 2.57 (t, J=7.1 Hz, 2H), 1.81-1.52 (m, 4H). LRMS(ESI): [M+Na]$^+$ 442.0; HRMS(ESI): m/z Calcd for $C_{22}H_{29}O_7NNa^+$ [M+Na]$^+$: 442.1836, Found: 442.1834.

Example 44

Synthesis of 1-[4(4-(pyridin-3-yl-methoxy)phenyl)butyl]-2,3,4,6-O-tetraacetyl-β-D-glucopyranoside III-34

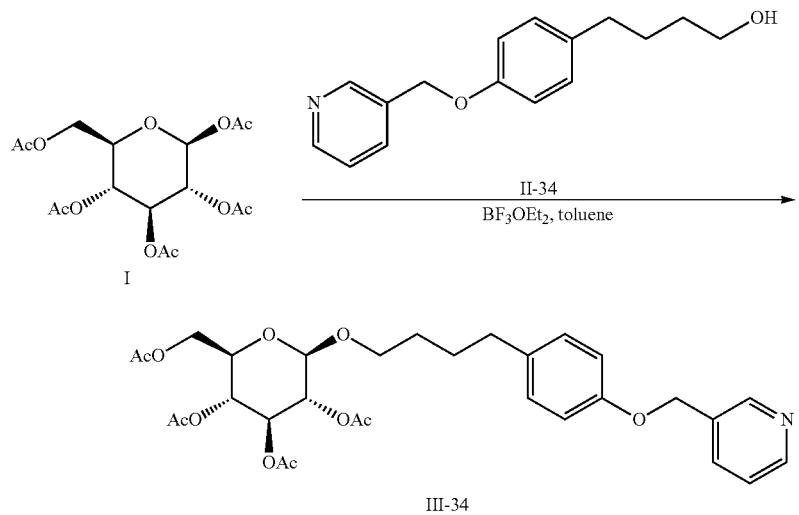

Operation steps: Replace reaction flask with nitrogen for 3 times, add toluene as solvent, and start stirring. Then, add β-D-glucose pentaacetate I and 4-(4-(pyridin-3-ylmethoxy)phenyl)butan-1-ol II-34 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-34, with a yield of 31%. LRMS(ESI): [M+Na]$^+$ 610.6.

Synthesis of 1-[4-(pyridin-3-yl-methoxy)]phenyl-butyl-β-D-glucopyranoside IV-34

Operation steps: Replace reaction flask with nitrogen for 3 times, add methanol as solvent, and start stirring. Add intermediate III-34 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-34, with a yield of 85%. $^1$H NMR (400 MHz, CD$_3$OD): δ 8.65 (d, J=1.2 Hz, 1H), 8.52 (dd, J=4.9, 1.2 Hz, 1H), 7.96 (d, J=7.9 Hz, 1H), 7.48 (dd, J=7.8, 5.0 Hz, 1H), 7.14 (d, J=8.5 Hz, 2H), 6.94 (d, J=8.6 Hz, 2H), 5.14 (s, 2H), 4.27 (d, J=7.8 Hz, 1H), 3.99-3.85 (m, 2H), 3.69 (dd, J=11.9, 5.2 Hz, 1H), 3.58 (dt, J=9.4, 6.2 Hz, 1H), 3.43-3.24 (m, 3H), 3.23-3.16 (m, 1H), 2.60 (t, J=7.1 Hz, 2H), 1.76-1.60 (m, 4H). LRMS(ESI): [M+Na]$^+$ 442.1; HRMS(ESI): m/z Calcd for C$_{22}$H$_{29}$O$_7$NNa$^+$ [M+Na]$^+$: 442.1836, Found: 442.1834.

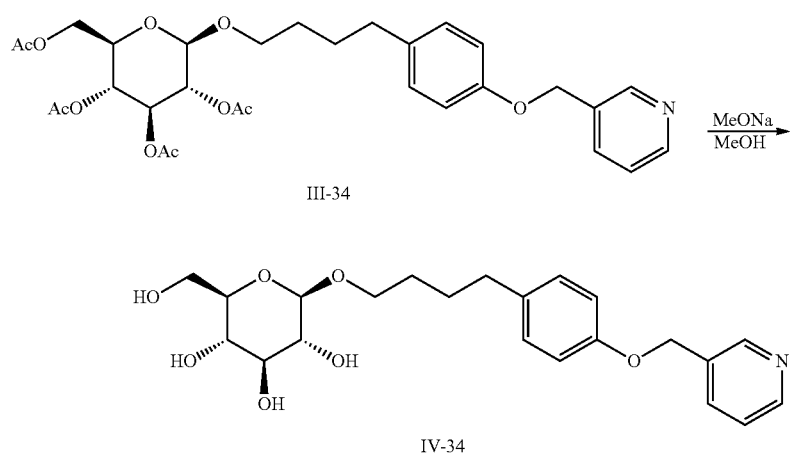

Example 45

Synthesis of 1-[4(4-(pyridin-4-yl-methoxy)phenyl)butyl]-2,3,4,6-O-tetraacetyl-β-D-glucopyranoside III-35

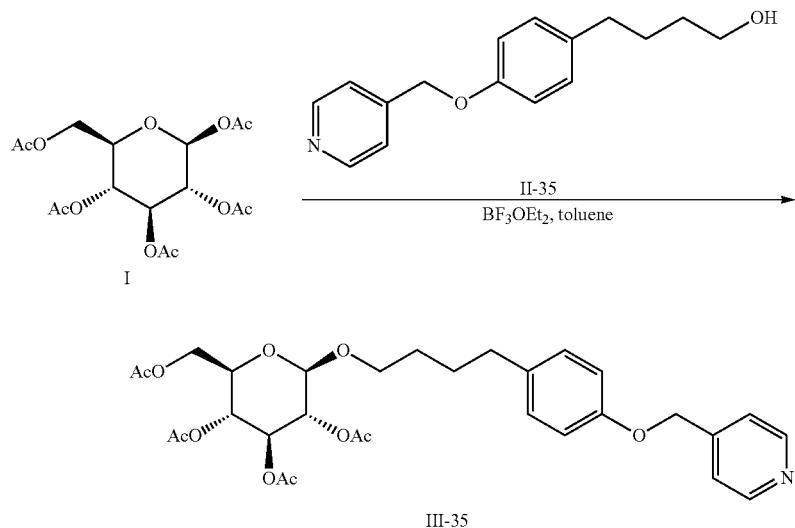

Operation steps: Replace reaction flask with nitrogen for 3 times, add toluene as solvent, and start stirring. Then, add β-D-glucose pentaacetate I and 4-(4-(pyridin-4-ylmethoxy)phenyl)butan-1-ol II-35 in turn. Cool reaction flask to 0±5° C., drop boron trifluoride ether complex, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-35, with a yield of 36%. LRMS(ESI): [M+Na]$^+$ 610.6.

Synthesis of 1-[4-(pyridin-4-yl-methoxyl)]phenyl-butyl-β-D-glucopyranoside IV-35

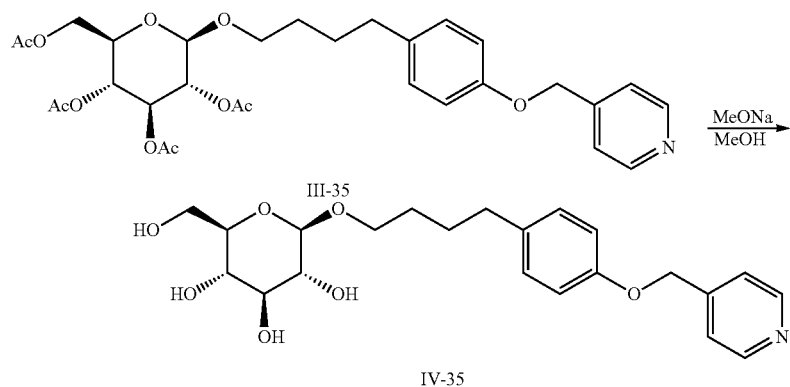

Operation steps: Replace reaction flask with nitrogen for 3 times, add methanol as solvent, and start stirring. Add intermediate III-35 into reaction flask, control temperature at 25±5° C., add sodium methoxide into reaction flask, and stir to react for 2 h. After reaction, conduct diatomite filtration, and collect filtrate after methanol leaching. Add (H$^+$) ion exchange resin and stir for 10 h. Filter to remove (H$^+$) ion exchange resin. Conduct column chromatography isolation after organic phase concentration, and obtain final product IV-35, with a yield of 90%. $^1$H NMR (400 MHz, CD$_3$OD): δ 8.66-8.44 (m, 2H), 7.54 (d, J=5.9 Hz, 2H), 7.15 (d, J=8.6 Hz, 2H), 6.93 (d, J=8.6 Hz, 2H), 5.18 (s, 2H), 4.26 (d, J=7.8 Hz, 1H), 3.95 (dt, J=9.5, 6.3 Hz, 1H), 3.89 (dd, J=11.9, 1.9 Hz, 1H), 3.69 (dd, J=11.8, 5.2 Hz, 1H), 3.62-3.54 (m, 1H), 3.41-3.24 (m, 3H), 3.23-3.16 (m, 1H), 2.61 (t, J=7.1 Hz, 2H), 1.77-1.58 (m, 4H). LRMS(ESI): [M+1-1]±420.2; HRMS(ESI): m/z Calcd for C$_{22}$H$_{30}$O$_7$N$^+$ [M+H]$^+$: 420.2017, Found: 420.2014.

Example 46

Synthesis of 1-[4(4-(hexadecyloxy)phenyl)butyl]-2,3,4,6-O-tetraacetyl-β-D-glucopyranoside III-36

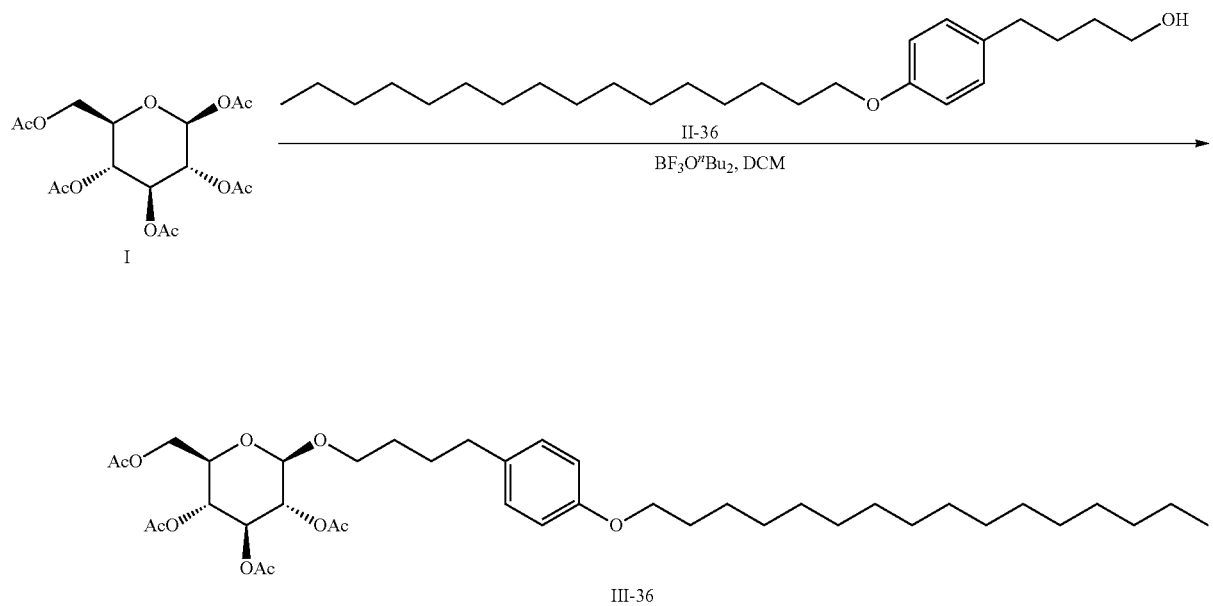

Operation steps: Replace reaction flask with nitrogen for 3 times, add dichloromethane as solvent, and start stirring. Then, add β-D-glucose pentaacetate I and 4-(4-(hexadecyloxy)phenyl)butan-1-ol II-36 in turn. Cool reaction flask to 0±5° C., drop boron trifluoride dibutyl etherate, and continue to stir for 12 h after that. After reaction, drop water to system to quench, separate liquid, wash organic phase with $Na_2CO_3$ water solution, separate liquid, and wash organic phase with water once again. Collect organic phase after liquid separation. Conduct column chromatography isolation after organic phase concentration, and obtain compound III-36, with a yield of 37%. LRMS(ESI): $[M+Na]^+$ 743.4.

Synthesis of 1-[4-(hexadecyloxy)]phenylbutyl-β-D-glucopyranoside IV-36

Operation steps: Replace reaction flask with nitrogen for 3 times, add ethanol as solvent, and start stirring. Add intermediate III-36 into reaction flask, control temperature at 25±5° C., add sodium ethoxide into reaction flask, and stir to react for 2 h. After reaction, conduct diatomite filtration, and collect filtrate after ethanol leaching. Add ($H^+$) ion exchange resin and stir for 10 h. Filter to remove ($H^+$) ion exchange resin. Conduct column chromatography isolation after organic phase concentration, and obtain compound IV-36, with a yield of 78%. $^1$H NMR (400 MHz, $CD_3OD$) δ 7.07 (d, J=8.6 Hz, 2H), 6.79 (d, J=8.6 Hz, 2H), 4.23 (d, J=7.8 Hz, 1H), 3.92 (dd, J=7.9, 5.1 Hz, 2H), 3.85 (dd, J=11.9, 1.9 Hz, 1H), 3.66 (dd, J=11.9, 5.2 Hz, 1H), 3.55 (m, 1H), 3.34-3.21 (m, 4H), 2.56 (t, J=7.1 Hz, 2H), 1.70 (m, 6H), 1.45 (m, 2H), 1.41-1.20 (m, 24H), 0.99 (s, 1H), 0.89 (t, J=6.8 Hz, 3H). LRMS(ESI): $[M+Na]^+$575.3; HRMS(ESI): m/z Calcd for $C_{32}H_{56}O_7Na^+$ $[M+Na]^+$: 575.3918, Found: 575.3917.

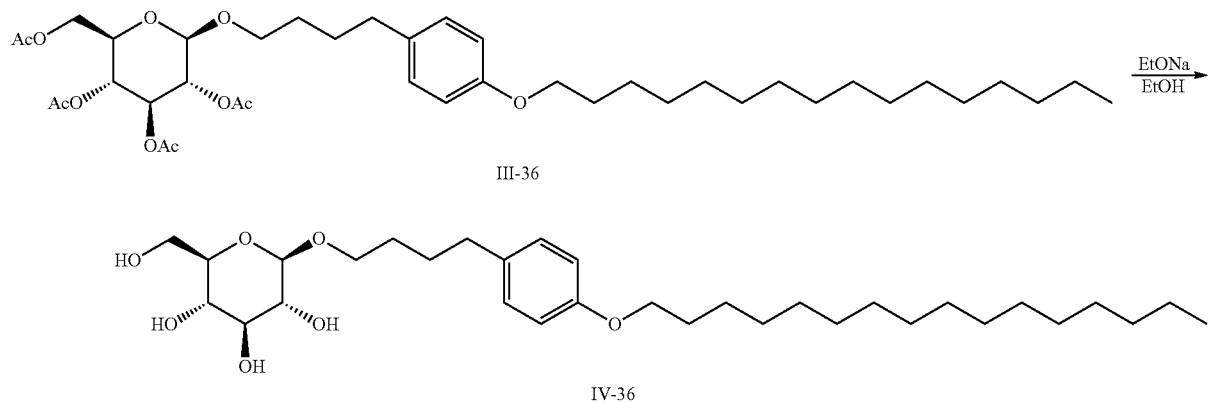

Example 47

Synthesis of 1-[4-(4-((2,5,8,11-tetraoxatridecan-13-yl)oxy)phenyl)butyl]-2,3,4,6-O-tetraacetyl-β-D-glucopyranoside III-37

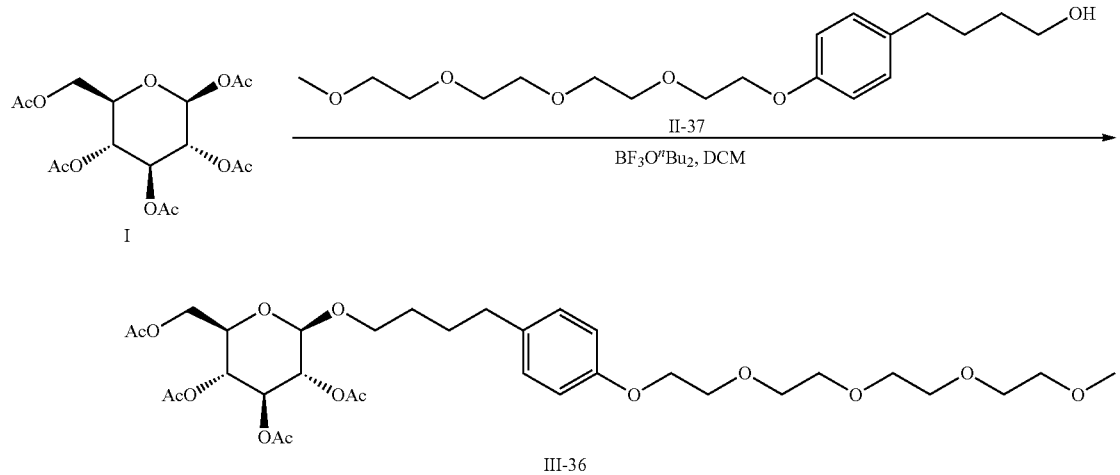

Operation steps: Replace reaction flask with nitrogen for 3 times, add dichloromethane as solvent, and start stirring. Then, add β-D-glucose pentaacetate I and 4-(4-((2,5,8,11-tetraoxatridecan-13-yl)oxy)phenyl)butan-1-ol II-37 in turn. Cool reaction flask to 0±5° C., drop boron trifluoride dibutyl etherate, and continue to stir for 12 h after that. After reaction, drop water to system to quench, separate liquid, wash organic phase with Na$_2$CO$_3$ water solution, separate liquid, and wash organic phase with water once again. Collect organic phase after liquid separation. Conduct column chromatography isolation after organic phase concentration, and obtain compound III-37, with a yield of 30%. LRMS(ESI): [M+Na]$^+$ 709.3.

Synthesis of 1-[4-((2,5,8,11-tetraoxatridecan-13-yl)oxy)]phenylbutyl-β-D-glucopyranoside IV-37

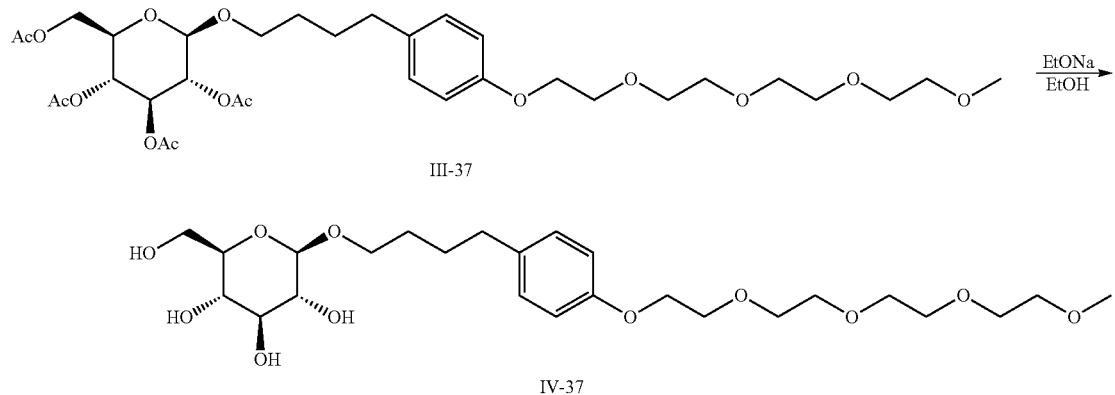

Operation steps: Replace reaction flask with nitrogen for 3 times, add ethanol as solvent, and start stirring. Add intermediate III-37 into reaction flask, control temperature at 25±5° C., add sodium ethoxide into reaction flask, and stir to react for 2 h. After reaction, conduct diatomite filtration, and collect filtrate after ethanol leaching. Add (H$^+$) ion exchange resin and stir for 10 h. Filter to remove (H$^+$) ion exchange resin. Conduct column chromatography isolation after organic phase concentration, and obtain compound IV-37, with a yield of 81%. $^1$H NMR (400 MHz, CD$_3$OD) δ 7.08 (d, J=8.5 Hz, 2H), 6.83 (d, J=8.6 Hz, 2H), 4.23 (d, J=7.8 Hz, 1H), 4.15-4.02 (m, 2H), 3.91 (m, 1H), 3.85 (dd, J=11.8, 1.7 Hz, 1H), 3.83-3.78 (m, 2H), 3.71-3.47 (m, 14H), 3.36-3.17 (m, 7H), 2.56 (t, J=7.0 Hz, 2H), 1.66 (m, 4H). LRMS(ESI): [M+Na]$^+$ 541.2; HRMS(ESI): m/z Calcd for C$_{25}$H$_{42}$O$_{11}$Na$^+$ [M+Na]$^+$: 541.2619, found: 541.2618.

The above description is a general description of the invention. According to the situation or actual needs, the change of form and equivalent substitution can be conducted. Although specific terms are used herein, these terms are used for description, not for restriction. Technicians in this filed can make changes or modifications to the present invention, and these equivalent forms also fall within the scope defined by the attached claims of this application.

The invention claimed is:
1. Preparation method of a glycoside compound is featured by the following two steps of reactions:
(1) Acetyl-protected glucose (I) and alcohol compounds shown in formula (II) react under the catalysis of Lewis acid to obtain intermediates shown in formula (III);

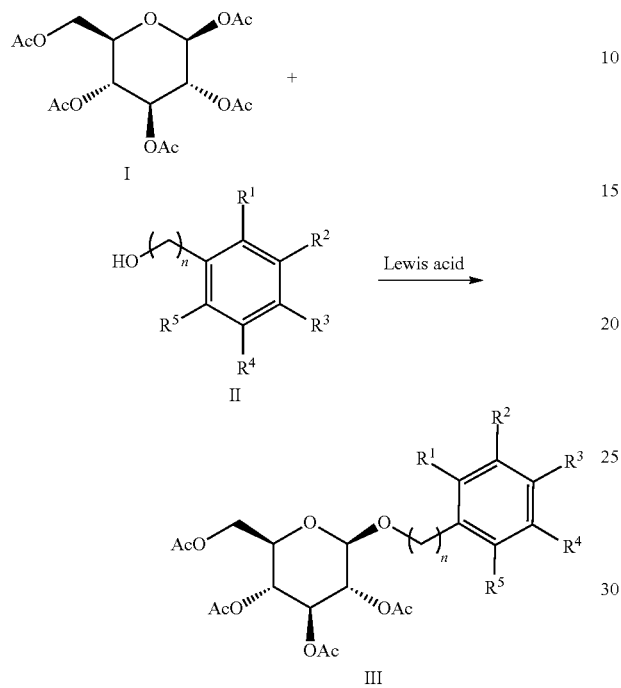

(2) Remove acetyl protecting group from the intermediates shown in formula (III) in the presence of alkali to obtain glycoside compounds shown in formula (IV);

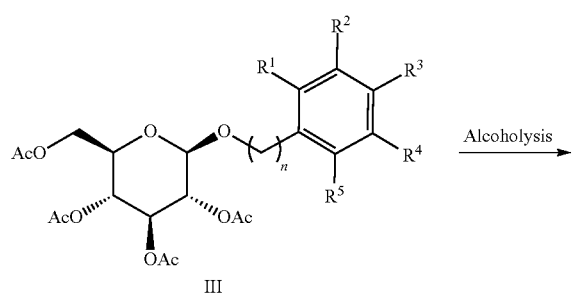

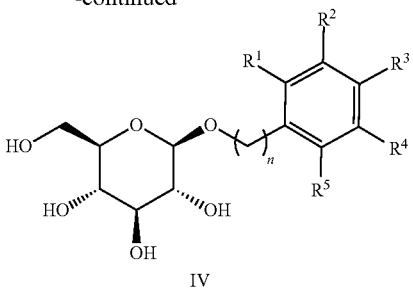

In formulas II, III and IV, substituents $R^1$, $R^2$, $R^3$, $R^4$ and $R^5$ are independently selected from hydrogen, hydroxyl, substituted or unsubstituted $C_1$~$C_{20}$ alkoxyl, substituted or unsubstituted $C_1$~$C_{20}$ alkyl, substituted or unsubstituted $C_1$~$C_{20}$ alkenyl, substituted or unsubstituted $C_1$~$C_{20}$ alkynyl, substituted or unsubstituted aryl, heteroaryl, cycloalkyl, heterocyclyl, nitro or halogen; and n is 4, 5, or 6;

wherein the steps (1) and (2) are carried out under protection of inert gas nitrogen or argon, and reaction temperature in step (1) is 0±5° C.

2. For preparation method as described in claim 1, reaction in step (1) is carried out in the first organic solvent; the first organic solvent as described is one or more of dichloromethane, chloroform, toluene, xylene, dimethylformamide, dioxane, methyl tert-butyl ether or tetrahydrofuran.

3. For preparation method as described in claim 1, Lewis acid in step (1) is one or more of tin tetrachloride, zinc chloride, aluminum trichloride and boron trifluoride complex, such as boron trifluoride diethyl ether complex, boron trifluoride butyl ether complex, boron trifluoride tetrahydrofuran complex, boron trifluoride acetonitrile complex or trimethylsilyl trifluoromethanesulfonate.

4. For preparation method as described in claim 1, reaction in step (2) is carried out in the second organic solvent; the second organic solvent is one or more of methanol, ethanol, isobutanol or tert-butanol.

5. According to the preparation method described in claim 1, where the alkaline condition in step (2) refers to the existence of sodium hydroxide, potassium hydroxide or sodium salt of $C_1$-$C_4$ alkanol.

6. For preparation method as described in claim 5, alkaline condition as described in step (2) refers to that in the presence of sodium methoxide, sodium ethoxide or sodium tert-butoxide.

7. Preparation method as described in claim 1, is featured by compound IV selected from the following compounds:

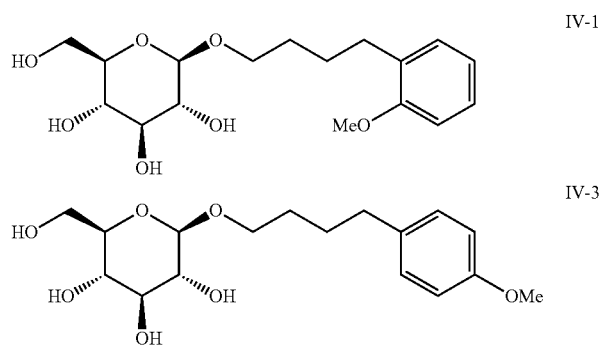

-continued
IV-5
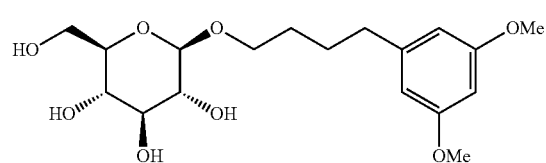
IV-6
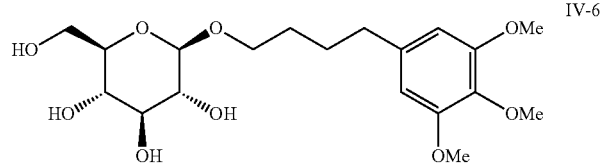
IV-7
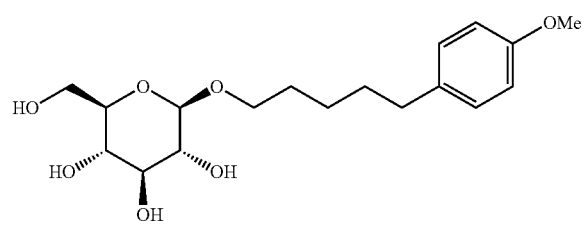
IV-8
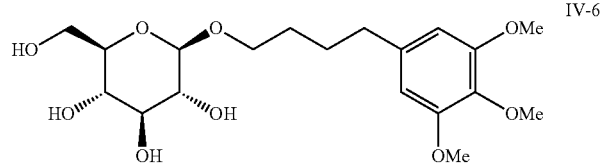
IV-9
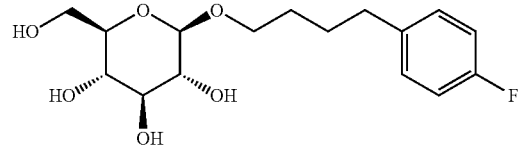
IV-10
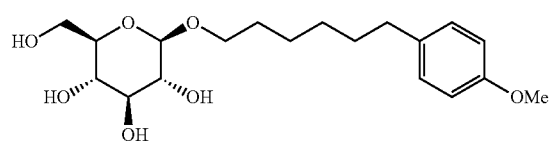
IV-11
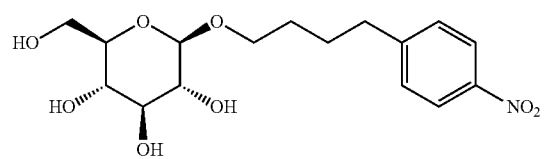
IV-12
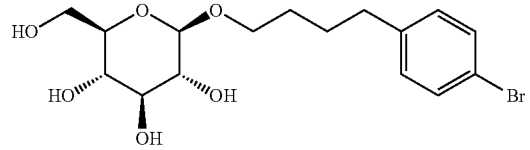
IV-13
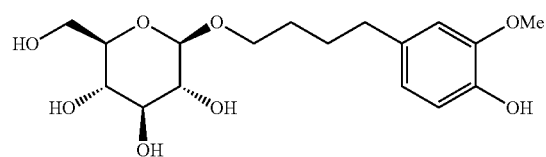
IV-14
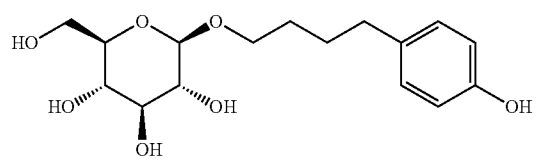
IV-15
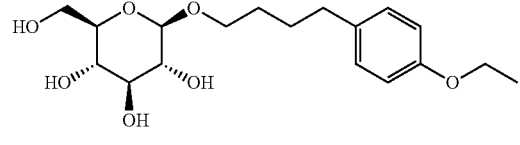
IV-16
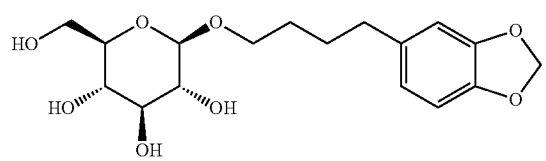
IV-17
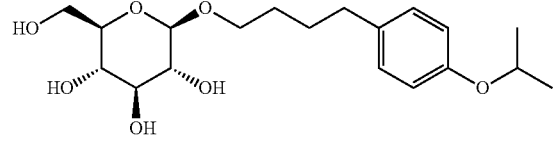
IV-18
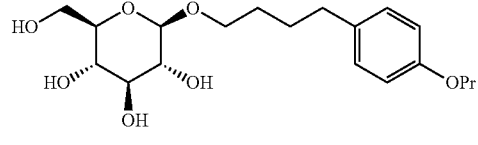
IV-19
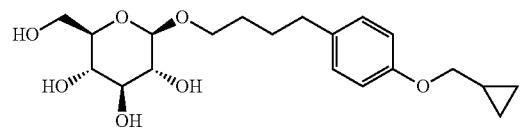
IV-20
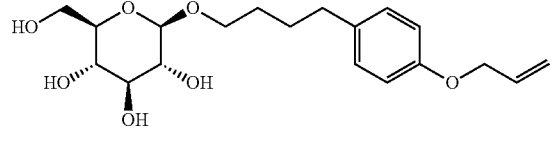
IV-21
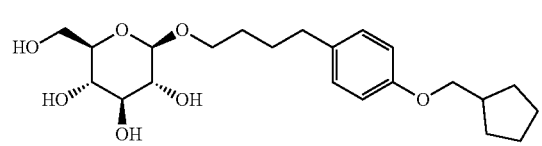
IV-22
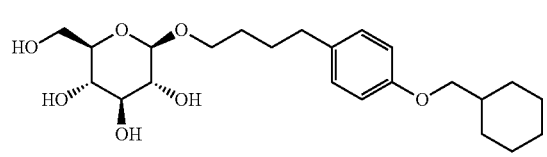

-continued
IV-23
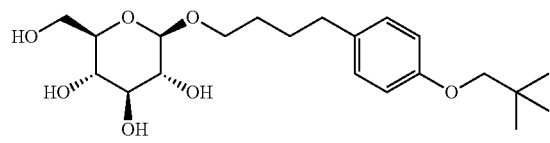
IV-24
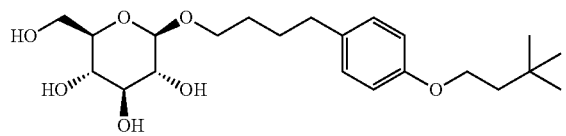
IV-25
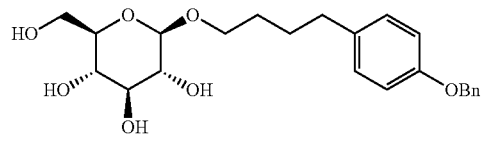
IV-26
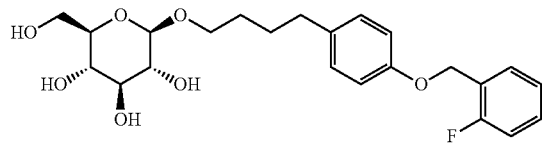
IV-27
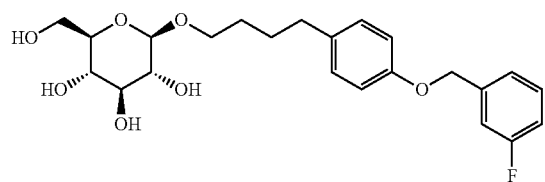
IV-28
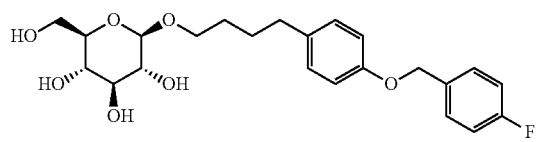
IV-29
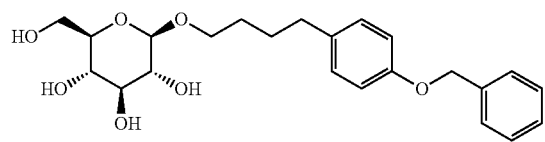
IV-30
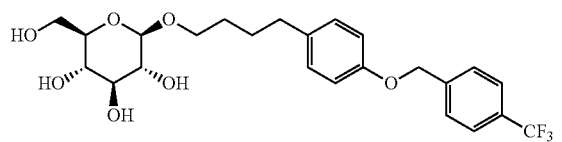
IV-31
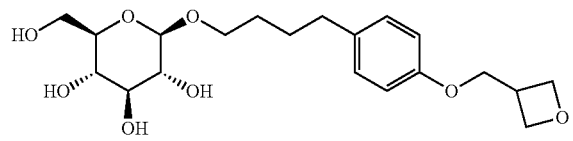
IV-32
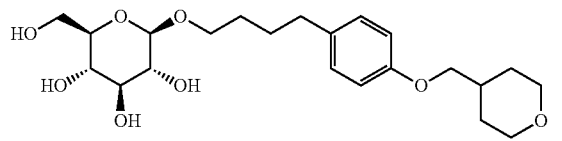
IV-33
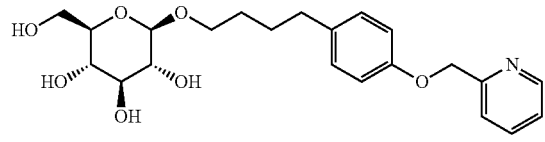
IV-34
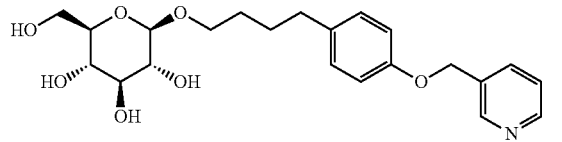
IV-35
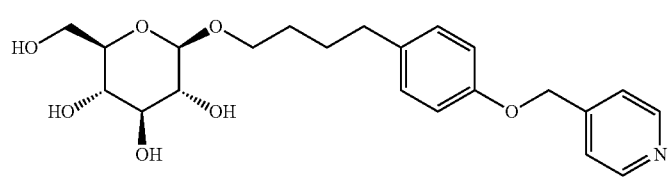
IV-36
IV-37
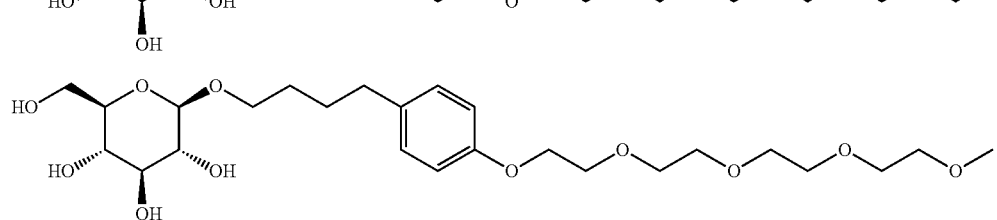
, and
* * * * *